(12) United States Patent
Grinstaff et al.

(10) Patent No.: US 12,281,161 B2
(45) Date of Patent: Apr. 22, 2025

(54) POLYPEPTIDES AND USES THEREOF

(71) Applicant: TRUSTEES OF BOSTON UNIVERSITY, Boston, MA (US)

(72) Inventors: Mark Grinstaff, Brookline, MA (US); Aladin Hamoud, Brookline, MA (US); Samantha Berry, Brighton, MA (US); Christopher Gromisch, Hamden, CT (US); Alina Ringaci, Allston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/873,864

(22) Filed: Jul. 26, 2022

(65) Prior Publication Data
US 2023/0125881 A1    Apr. 27, 2023

Related U.S. Application Data

(60) Provisional application No. 63/226,457, filed on Jul. 28, 2021.

(51) Int. Cl.
*A61K 47/65* (2017.01)
*A61K 47/68* (2017.01)
*C07K 16/28* (2006.01)

(52) U.S. Cl.
CPC .............. *C07K 16/28* (2013.01); *A61K 47/65* (2017.08); *A61K 47/68031* (2023.08); *A61K 47/6849* (2017.08); *C07K 16/2863* (2013.01); *C07K 2317/24* (2013.01); *C07K 2319/30* (2013.01)

(58) Field of Classification Search
CPC .... C07K 16/28; A61K 47/64; A61K 47/6803; A61K 47/6849
See application file for complete search history.

(56) References Cited

U.S. PATENT DOCUMENTS

| | | |
|---|---|---|
| 7,572,895 B2 | 8/2009 | Mather et al. |
| 8,101,177 B2 | 1/2012 | Fuh et al. |
| 8,101,721 B2 | 1/2012 | Yayon et al. |
| 9,751,933 B2 | 9/2017 | Lee et al. |
| 10,800,844 B2 | 10/2020 | Rosenthal et al. |
| 2019/0381186 A1* | 12/2019 | Grinstaff ............ A61K 47/6859 |
| 2020/0115326 A1 | 4/2020 | Systems |
| 2020/0123263 A1 | 4/2020 | Dunn et al. |

FOREIGN PATENT DOCUMENTS

| | | | |
|---|---|---|---|
| EP | 0328248 A3 | 8/1989 | |
| WO | 1995031480 A1 | 11/1995 | |
| WO | 1997012988 A1 | 4/1997 | |
| WO | 2011156617 A2 | 12/2011 | |
| WO | 2013012722 A1 | 1/2013 | |
| WO | WO-2013052015 A1 * | 4/2013 | ............. C07K 14/00 |
| WO | 2014023709 A1 | 2/2014 | |
| WO | 2023009529 A2 | 2/2023 | |

OTHER PUBLICATIONS

Mao H et al Sortase-mediated protein ligation: A new method for protein engineering. Journal of the American Chemical Society 2004 126 (9), 2670-2671 (Year: 2004).*
Wu K, Yang J, Liu J, Kopeček J. Coiled-coil based drug-free macromolecular therapeutics: in vivo efficacy. J Control Release. Jan. 10, 2012;157(1):126-31. (Year: 2012).*
Wuo MG, Mahon AB, Arora PS. An Effective Strategy for Stabilizing Minimal Coiled Coil Mimetics. J Am Chem Soc. Sep. 16, 2015;137(36):11618-21. (Year: 2015).*
Anami Y, Yamazaki CM, Xiong W, Gui X, Zhang N, An Z, Tsuchikama K. Glutamic acid-valine-citrulline linkers ensure stability and efficacy of antibody-drug conjugates in mice. Nat Commun. Jun. 28, 2018;9(1):2512. (Year: 2018).*
International Search Report and Written Opinion issued in PCT/US2022/038356 on Mar. 10, 2023.
Litowski et al. "Designing heterodimeric two-stranded α-helical coiled-coils: effects of hydrophobicity and α-helical propensity on protein folding, stability, and specificity." Journal of Biological Chemistry 277.40 (2002): 37272-37279.
Parry et al. "Microdissection of the sequence and structure of intermediate filament chains." Advances in protein chemistry 70 (2005): 113-142.
Woolfson et al. "The design of coiled-coil structures and assemblies." Advances in protein chemistry 70 (2005): 79-112.

* cited by examiner

*Primary Examiner* — Aurora M Fontainhas
*Assistant Examiner* — Jennifer A Benavides
(74) *Attorney, Agent, or Firm* — Ronald I. Eisenstein; David S. Resnick; Ravinderjit S. Braich

(57) ABSTRACT

Provided herein are novel polypeptides, methods for their production and uses thereof.

23 Claims, 39 Drawing Sheets
Specification includes a Sequence Listing.

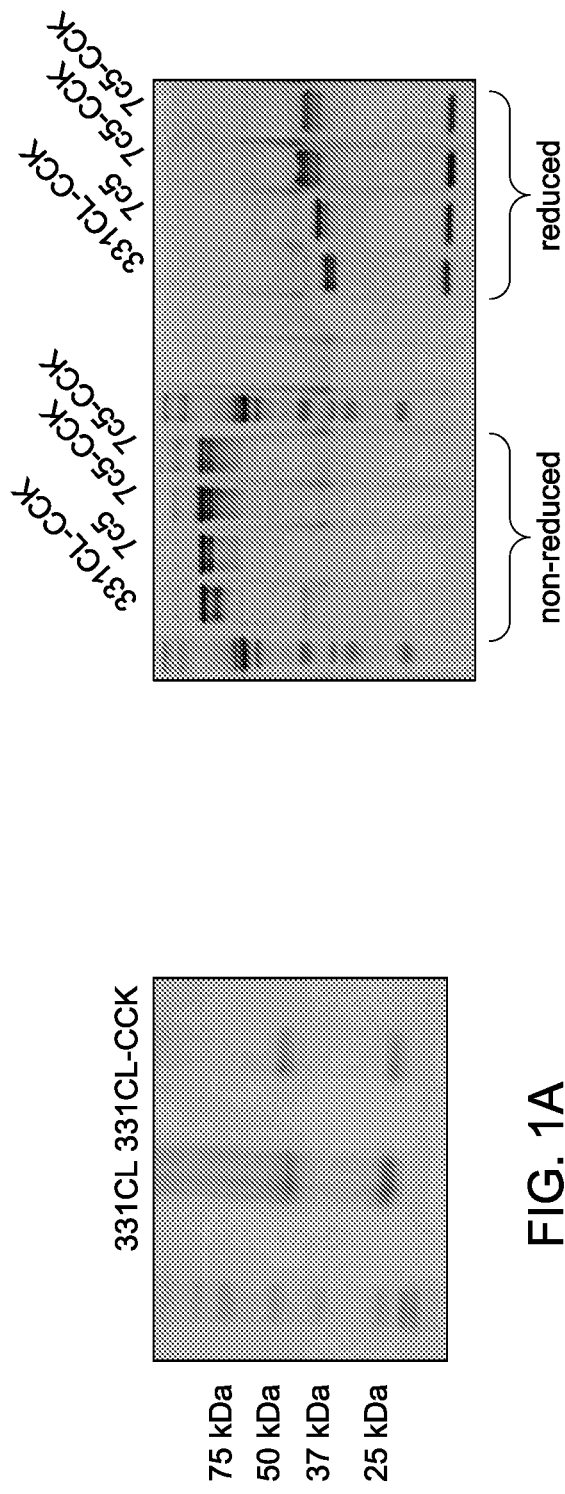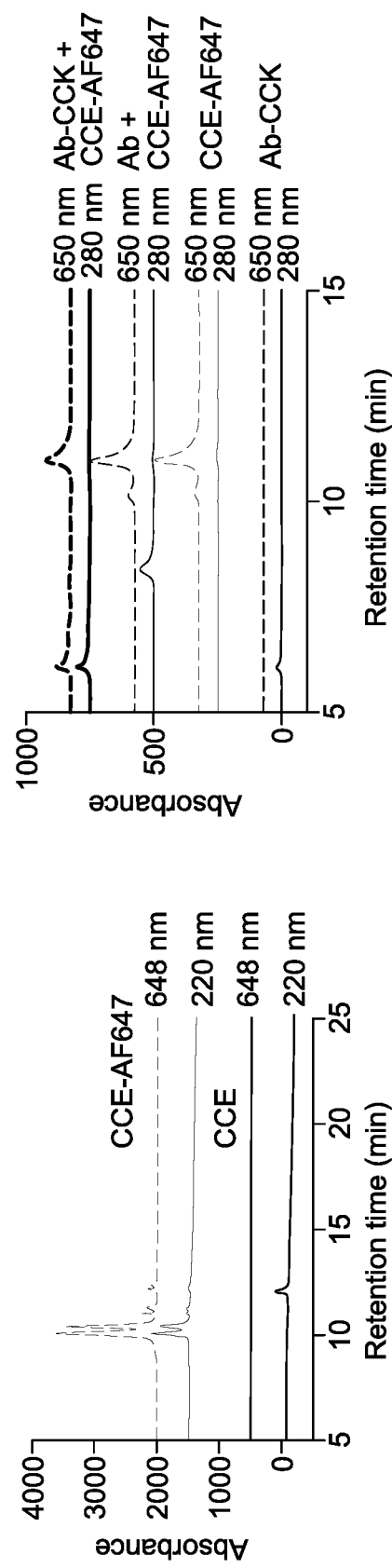
FIG. 1A
FIG. 1B
FIG. 2
FIG. 3

FIG. 4A
FIG. 4B
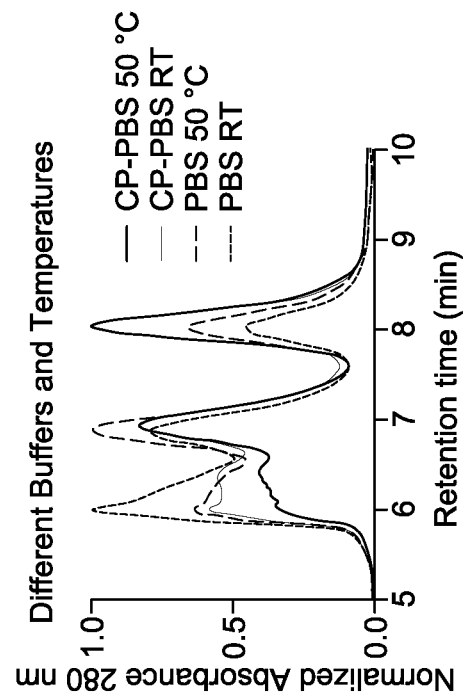
FIG. 4D
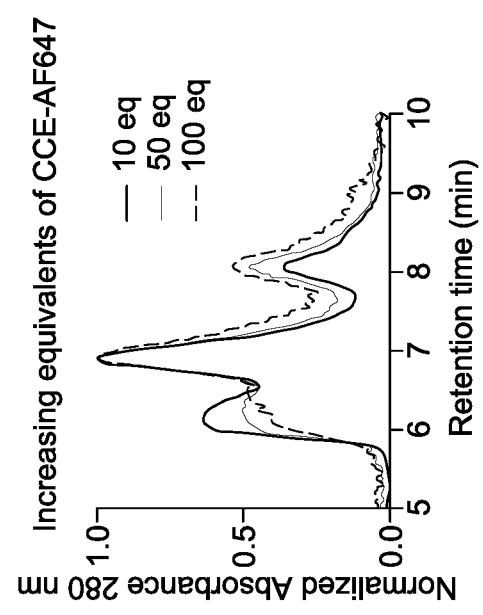
FIG. 4C

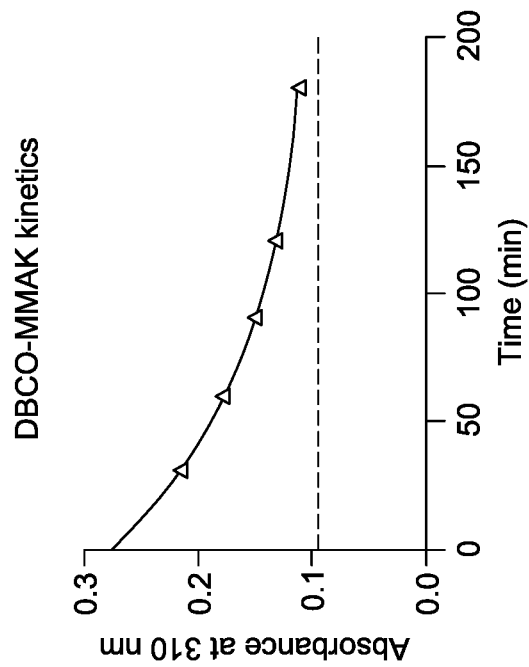
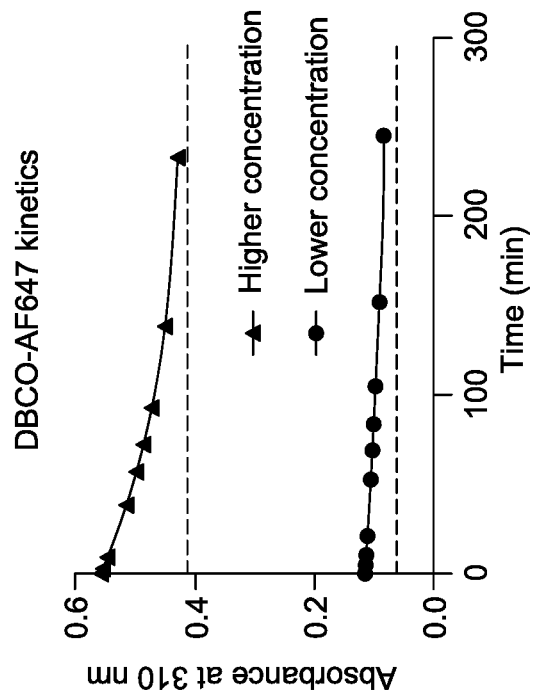
FIG. 7B
FIG. 7A

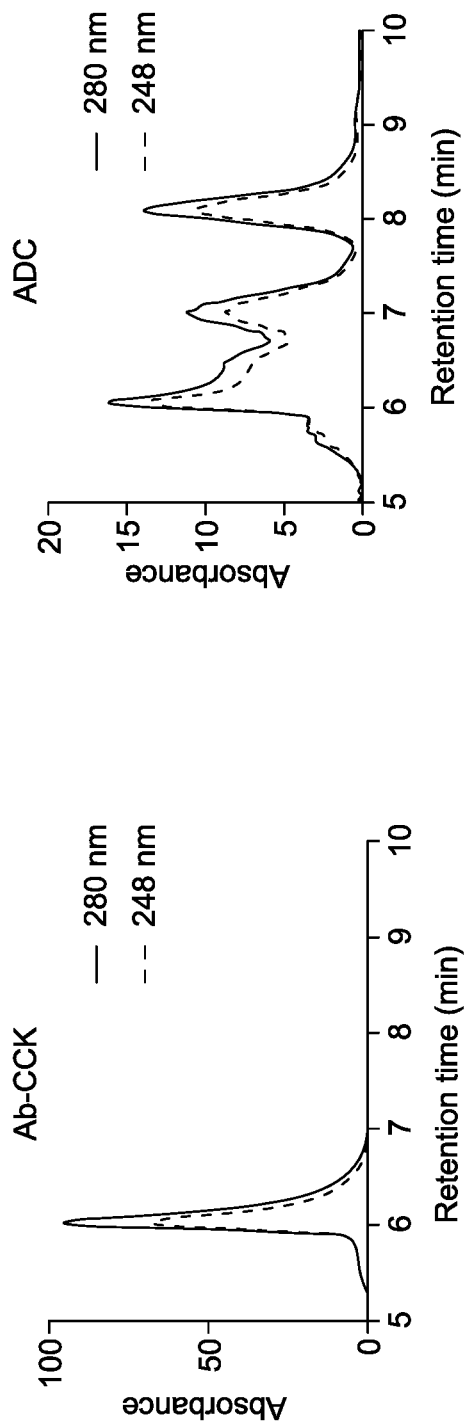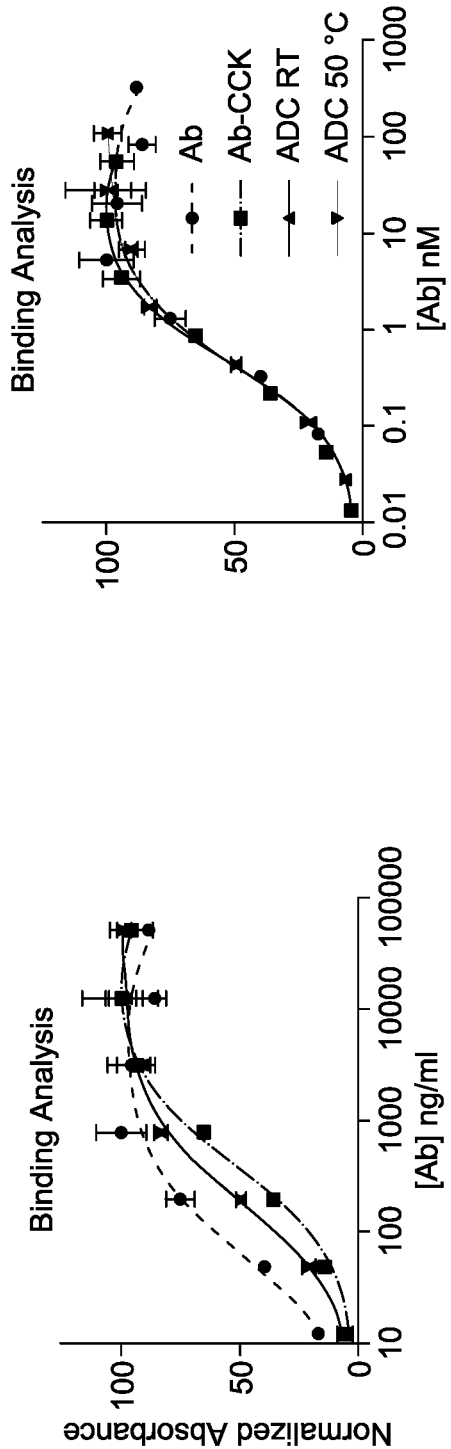
FIG. 9A
FIG. 9B
FIG. 9C
FIG. 9D

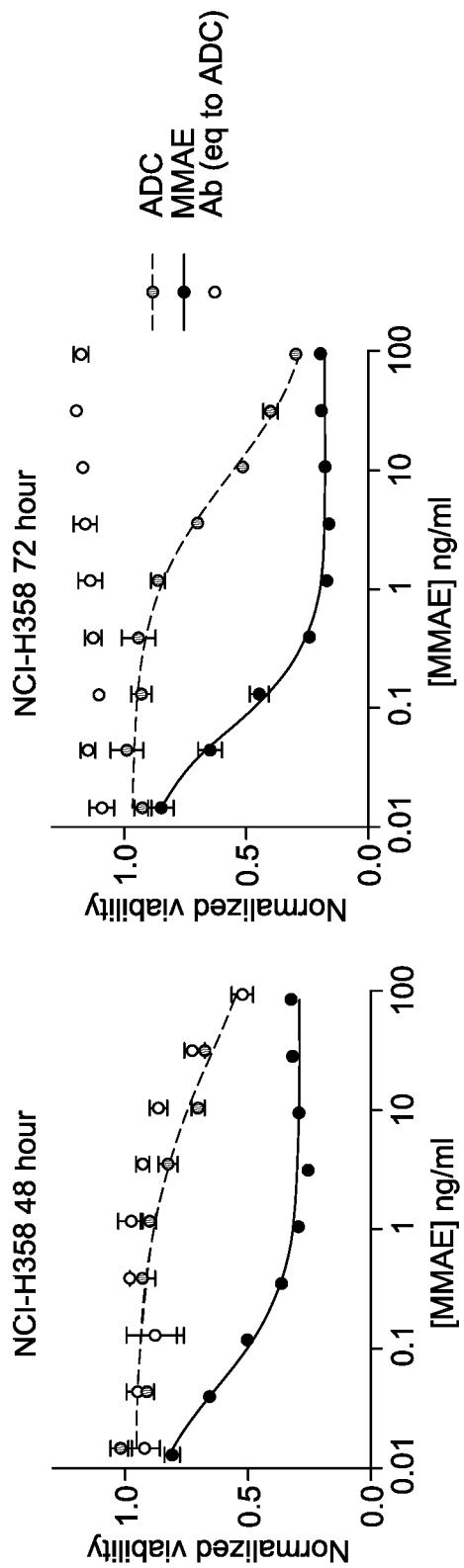
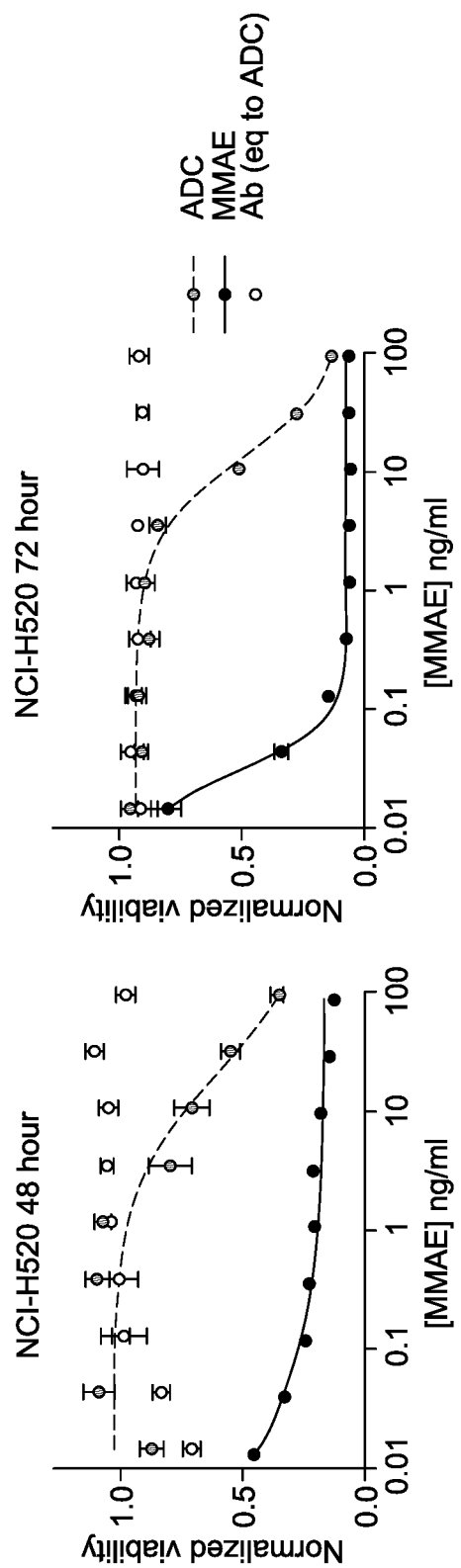
FIG. 13A
FIG. 13B

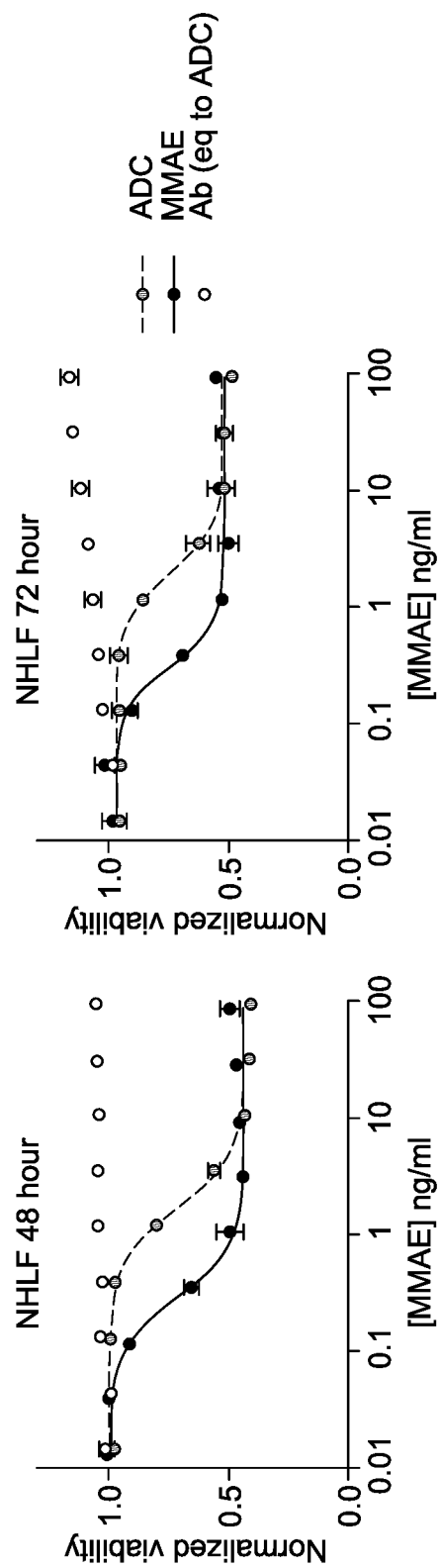
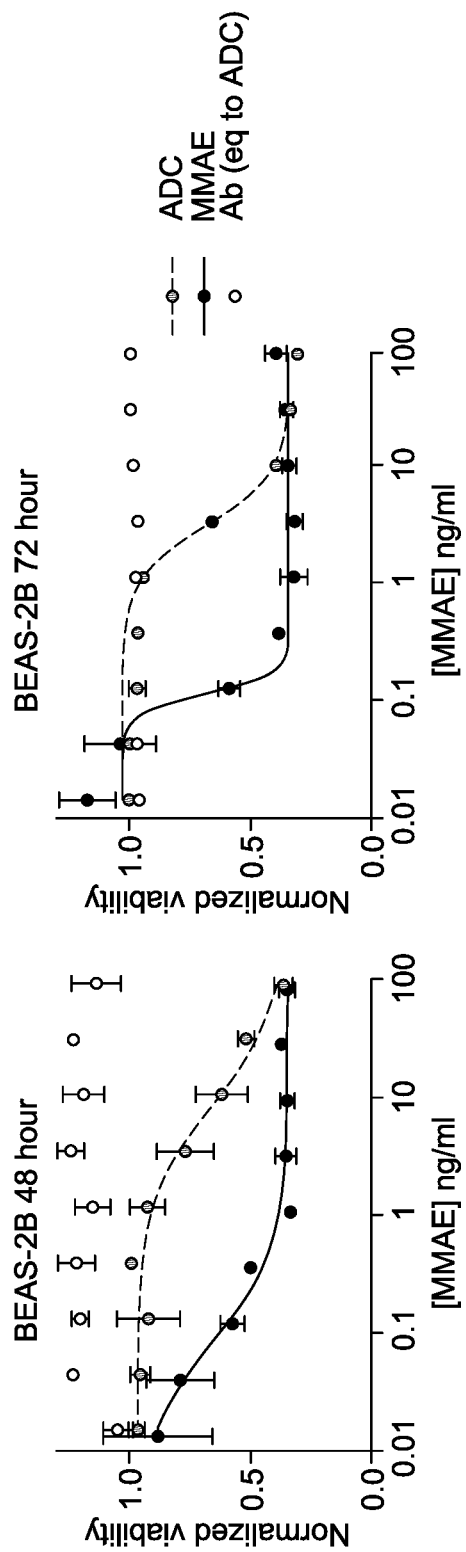
FIG. 13C
FIG. 13D

| Cell line | 48 hour incubation | | 72 hour incubation | |
|---|---|---|---|---|
| | ADC IC$_{50}$ | MMAE IC$_{50}$ | ADC IC$_{50}$ | MMAE IC$_{50}$ |
| NCI-H358 | 37.3 | 0.047 | 9.11 | 0.065 |
| NCI-H520 | 21.8 | 0.004 | 12.87 | 0.031 |
| NHLF | 1.69 | 0.290 | 1.97 | 0.313 |
| BEAS-2B | 8.94 | 0.083 | 3.22 | 0.118 |
| HUVEC | 26.8 | 0.180 | 27.9 | 0.046 |

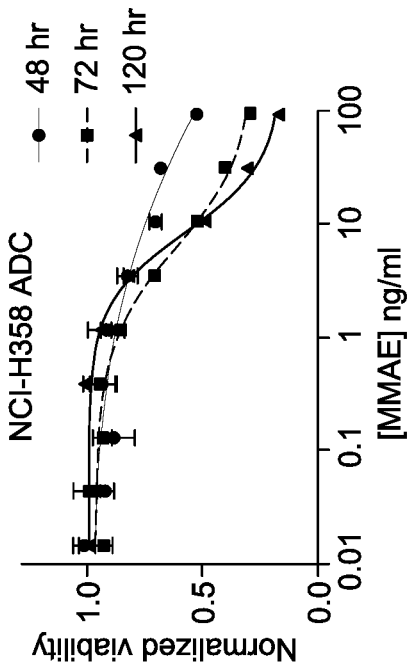
FIG. 15A
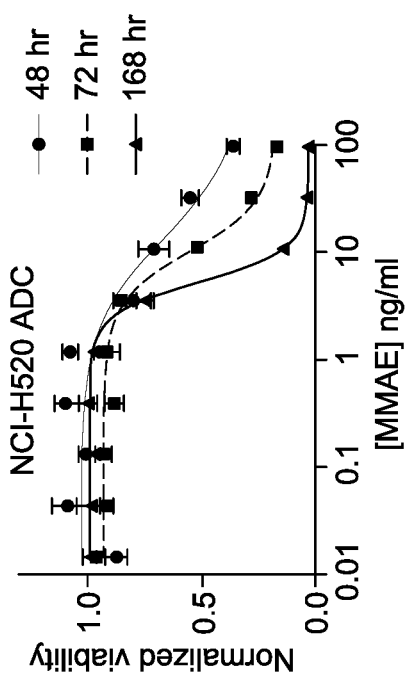
FIG. 15B
| Cell line | 48 hour incubation | | 72 hour incubation | |
|---|---|---|---|---|
| | ADC AUC | MMAE AUC | ADC AUC | MMAE AUC |
| NCI-H358 | 65 | 28 | 41 | 19 |
| NCI-H520 | 54 | 14 | 32 | 6 |
| NHLF | 43 | 43 | 52 | 54 |
| BEAS-2B | 51 | 33 | 37 | 36 |
| HUVEC | 37 | 26 | 61 | 20 |
FIG. 16

| Cell Line | GR50 ADC | GR50 MMAE |
|---|---|---|
| NCI-H358 | 13.6 | 0.21 |
| NCI-H520 | 9.7 | 0.09 |
| NHLF | NA | NA |
| BEAS-2B | 3.5 | NA |

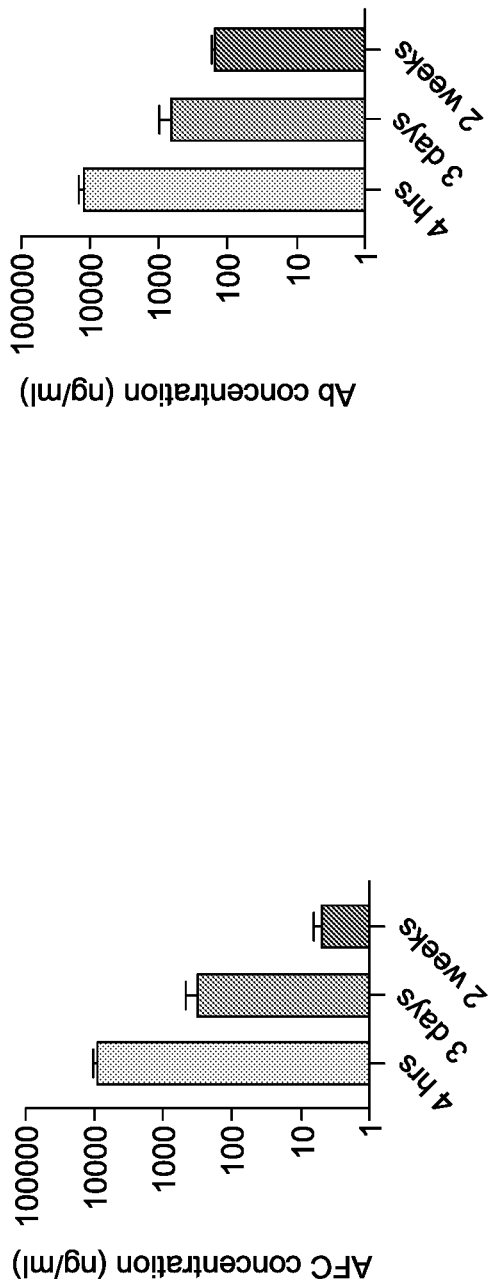
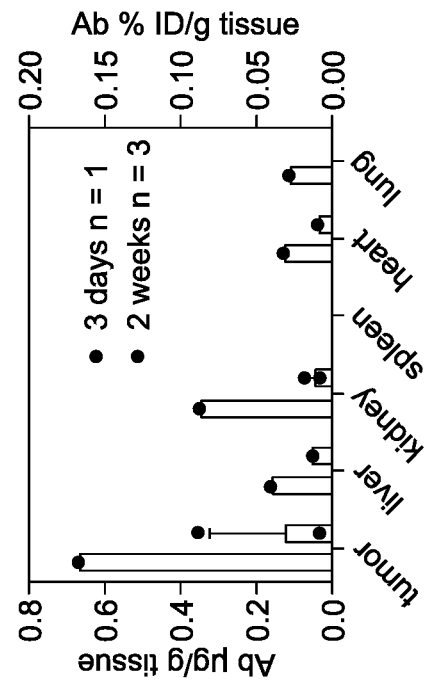
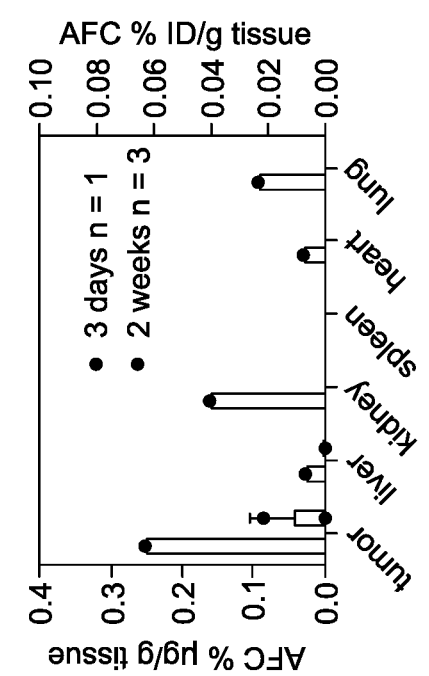

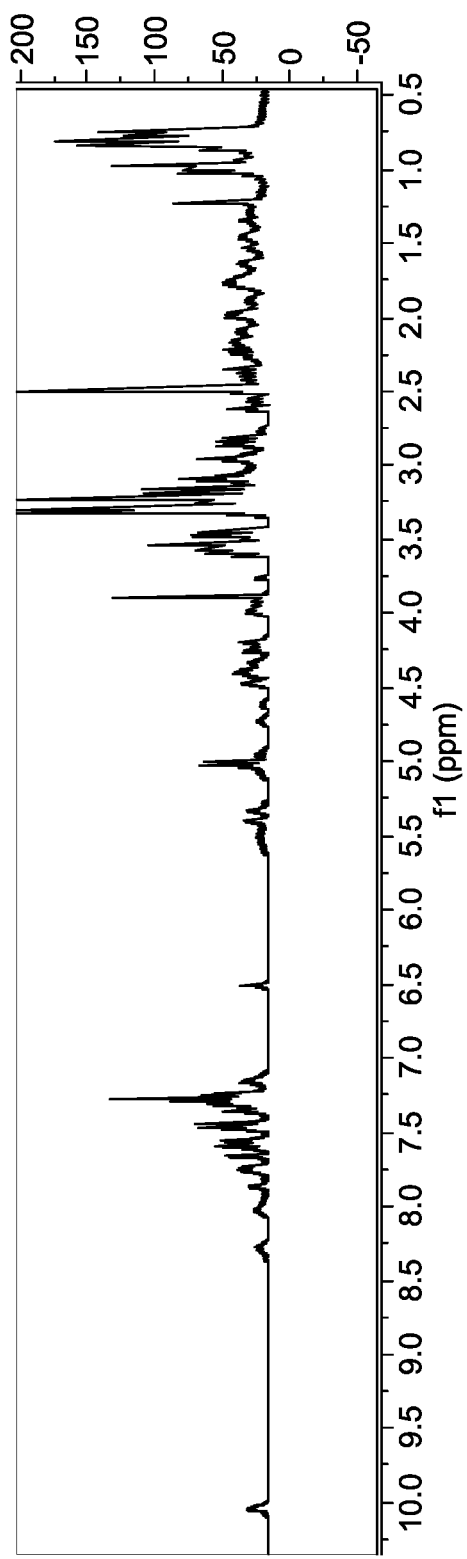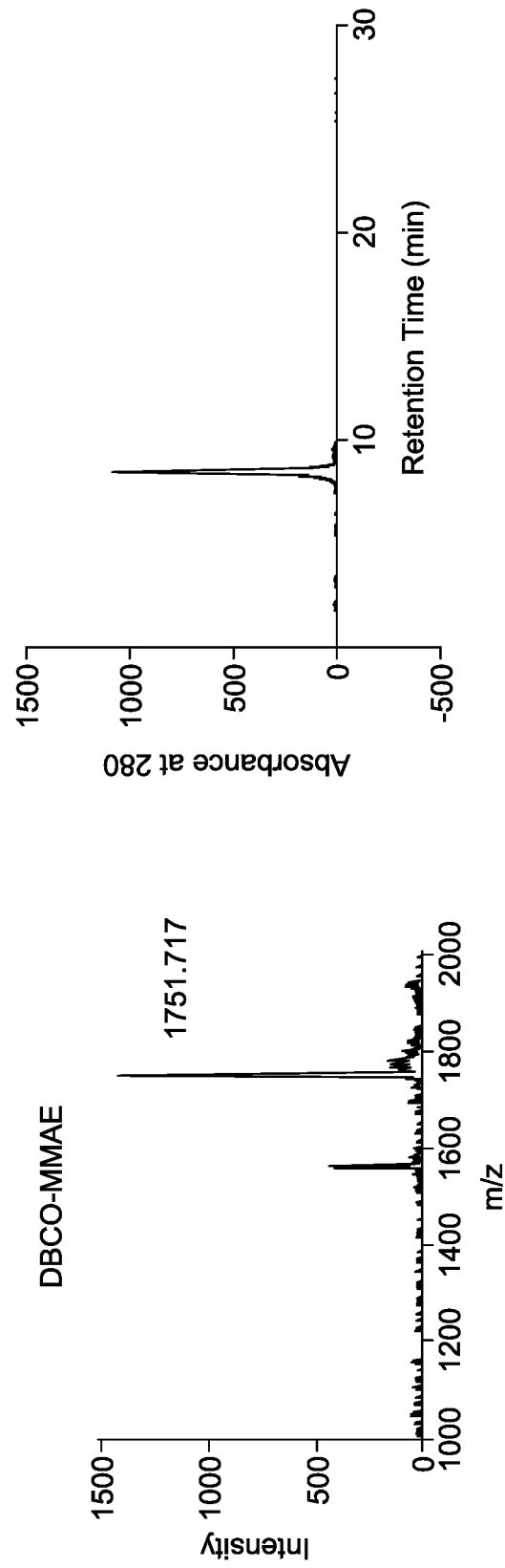
FIG. 24A
FIG. 24B
FIG. 24C

```
                             SEQUENCE LISTING

Sequence total quantity: 77
SEQ ID NO: 1              moltype = AA  length = 34
FEATURE                   Location/Qualifiers
source                    1..34
                          mol_type = protein
                          organism = synthetic construct
SEQUENCE: 1
MKLKKIKSVL KKIKSVLKKI KSVLKKIKSV VGER                                     34

SEQ ID NO: 2              moltype = AA  length = 34
FEATURE                   Location/Qualifiers
source                    1..34
                          mol_type = protein
                          organism = synthetic construct
VARIANT                   8
                          note = X is independently serine, tyrosine, or a
                          N-epsilon-azido lysine
VARIANT                   15
                          note = X is independently serine, tyrosine, or a
                          N-epsilon-azido lysine
VARIANT                   22
                          note = X is independently serine, tyrosine, or a
                          N-epsilon-azido lysine
VARIANT                   29
                          note = X is independently serine, tyrosine, or a
                          N-epsilon-azido lysine
SEQUENCE: 2
MKLEEIVXEL EEIVXELEEI VXELEEIVXE VGER                                     34

SEQ ID NO: 3              moltype = AA  length = 34
FEATURE                   Location/Qualifiers
source                    1..34
                          mol_type = protein
                          organism = synthetic construct
VARIANT                   22
                          note = K-azido is N-epsilon-azido lysine
SEQUENCE: 3
```

```
MKLEEIVSEL EEIVSELEEI VKELEEIVYE VGER                              34

SEQ ID NO: 4            moltype = AA   length = 35
FEATURE                 Location/Qualifiers
source                  1..35
                        mol_type = protein
                        organism = synthetic construct
VARIANT                 35
                        note = azidoG
SEQUENCE: 4
SPEDEIQALE EENAQLEQEN AALEEELAQL EYGKG                             35

SEQ ID NO: 5            moltype = AA   length = 28
FEATURE                 Location/Qualifiers
source                  1..28
                        mol_type = protein
                        organism = synthetic construct
SEQUENCE: 5
LKKIKSVLKK IKSVLKKIKS VLKKIKSV                                     28

SEQ ID NO: 6            moltype = AA   length = 28
FEATURE                 Location/Qualifiers
source                  1..28
                        mol_type = protein
                        organism = synthetic construct
SEQUENCE: 6
LKKIKSVLKK IKSVLKKIKK VLKKIKYV                                     28

SEQ ID NO: 7            moltype = AA   length = 28
FEATURE                 Location/Qualifiers
source                  1..28
                        mol_type = protein
                        organism = synthetic construct
SEQUENCE: 7
LEEIVSELEE IVSELEEIVS ELEEIVSE                                     28

SEQ ID NO: 8            moltype = AA   length = 28
FEATURE                 Location/Qualifiers
source                  1..28
                        mol_type = protein
                        organism = synthetic construct
SEQUENCE: 8
LEEIVSELEE IVSELEEIVK ELEEIVYE                                     28

SEQ ID NO: 9            moltype = AA   length = 39
FEATURE                 Location/Qualifiers
source                  1..39
                        mol_type = protein
                        organism = synthetic construct
SEQUENCE: 9
CYGGKVSALK EKVSALKEEV SANKEKVSAL KEKVSALKE                         39

SEQ ID NO: 10           moltype = AA   length = 35
FEATURE                 Location/Qualifiers
source                  1..35
                        mol_type = protein
                        organism = synthetic construct
SEQUENCE: 10
SPEDEIQQLE EEIAQLEQKN AALKEKNQAL KYGKG                             35

SEQ ID NO: 11           moltype = AA   length = 33
FEATURE                 Location/Qualifiers
source                  1..33
                        mol_type = protein
                        organism = synthetic construct
SEQUENCE: 11
SPEDKIAQLK EKNAALKEKN QQLKEKLQAL KYG                               33

SEQ ID NO: 12           moltype = AA   length = 33
FEATURE                 Location/Qualifiers
source                  1..33
                        mol_type = protein
                        organism = synthetic construct
SEQUENCE: 12
SPEDEIQQLE EEIAQLEQKN AALKEKNQAL KYG                               33

SEQ ID NO: 13           moltype = AA   length = 33
FEATURE                 Location/Qualifiers
source                  1..33
```

```
                                mol_type = protein
                                organism = synthetic construct
SEQUENCE: 13
SPEDKIAQLK QKIQALKQEN QQLEEENAAL EYG                             33

SEQ ID NO: 14           moltype = AA   length = 28
FEATURE                 Location/Qualifiers
source                  1..28
                        mol_type = protein
                        organism = synthetic construct
SEQUENCE: 14
EVSALEKEVS ALEKEVSALE KEVSALEK                                   28

SEQ ID NO: 15           moltype = AA   length = 28
FEATURE                 Location/Qualifiers
source                  1..28
                        mol_type = protein
                        organism = synthetic construct
SEQUENCE: 15
KVSALKEKVS ALKEKVSALK EKVSALKE                                   28

SEQ ID NO: 16           moltype = AA   length = 21
FEATURE                 Location/Qualifiers
source                  1..21
                        mol_type = protein
                        organism = synthetic construct
SEQUENCE: 16
EIAALEKEIA ALEKEIAALE K                                          21

SEQ ID NO: 17           moltype = AA   length = 28
FEATURE                 Location/Qualifiers
source                  1..28
                        mol_type = protein
                        organism = synthetic construct
SEQUENCE: 17
EIAALEKEIA ALEKEIAALE KEIAALEK                                   28

SEQ ID NO: 18           moltype = AA   length = 21
FEATURE                 Location/Qualifiers
source                  1..21
                        mol_type = protein
                        organism = synthetic construct
SEQUENCE: 18
KIAALKEKIA ALKEKIAALK E                                          21

SEQ ID NO: 19           moltype = AA   length = 28
FEATURE                 Location/Qualifiers
source                  1..28
                        mol_type = protein
                        organism = synthetic construct
SEQUENCE: 19
KIAALKEKIA ALKEKIAALK EKIAALKE                                   28

SEQ ID NO: 20           moltype = AA   length = 21
FEATURE                 Location/Qualifiers
source                  1..21
                        mol_type = protein
                        organism = synthetic construct
SEQUENCE: 20
EISALEKEIS ALEKEISALE K                                          21

SEQ ID NO: 21           moltype = AA   length = 28
FEATURE                 Location/Qualifiers
source                  1..28
                        mol_type = protein
                        organism = synthetic construct
SEQUENCE: 21
EISALEKEIS ALEKEISALE KEISALEK                                   28

SEQ ID NO: 22           moltype = AA   length = 21
FEATURE                 Location/Qualifiers
source                  1..21
                        mol_type = protein
                        organism = synthetic construct
SEQUENCE: 22
KISALKEKIS ALKEKISALK E                                          21

SEQ ID NO: 23           moltype = AA   length = 28
FEATURE                 Location/Qualifiers
```

```
source                  1..28
                        mol_type = protein
                        organism = synthetic construct
SEQUENCE: 23
KISALKEKIS ALKEKISALK EKISALKE                                              28

SEQ ID NO: 24           moltype = AA  length = 21
FEATURE                 Location/Qualifiers
source                  1..21
                        mol_type = protein
                        organism = synthetic construct
SEQUENCE: 24
EVAALEKEVA ALEKEVAALE K                                                     21

SEQ ID NO: 25           moltype = AA  length = 28
FEATURE                 Location/Qualifiers
source                  1..28
                        mol_type = protein
                        organism = synthetic construct
SEQUENCE: 25
EVAALEKEVA ALEKEVAALE KEVAALEK                                              28

SEQ ID NO: 26           moltype = AA  length = 21
FEATURE                 Location/Qualifiers
source                  1..21
                        mol_type = protein
                        organism = synthetic construct
SEQUENCE: 26
KVAALKEKVA ALEKVAALK E                                                      21

SEQ ID NO: 27           moltype = AA  length = 28
FEATURE                 Location/Qualifiers
source                  1..28
                        mol_type = protein
                        organism = synthetic construct
SEQUENCE: 27
KVAALKEKVA ALKEKVAALK EKVAALKE                                              28

SEQ ID NO: 28           moltype = AA  length = 21
FEATURE                 Location/Qualifiers
source                  1..21
                        mol_type = protein
                        organism = synthetic construct
SEQUENCE: 28
EVSALEKEVS ALEKEVSALE K                                                     21

SEQ ID NO: 29           moltype =     length =
SEQUENCE: 29
000

SEQ ID NO: 30           moltype = AA  length = 21
FEATURE                 Location/Qualifiers
source                  1..21
                        mol_type = protein
                        organism = synthetic construct
SEQUENCE: 30
KVSALKEKVS ALKEKVSALK E                                                     21

SEQ ID NO: 31           moltype =     length =
SEQUENCE: 31
000

SEQ ID NO: 32           moltype =     length =
SEQUENCE: 32
000

SEQ ID NO: 33           moltype = AA  length = 21
FEATURE                 Location/Qualifiers
source                  1..21
                        mol_type = protein
                        organism = synthetic construct
SEQUENCE: 33
KIATLKEKIA ALKEKIATLK E                                                     21

SEQ ID NO: 34           moltype = AA  length = 21
FEATURE                 Location/Qualifiers
source                  1..21
                        mol_type = protein
                        organism = synthetic construct
```

```
SEQUENCE: 34
EIATLEKEIA ALEKEIATLE K                                                21

SEQ ID NO: 35          moltype = AA  length = 23
FEATURE                Location/Qualifiers
source                 1..23
                       mol_type = protein
                       organism = synthetic construct
SEQUENCE: 35
EIAALEKEIA ALEWEIAALE QGS                                              23

SEQ ID NO: 36          moltype = AA  length = 22
FEATURE                Location/Qualifiers
source                 1..22
                       mol_type = protein
                       organism = synthetic construct
SEQUENCE: 36
KAALKYKIAA LKKKIAALKQ GS                                               22

SEQ ID NO: 37          moltype = AA  length = 23
FEATURE                Location/Qualifiers
source                 1..23
                       mol_type = protein
                       organism = synthetic construct
SEQUENCE: 37
EIAALEKENA ALEWEIAALE QGG                                              23

SEQ ID NO: 38          moltype = AA  length = 22
FEATURE                Location/Qualifiers
source                 1..22
                       mol_type = protein
                       organism = synthetic construct
SEQUENCE: 38
KAALKYKNAA LKKKIAALKQ GG                                               22

SEQ ID NO: 39          moltype = AA  length = 26
FEATURE                Location/Qualifiers
source                 1..26
                       mol_type = protein
                       organism = synthetic construct
SEQUENCE: 39
LEQEIAALEK EIAALEWEIA ALEQGS                                           26

SEQ ID NO: 40          moltype = AA  length = 25
FEATURE                Location/Qualifiers
source                 1..25
                       mol_type = protein
                       organism = synthetic construct
SEQUENCE: 40
LEQKAALKYK IAALKKKIAA LKQGS                                            25

SEQ ID NO: 41          moltype = AA  length = 26
FEATURE                Location/Qualifiers
source                 1..26
                       mol_type = protein
                       organism = synthetic construct
SEQUENCE: 41
LEQEIAALEK ENAALEWEIA ALEQGG                                           26

SEQ ID NO: 42          moltype = AA  length = 23
FEATURE                Location/Qualifiers
source                 1..23
                       mol_type = protein
                       organism = synthetic construct
SEQUENCE: 42
LEQKAALKYK NAALKKKIAA LKQ                                              23

SEQ ID NO: 43          moltype = AA  length = 31
FEATURE                Location/Qualifiers
source                 1..31
                       mol_type = protein
                       organism = synthetic construct
SEQUENCE: 43
GEIAALEQEI AALEKEIAAL EWEIAALEQG S                                     31

SEQ ID NO: 44          moltype = AA  length = 30
FEATURE                Location/Qualifiers
source                 1..30
                       mol_type = protein
```

-continued

```
                            organism = synthetic construct
SEQUENCE: 44
GEIAALEQKA ALKYKIAALK KKIAALKQGS                                              30

SEQ ID NO: 45           moltype = AA  length = 31
FEATURE                 Location/Qualifiers
source                  1..31
                        mol_type = protein
                        organism = synthetic construct
SEQUENCE: 45
GEIAALEQEI AALEKENAAL EWEIAALEQG G                                            31

SEQ ID NO: 46           moltype = AA  length = 30
FEATURE                 Location/Qualifiers
source                  1..30
                        mol_type = protein
                        organism = synthetic construct
SEQUENCE: 46
GEIAALEQKA ALKYKNAALK KKIAALKQGG                                              30

SEQ ID NO: 47           moltype = AA  length = 5
FEATURE                 Location/Qualifiers
source                  1..5
                        mol_type = protein
                        organism = synthetic construct
VARIANT                 3
                        note = X is any amino acid
SEQUENCE: 47
LPXTG                                                                         5

SEQ ID NO: 48           moltype = AA  length = 5
FEATURE                 Location/Qualifiers
source                  1..5
                        mol_type = protein
                        organism = synthetic construct
SEQUENCE: 48
LPETG                                                                         5

SEQ ID NO: 49           moltype = AA  length = 9
FEATURE                 Location/Qualifiers
source                  1..9
                        mol_type = protein
                        organism = synthetic construct
VARIANT                 3
                        note = X is any amino acid
SEQUENCE: 49
LPXTGGGGG                                                                     9

SEQ ID NO: 50           moltype = AA  length = 9
FEATURE                 Location/Qualifiers
source                  1..9
                        mol_type = protein
                        organism = synthetic construct
SEQUENCE: 50
LPETGGGGG                                                                     9

SEQ ID NO: 51           moltype = AA  length = 34
FEATURE                 Location/Qualifiers
source                  1..34
                        mol_type = protein
                        organism = synthetic construct
VARIANT                 22
                        note = X is lysine linked at N-epsilon position with X2-L,
                         where X2 is a linker and L is a ligand
SEQUENCE: 51
MKLEEIVSEL EEIVSELEEI VXELEEIVYE VGER                                          34

SEQ ID NO: 52           moltype = AA  length = 35
FEATURE                 Location/Qualifiers
source                  1..35
                        mol_type = protein
                        organism = synthetic construct
VARIANT                 35
                        note = azidoG
VARIANT                 34
                        note = where X is lysine linked at N-epsilon position with
                         X2-L, where X2 is a linker and L is a ligand
SEQUENCE: 52
SPEDEIQALE EENAQLEQEN AALEEELAQL EYGXG                                         35
```

```
SEQ ID NO: 53          moltype = AA  length = 6
FEATURE                Location/Qualifiers
source                 1..6
                       mol_type = protein
                       organism = synthetic construct
VARIANT                3
                       note = X is any amino acid
VARIANT                6
                       note = X is an affinity tag, at its C-terminus
SEQUENCE: 53
LPXTGX                                                                   6

SEQ ID NO: 54          moltype = AA  length = 6
FEATURE                Location/Qualifiers
source                 1..6
                       mol_type = protein
                       organism = synthetic construct
VARIANT                6
                       note = X is an affinity tag, at its C-terminus
SEQUENCE: 54
LPETGX                                                                   6

SEQ ID NO: 55          moltype = AA  length = 5
FEATURE                Location/Qualifiers
source                 1..5
                       mol_type = protein
                       organism = synthetic construct
SEQUENCE: 55
GGGGG                                                                    5

SEQ ID NO: 56          moltype = AA  length = 28
FEATURE                Location/Qualifiers
source                 1..28
                       mol_type = protein
                       organism = synthetic construct
VARIANT                6
                       note = X is independently serine, tyrosine, or lysine
                         (e.g., N-epsilon-azido-lysine)
VARIANT                13
                       note = X is independently serine, tyrosine, or lysine
                         (e.g., N-epsilon-azido-lysine)
VARIANT                20
                       note = X is independently serine, tyrosine, or lysine
                         (e.g., N-epsilon-azido-lysine)
VARIANT                27
                       note = X is independently serine, tyrosine, or lysine
                         (e.g., N-epsilon-azido-lysine)
SEQUENCE: 56
LEEIVXELEE IVXELEEIVX ELEEIVXE                                          28

SEQ ID NO: 57          moltype = AA  length = 28
FEATURE                Location/Qualifiers
source                 1..28
                       mol_type = protein
                       organism = synthetic construct
VARIANT                20
                       note = K-azido is N-epsilon-azido-lysine
SEQUENCE: 57
LEEIVSELEE IVSELEEIVK ELEEIVYE                                          28

SEQ ID NO: 58          moltype = AA  length = 28
FEATURE                Location/Qualifiers
source                 1..28
                       mol_type = protein
                       organism = synthetic construct
VARIANT                6
                       note = X is independently serine, tyrosine, or lysine
                         linked at the N-epsilon-position with X2-L, where X2 is a
                         linker and L is a payload molecule, e.g., a ligand,
                         provided that one X1 is lysine linked at the 6-posisiton
                         with X2-L
VARIANT                13
                       note = X1 is independently serine, tyrosine, or lysine
                         linked at the N-epsilon-position with X2-L, where X2 is a
                         linker and L is a payload molecule, e.g., a ligand,
                         provided that one X1 is lysine linked at the 6-posisiton
                         with X2-L
VARIANT                20
```

```
                        note = X1 is independently serine, tyrosine, or lysine
                            linked at the N-epsilon-position with X2-L, where X2 is a
                            linker and L is a payload molecule, e.g., a ligand,
                            provided that one X1 is lysine linked at the 6-posisiton
                            with X2-L
VARIANT                 27
                        note = X1 is independently serine, tyrosine, or lysine
                            linked at the N-epsilon-position with X2-L, where X2 is a
                            linker and L is a payload molecule, e.g., a ligand,
                            provided that one X1 is lysine linked at the 6-posisiton
                            with X2-L
SEQUENCE: 58
LEEIVXELEE IVXELEEIVX ELEEIVXE                                              28

SEQ ID NO: 59           moltype = AA  length = 34
FEATURE                 Location/Qualifiers
source                  1..34
                        mol_type = protein
                        organism = synthetic construct
VARIANT                 8
                        note = X is independently serine, tyrosine, or lysine
                            linked at the N-epsilon-position with X2-L, where X2 is a
                            linker and L is a payload molecule, e.g., a ligand,
                            provided that one X1 is lysine linked at the 6-posisiton
                            with X2-L
VARIANT                 15
                        note = X is independently serine, tyrosine, or lysine
                            linked at the N-epsilon-position with X2-L, where X2 is a
                            linker and L is a payload molecule, e.g., a ligand,
                            provided that one X1 is lysine linked at the 6-posisiton
                            with X2-L
VARIANT                 22
                        note = X is independently serine, tyrosine, or lysine
                            linked at the N-epsilon-position with X2-L, where X2 is a
                            linker and L is a payload molecule, e.g., a ligand,
                            provided that one X1 is lysine linked at the 6-posisiton
                            with X2-L
VARIANT                 29
                        note = X is independently serine, tyrosine, or lysine
                            linked at the N-epsilon-position with X2-L, where X2 is a
                            linker and L is a payload molecule, e.g., a ligand,
                            provided that one X1 is lysine linked at the 6-posisiton
                            with X2-L
SEQUENCE: 59
MKLEEIVXEL EEIVXELEEI VXELEEIVXE VGER                                       34

SEQ ID NO: 60           moltype = AA  length = 28
FEATURE                 Location/Qualifiers
source                  1..28
                        mol_type = protein
                        organism = synthetic construct
VARIANT                 20
                        note = X is lysine linked at the 6-position with X2-L,
                            where X2 is a linker and L is a payload molecule
SEQUENCE: 60
LEEIVSELEE IVSELEEIVX ELEEIVYE                                              28

SEQ ID NO: 61           moltype = AA  length = 9
FEATURE                 Location/Qualifiers
source                  1..9
                        mol_type = protein
                        organism = synthetic construct
SEQUENCE: 61
GWSHPQFEK                                                                   9

SEQ ID NO: 62           moltype = AA  length = 6
FEATURE                 Location/Qualifiers
source                  1..6
                        mol_type = protein
                        organism = synthetic construct
SEQUENCE: 62
HHHHHH                                                                      6

SEQ ID NO: 63           moltype = AA  length = 9
FEATURE                 Location/Qualifiers
source                  1..9
                        mol_type = protein
                        organism = synthetic construct
SEQUENCE: 63
```

```
YPYDVPDYA                                                                           9

SEQ ID NO: 64         moltype = AA  length = 10
FEATURE               Location/Qualifiers
source                1..10
                      mol_type = protein
                      organism = synthetic construct
SEQUENCE: 64
EQKLISEEDL                                                                         10

SEQ ID NO: 65         moltype = AA  length = 6
FEATURE               Location/Qualifiers
source                1..6
                      mol_type = protein
                      organism = synthetic construct
SEQUENCE: 65
DTYRYI                                                                              6

SEQ ID NO: 66         moltype = AA  length = 8
FEATURE               Location/Qualifiers
source                1..8
                      mol_type = protein
                      organism = synthetic construct
SEQUENCE: 66
DYKDDDDK                                                                            8

SEQ ID NO: 67         moltype =     length =
SEQUENCE: 67
000

SEQ ID NO: 68         moltype =     length =
SEQUENCE: 68
000

SEQ ID NO: 69         moltype =     length =
SEQUENCE: 69
000

SEQ ID NO: 70         moltype = AA  length = 14
FEATURE               Location/Qualifiers
source                1..14
                      mol_type = protein
                      organism = synthetic construct
SEQUENCE: 70
LPETGGWSHP QFEK                                                                    14

SEQ ID NO: 71         moltype = AA  length = 23
FEATURE               Location/Qualifiers
source                1..23
                      mol_type = protein
                      organism = synthetic construct
SEQUENCE: 71
NTTTTTTTTT TGGTGGCGAG ACG                                                          23

SEQ ID NO: 72         moltype = AA  length = 459
FEATURE               Location/Qualifiers
source                1..459
                      mol_type = protein
                      organism = synthetic construct
SEQUENCE: 72
EFAATMHSSA LLCCLVLLTG VRAEVQLQQS GPDLVKPGAS MKISCKASGY SFTDYTMHWV                   60
KQSHGKNFEW IGLINPYNDG TTYNQKFKGK ATLTVDKSSS TAYMELLSLT SEDSAVYYCA                  120
SLDYWGQGTS VTVSSAKTTP PSVYPLAPGS AAQTNSMVTL GCLVKGYFPE PVTVTWNSGS                  180
LSSGVHTFPA VLQSDLYTLS SSVTVPSSTW PSETVTCNVA HPASSTKVDK KIVPRDCGCK                  240
PCICTVPEVS SVFIFPPKPK DVLTITLTPK VTCVVVDISK DDPEVQFSWF VDDVEVHTAQ                  300
TQPREEQFNS TFRSVSELPI MHQDWLNGKE FKCRVNSAAF PAPIEKTISK TKGRPKAPQV                  360
YTIPPPKEQM AKDKVSLTCM ITDFFPEDIT VEWQWNGQPA ENYKNTQPIM DTDGSYFVYS                  420
KLNVQKSNWE AGNTFTCSVL HEGLHNHHTE KSLSHSPGK                                         459

SEQ ID NO: 73         moltype = AA  length = 271
FEATURE               Location/Qualifiers
source                1..271
                      mol_type = protein
                      organism = synthetic construct
SEQUENCE: 73
NTTHYRETQA GRLNGPSRLE RPPLCWISAE FAATMHSSAL LCCLVLLTGV RADVVMTQTP                   60
LSLPVSLGDQ ASISCRSSQS LVHSSGNTYL HWYLQKPGQS PKLLIYKVSN RFSGVPDRFS                  120
GSGSGTDFTL KISRVEAEDL GVYFCSQSTH VPYTFGGGTK LEIKRADAAP TVSIFPPSSE                  180
QLTSGGASVV CFLNNFYPKD INVKWKIDGS ERQNGVLNSW TDQDSKDSTY SMSSTLTLTK                  240
```

```
DEYERHNSYT CEATHKTSTS PIVKSFNRNE C                                      271

SEQ ID NO: 74           moltype = AA  length = 479
FEATURE                 Location/Qualifiers
source                  1..479
                        mol_type = protein
                        organism = synthetic construct
SEQUENCE: 74
EFAATMHSSA LLCCLVLLTG VRAQVQLKES GPGLVAPSQS LSITCTVSGF SLTSYDISWI    60
RQPPGKGLEW LGVIWTGGGT NYNSAFMSRL SISKDNSKSQ VFLKMNSLQT DDTAIYYCVR   120
DRDYDGWYFD VWGAGTTVTV SSAKTTPPSV YPLAPGCGDT TGSSVTLGCL VKGYFPESVT   180
VTWNSGSLSS SVHTFPALLQ SGLYTMSSSV TVPSSTWPSQ TVTCSVAHPA SSTTVDKKLE   240
PSGPISTINP CPPCKECHKC PAPNLEGGPS VFIFPPNIKD VLMISLTPKV TCVVVDVSED   300
DPDVQISWFV NNVEVHTAQT QTHREDYNST IRVVSTLPIQ HQDWMSGKEF KCKVNNKDLP   360
SPIERTISKI KGLVRAPQVY ILPPPAEQLS RKDVSLTCLV VGFNPGDISV EWTSNGHTEE   420
NYKDTAPVLD SDGSYFIYSK LNMKTSKWEK TDSFSCNVRH EGLKNYYLKK TISRSPGKD    479

SEQ ID NO: 75           moltype = AA  length = 243
FEATURE                 Location/Qualifiers
source                  1..243
                        mol_type = protein
                        organism = synthetic construct
SEQUENCE: 75
EFAATMHSSA LLCCLVLLTG VRADVLMTQT PLSLPVSLGD QASISCRSSQ SIVHSNGNTY    60
LEWYLQKPGQ SPKLLIYKVS NRFSGVPDRF SGSGSGTDFT LKISRVEAED LGVYYCFQGS   120
HVPYTFGGGT KLEIKRADAA PTVSIFPPSS EQLTSGGASV VCFLNNFYPK DINVKWKIDG   180
SERQNGVLNS WTDQDSKDST YSMSSTLTLT KDEYERHNSY TCEATHKTST SPIVKSFNRN   240
ECD                                                                 243

SEQ ID NO: 76           moltype = AA  length = 469
FEATURE                 Location/Qualifiers
source                  1..469
                        mol_type = protein
                        organism = synthetic construct
SEQUENCE: 76
MHSSALLCCL VLLTGVRAEV QLVESGGGLV QPGGSLRLSC AASGFNIKDT YIHWVRQAPG    60
KGLEWVARIY PTNGYTRYAD SVKGRFTISA DTSKNTAYLQ MNSLRAEDTA VYYCSRWGGD   120
GFYAMDYWGQ GTLVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSREEMT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGGD               469

SEQ ID NO: 77           moltype = AA  length = 233
FEATURE                 Location/Qualifiers
source                  1..233
                        mol_type = protein
                        organism = synthetic construct
SEQUENCE: 77
MHSSALLCCL VLLTGVRADI QMTQSPSSLS ASVGDRVTIT CRASQDVNTA VAWYQQKPGK    60
APKLLIYSAS FLYSGVPSRF SGSRSGTDFT LTISSLQPED FATYYCQQHY TTPPTFGQGT   120
KVEIKRTVAA PSVFIFPPSD EQLKSGTASV VCLLNNFYPR EAKVQWKVDN ALQSGNSQES   180
VTEQDSKDST YSLSSTLTLS KADYEKHKVY ACEVTHQGLS SPVTKSFNRG ECD          233
```

POLYPEPTIDES AND USES THEREOF

CROSS-REFERENCE TO RELATED APPLICATIONS

This application claims benefit under 35 U.S.C. § 119(e) of the U.S. Provisional Application No. 63/226,457, filed Jul. 28, 2021, the content of which is incorporated herein by reference in its entirety.

GOVERNMENT SUPPORT

This invention was made with government support under Contract No. HL144253 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Sep. 13, 2022, is named 701586-190630WOPT.xml and is 78,000 bytes in size.

TECHNICAL FIELD

The technology described herein relates to methods and compositions for novel polypeptide engineering and production.

BACKGROUND

Antibody-drug conjugates (ADCs) are biopharmaceutical products where an antibody, e.g., a monoclonal antibody is linked to a small molecule drug with a stable linker. Most ADCs that are developed are used to treat cancer, but can be applied to treat other diseases. As ADCs are applied as treatments for other diseases, improvements on the antibodies themselves, stable linkers and binding to different small molecule drugs are needed.

The present disclosure addresses some of these needs.

SUMMARY

In one aspect, provided herein is an antibody, where a polypeptide chain, e.g., heavy chain of the antibody linked on its C-terminus to a coiled-coil peptide. The coiled-coil peptide is capable of forming a heterodimer with another coiled-coil peptide.

Exemplary amino acid sequences for the coiled-coil peptides described herein include, but are not limited to the following:

MK(LKKIKSV)$_4$VGER (SEQ ID NO: 1), CCK peptide;
MK(LEEIVXE)$_4$VGER where each X is independently serine, tyrosine, or a N-ε-azido lysine (SEQ ID NO: 2);
MK(LEEIVSE)$_2$LEEIV(K-azido)ELEEIVYEVGER, where K-azido is N-ε-azido lysine (SEQ ID NO: 3), CCE peptide;
SPEDEIQALEEENAQLEQENAALEEE LAQLEYGK-azidoG (SEQ ID NO: 4)
LKKIKSV LKKIKSV LKKIKSV LKKIKSV (SEQ ID NO: 5);
LKKIKSV LKKIKSV LKKIKKV LKKIKYV (SEQ ID NO: 6);
LEEIVSE LEEIVSE LEEIVSE LEEIVSE (SEQ ID NO: 7);
LEEIVSE LEEIVSE LEEIVKE LEEIVYE (SEQ ID NO: 8);
CYGGKVSALKEKVSAL-KEEVSANKEKVSALKEKVSALKE (SEQ ID NO: 9);
SPEDEIQQLEEEIAQLEQKNAALKEKNQALKYGKG (SEQ ID NO: 10);
SPEDKIAQLKEK NAALKEKNQQLKEKLQALKYG (SEQ ID NO: 11);
SPEDEIQQLEEEIAQLEQKNAALKEKNQALKYG (SEQ ID NO: 12);
SPEDKIAQLKQKIQALKQENQQLEEENAALEYG (SEQ ID NO: 13).
EVSALEKEVSALEKEVSALEKEVSALEK (SEQ ID NO: 14);
KVSALKEKVSALKEKVSALKEKVSALKE (SEQ ID NO: 15);
EIAALEKEIAALEKEIAALEK (SEQ ID NO: 16);
EIAALEKEIAALEKEIAALEKEIAALEK (SEQ ID NO: 17);
KIAALKEKIAALKEKIAALKE (SEQ ID NO: 18);
KIAALKEKIAALKEKIAALKEKIAALKE (SEQ ID NO: 19);
EISALEKEISALEKEISALEK (SEQ ID NO: 20);
EISALEKEISALEKEISALEKEISALEK (SEQ ID NO: 21);
KISALKEKISALKEKISALKE (SEQ ID NO: 22);
KISALKEKISALKEKISALKEKISALKE (SEQ ID NO: 23);
EVAALEKEVAALEKEVAALEK (SEQ ID NO: 24);
EVAALEKEVAALEKEVAALEKEVAALEK (SEQ ID NO: 25);
KVAALKEKVAALKEKVAALKE (SEQ ID NO: 26);
KVAALKEKVAALKEKVAALKEKVAALKE (SEQ ID NO: 27);
EVSALEKEVSALEKEVSALEK (SEQ ID NO: 28);
EVSALEKEVSALEKEVSALEKEVSALEK (SEQ ID NO: 14);
KVSALKEKVSALKEKVSALKE (SEQ ID NO: 30);
KIAALKEKIAALKEKIAALKE (SEQ ID NO: 18);
EIAALEK EIAALEK EIAALEK (SEQ ID NO: 16);
KIATLKE-KIAALKE-KIATLKE (SEQ ID NO: 33);
EIATLEK-EIAALEK-EIATLEK (SEQ ID NO: 34);
EIAALEKEIAALEWEIAALEQGS (SEQ ID NO: 35);
KAALKY KIAALKK KIAALKQ GS (SEQ ID NO: 36);
EIAALEKENAALEWEIAALEQGG (SEQ ID NO: 37);
KAALKY KNAALKK KIAALKQ GG (SEQ ID NO: 38);
LEQEIAALEKEIAALEWEIAALEQGS (SEQ ID NO: 39);
LEQKAALKY KIAALKK KIAALKQ GS (SEQ ID NO: 40);
LEQEIAALEKENAALEWEIAALEQGG (SEQ ID NO: 41);
LEQKAALKY KNAALKK KIAALKQ GG (SEQ ID NO: 42);
GEIAALEQEIAALEKEIAALEWEIAALEQGS (SEQ ID NO: 43);
GEIAALEQKAALKY KIAALKK KIAALKQ GS (SEQ ID NO: 44);
GEIAALEQEIAALEKENAALEWEIAALEQGG (SEQ ID NO: 45); and
GEIAALEQKAALKY KNAALKK KIAALKQ GG (SEQ ID NO: 46).

In some embodiments of any one of the aspects as described herein, the coiled-coil peptide linked to the C-terminus of the antibody polypeptide chain, e.g., heavy chain comprises an amino acid sequence selected from the group consisting of:

MK(LKKIKSV)$_4$VGER (SEQ ID NO: 1), LKKIKSV LKKIKSV LKKIKSV LKKIKSV (SEQ ID NO: 5), and CYGGKVSALKEKVSAL-KEEVSANKEKVSALKEKVSALKE (SEQ ID NO. 9).

In some embodiments of any one of the aspects as described herein, the coiled-coil peptide is linked to the C-terminus of the polypeptide via a peptide linker. In some embodiments of any one of the aspects as described herein, the linker linking the polypeptide of the antibody and the coiled-coil peptide comprises a recognition amino acid sequence for a peptide ligase, optionally, the linker comprises a Sortase A recognition sequence. In some embodiments of any one of the aspects described herein, the linker linking the polypeptide of the antibody and the coiled-coil peptide comprises the amino acid sequence LPXTG (SEQ ID NO: 47), optionally, the linker comprises the amino acid sequence LPETG (SEQ ID NO: 48).

In some embodiments of any one of the aspects described herein, the linker linking the polypeptide of the antibody and the coiled-coil peptide comprises the amino acid sequence LPXTGGGGG (SEQ ID NO: 49), optionally, the linker comprises the amino acid sequence LPETGGGGG (SEQ ID NO: 50).

It is noted any antibody known in the art can be modified to link it on its C-terminus with a coiled-coil peptide as described herein. The antibody can be a human or humanized antibody. The antibody can a monoclonal or polyclonal antibody. Exemplary antibodies include, but are not limited to, anti-GPR87 antibody (331CL) and anti-DEspR antibody (7c5).

In another aspect, provided herein is an antibody conjugate. The antibody conjugate comprises: (i) an antibody, where a polypeptide chain, e.g., heavy chain of the antibody linked on its C-terminus to a coiled-coil peptide; and (ii) a coiled-coil peptide linked/conjugated with a payload molecule, e.g., ligand, and wherein the ligand conjugated coiled-coil peptide forms a heterodimer with the coiled-coil peptide linked to polypeptide of the antibody.

In some embodiments of any one of the aspects as described herein, the coiled-coil peptide conjugated with the ligand comprises an amino acid sequence selected from the group consisting of: SEQ ID NOs: 1-46. For example, the coiled-coil peptide conjugated with the ligand comprises the amino acid sequence MK(LEEIVXE)$_4$VGER where each X is independently serine, tyrosine, or a N-ε-azido lysine (SEQ ID NO: 2); MK(LEEIVSE)$_2$LEEIV(K-azido)ELEE-IVYEVGER, where K-azido is N-ε-azido lysine (SEQ ID NO: 3); LEEIVSE LEEIVSE LEEIVSE LEEIVSE (SEQ ID NO: 7), or LEEIVSE LEEIVSE LEEIVKE LEEIVYE (SEQ ID NO: 8). In some embodiments of any one of the aspects described herein, the coiled-coil peptide conjugated with the ligand comprises the amino acid sequence MK(LEEIVSE)$_2$LEEIV(K-azido)ELEEIVYE VGER, where K-azido is N-ε-azido lysine (SEQ ID NO: 3).

In some embodiments of any one of the aspects described herein, the coiled-coil peptide conjugated with the ligand comprises the amino acid sequence MK-LEEIVSE-LEEIVSE-LEEIV(X$^1$)E-LEEIVYE-VGER (SEQ ID NO: 51) or SPEDEIQALEEENAQLEQENAALEEE LAQLEYGX$^1$K-azidoG (SEQ ID NO: 52), where X$^1$ is lysine linked at N-ε position with —X$^2$-L, where X$^2$ is a linker and L is a ligand. Exemplary ligands include small organic and inorganic molecules, amino acids, peptides, polypeptides, peptidomimetics, glycoproteins, lectins, nucleosides, nucleotides, monosaccharides, disaccharides, trisaccharides, oligosaccharides, polysaccharides, lipopolysaccharides, vitamins, steroids, hormones, and cofactors.

The ligand can be a therapeutic agent (e.g., an anti-cancer agent), a diagnostic or imaging agent (e.g., a detectable label).

In some embodiments of any one of the aspects as described herein, the ligand is linked to the peptide via a linker comprising a cleavable linking group.

In another aspect, provided herein is a pharmaceutical composition comprising a polypeptide, coiled-coil peptide and/or a conjugate, e.g., antibody conjugate described herein and a pharmaceutically acceptable carrier.

In yet in another aspect, provided herein is method for preparing a polypeptide linked on its C-terminus to a coiled-coil peptide. The method comprises: contacting a polypeptide comprising on its C-terminus a recognition amino acid sequence for a peptide ligase with a coiled-coil peptide in the presence of a peptide ligase under conditions under conditions wherein the peptide ligase catalyzes the formation of a peptide bond between N-terminus of the coiled-coil peptide and C-terminus of an amino acid in the recognition amino acid sequence.

In some embodiments of the method for preparing the polypeptide recognition amino acid sequence is linked at its C-terminus to an affinity tag. For example, the polypeptide comprises the amino acid sequence LPXTG-X$^T$ (SEQ ID NO. 53) where X$^T$ is an affinity tag, at its C-terminus.

In one non-limiting example, the polypeptide comprises the amino acid sequence LPETG-X$^T$ (SEQ ID NO. 54) where X$^T$ is an affinity tag, at its C-terminus.

In some embodiments of any one of the aspects as described herein, the peptide comprises the amino acid sequence GGGGG (SEQ ID NO. 55) at its N-terminus.

In still another aspect, provided herein is a method of delivering at least one ligand to a cell. The method comprises providing to the cell an antibody conjugate of any of the preceding claims.

In another aspect, provided herein is a method for treating a disease or disorder. The method comprises administering a conjugate described herein to a subject in need thereof, wherein the conjugate comprises a ligand, e.g., a therapeutic agent useful for treating the disease or disorder.

BRIEF DESCRIPTION OF THE DRAWINGS

FIGS. 1A and 1B are SDS-PAGE gels of reduced native antibodies and antibodies modified according to some embodiments of the disclosure. FIG. 1A shows SDS-PAGE gel of the reduced native αGPR87 Ab (331CL) or the modified Ab (331CL-CCK), showing a shift in the heavy chain but not the light chain. FIG. 1B demonstrates similar results seen for the 7c5 Ab and 7c5-CCK antibody, produced via sortase conjugation.

FIG. 2 is a RP-HPLC chromatogram of an unconjugated coiled-coil peptide (CCE) and conjugated with a fluorophore (CCE-AF647) at 220 nm (peptide bond absorbance) and 648 nm (AF647 absorbance). A shift in retention time is observed for the conjugated CCE-AF647 peptide.

FIG. 3 are size exclusion chromatograms (SECs) demonstrating the formation of the AFC, specifically the association of the CCE-AF647 peptide with the Ab-CCK and not the native Ab. Shown are the absorbances at 280 nm (aromatic residues in proteins) and 650 nm (AF647).

FIGS. 4A-4D are size exclusion chromatograms of some embodiments of the disclosure. FIG. 4A shows the SEC of Ab-CCK compared to native Ab. FIG. 4B shows the SEC of AFC and multiple populations seen in comparison to native Ab. FIG. 4C shows the SEC of AFC when different equivalents of CCE-AF647 to Ab-CCK. FIG. 4D shows the SEC of AFC under different buffer and incubation temperature conditions. CP-PBS is a 1:1 mixture of citrate phosphate buffer and PBS. RT is room temperature.

FIGS. 7A-7C are UV-Vis analysis of DBCO reactions at 310 nm between CCE and DBCO-MMAE (FIG. 7A), between CCE and DBCO-AF647 (FIG. 7B) and between CCE and DBCO-PEG (FIG. 7C).

FIGS. 9A-9D are SEC chromatograms of some embodiments of the disclosure. FIG. 9A is a SEC chromatogram of Ab-CCK at 280 nm (aromatic residues of antibody) and 248 nm. FIG. 9B is a SEC chromatogram of ADC demonstrating the different populations that arise and signal at 248 nm (MMAE). FIG. 9C shows an ELISA based binding analysis of native Ab compared to Ab-CCK and ADCs prepared at both room temperature (RT) and 50° C. when analyzed by wt/vol.

FIG. 9D shows an analysis of FIG. 9C when taking into account the hexamer and timer formations of both Ab-CCK and ADCs and analyzing by molarity.

FIGS. 13A-13E are graphs showing cytotoxicity of an exemplary ADC of the disclosure equivalent MMAE and Ab in NCI-H358 (FIG. 13A), in NCI-H520 (FIG. 13B), in NHLF (FIG. 13C), in BEAS-2B (FIG. 13D) and in HUVEC (FIG. 13E) cell lines over 48 and 72 hours of incubation.

FIG. 14 is a table summarizing the IC$_{50}$ values for the various cell lines as calculated from FIGS. 13A-13E at 48 and 72 hours of incubation with either the ADC or MMAE. IC$_{50}$ values are expressed as ng/ml of MMAE.

FIGS. 15A and 15B are graphs showing the cytotoxicity of ADC in NCI-H520 cell line after incubation for 48, 72, and 168 hours (one week) (FIG. 15A) and in NCI-H358 cell line after incubation for 48, 72, and 120 hours (FIG. 15B).

FIG. 16 is a table showing the AUC values for the various cell lines as calculated from FIGS. 13A-13E at 48 and 72 hours of incubation with either the ADC or MMAE. AUC values are expressed as percentage of theoretical 100% viability.

FIGS. 20A-20D are bargraphs showing intact AFC concentration in plasma (FIG. 20A), total antibody plasma concentrations following AFC injection (FIG. 20B), intact AFC levels in tumor and major organs (FIG. 20C) and total antibody levels in tumor and major organs following AFC injection (FIG. 20D).

FIG. 24A-24C show the $^1$H NMR spectra (FIG. 24A), MALDI spectrum showing the expected molecular weight (Expected 1729.09, observed 1751.717 [M+Na]) (FIG. 24B) and HPLC chromatogram showing high purity (FIG. 24C) of the exemplary linker structure (DBCO-MMAE) shown in FIG. 22

DETAILED DESCRIPTION

Figure 5:
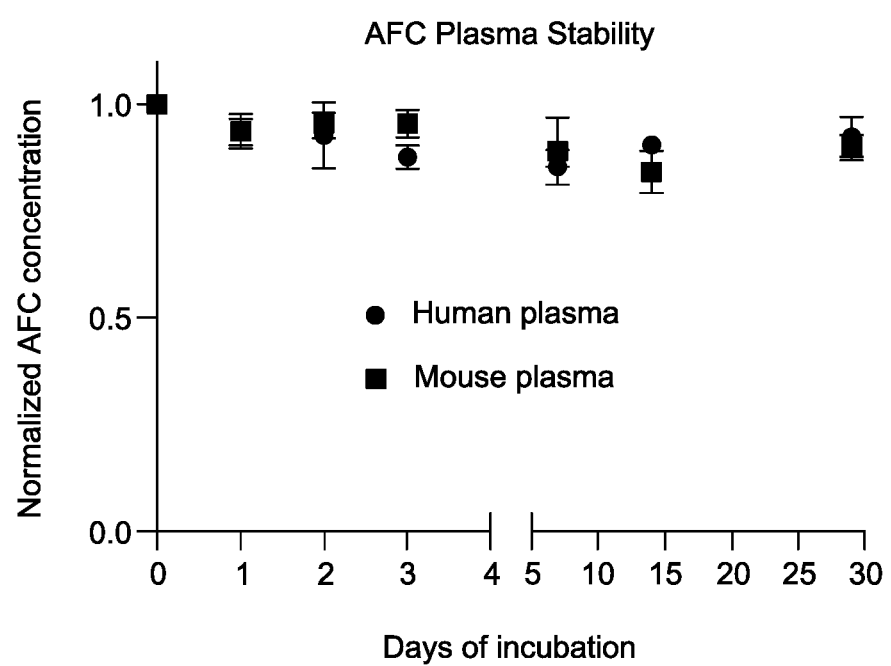
FIG. 5 depicts the stability of AFC over four weeks of incubation at 37° C. at 10 µg/ml in either human or Balb/c mouse plasma. Concentrations normalized to day 0 concentration for each sample.

It is to be understood that both the foregoing general description and the following detailed description are exemplary and explanatory only and are not restrictive of the invention, as claimed.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Embodiments of the technology as described herein involve improvements upon compositions and methods involving antibody conjugates, e.g., antibody drug conjugates (ADCs).

Polypeptide—Coiled-Coil Peptide

In one aspect, provided herein is a polypeptide linked on its C-terminus to a coiled-coil peptide. The coiled-coil peptide is capable of forming a heterodimer with another coiled-coil peptide.

As used herein, a "coiled-coil peptide" is a peptide comprising an amino acid sequence that form a thermodynamically stable, alpha-helical, parallel bundle of helices by spontaneous self-association. The coiled-coil peptide are peptides based on canonical tandem heptad sequence repeats, also referred to as "coiled coil peptide chain segments" herein, that form right handed amphipathic C-helices, which then assemble to form helical bundles with left-handed supercoils. Generally, the coiled-coil peptide comprises at least two coiled coil peptide chain segments. Coiled coil peptide can contain multiple repeat units, typically and preferably consecutively linked to each other. The repeat units of the coiled coil peptide as an insertion, deletion or exchange of at least one, preferably exactly 1, 2, 3 or 4 amino acids within the repeat unit. Also included are peptides built from non-canonical, non-heptad-based repeats that form coiled-coils that are not necessarily left-handed or even regular Supercoils.

Coiled-coil designs are known in the art. See, for example, PCT Publication No. WO1997012988; PCT Publication No. WO 1995031480; Woolfson, D. N., Adv. Prot. Chem., 2005, 70, 79-112; Parry, D. A. D., et al, Advances in Protein Chemistry, 2005, 70; and Litowski, J. et al., J. Biol. Chem. 2002, 277(40). 37272-37279, contents of all of which are incorporated herein by reference in their entireties. Exemplary coiled-coil peptide amino acid sequences include, but are not limited to SEQ ID NOs: 1-46.

The term "peptide" refers to a polymer of amino acids, or amino acid analogs, regardless of its size or function. In some embodiments, the term "peptide" refers to small polypeptides, e.g., a polymer of about 15-25 amino acids.

In some embodiments of any one of the aspects described herein, the coiled-coil peptide linked to the polypeptide is the CCK, peptide, i.e., the coiled-coil peptide comprises the amino acid sequence: LKKIKSV LKKIKSV LKKIKSV LKKIKSV (SEQ ID NO: 5). For example, the coiled-coil peptide comprises the amino acid sequence: MK(LKKISV)$_4$VGER (SEQ ID NO: 1).

It is noted that the coiled-coil peptide can be linked directly to the C-terminus of the polypeptide, e.g., via a peptide bond between the C-terminus of the polypeptide and the N-terminus of the coiled-coil peptide. Alternatively, the coiled-coil peptide can be linked to the C-terminus of the polypeptide via a linker.

In some embodiments of any of the aspects, the linker used to link the polypeptide with the coiled-coil peptide is a flexible linker.

In some embodiments of the various aspects described herein, the polypeptide and the coiled-coil peptide are linked via a cleavable linker.

In some embodiments of the various aspects described herein, the polypeptide and the coiled-coil peptide are linked via a peptide linker.

In some embodiments of any one of the aspects described herein, the polypeptide and the coiled-coil peptide are linked via a peptide linker, wherein the linker comprises an amino acid sequence recognized by a peptide ligase, i.e., a recognition amino acid sequence for a peptide ligase. For example, the polypeptide and the coiled-coil peptide are linked via a peptide linker, wherein the linker comprises an amino acid sequence by a sortlase (e.g., Sortlase A, Sortlase B, Sortlase C or Sortlase D). Accordingly, in some embodiments of any one of the aspects described herein, the polypeptide and the coiled-coil peptide are linked via a peptide linker, and wherein the linker comprises the amino acid sequence LPXTG (SEQ ID NO: 47), where X is any amino acid. For example, the polypeptide and the coiled-coil peptide are linked via a peptide linker, and wherein the linker comprises the amino acid sequence LPETG (SEQ ID NO: 48). In some embodiments of any one of the aspects described herein, the polypeptide and the coiled-coil peptide are linked via a peptide linker, and wherein the linker comprises the amino acid sequence LPXTGGGGG (SEQ ID NO: 49), where X is any amino acid. For example, the polypeptide and the coiled-coil peptide are linked via a peptide linker, and wherein the linker comprises the amino acid sequence LPETGGGGG (SEQ ID NO: 50).

In some embodiments of any one of the aspects described herein, the polypeptide and the coiled-coil peptide are linked via a peptide linker, wherein the linker comprises an amino acid sequence recognized by Butelase 1. Thus, in some embodiments of any one of the aspects described herein, the polypeptide and the coiled-coil peptide are linked via a peptide linker, and wherein the linker comprises the amino acid sequence D/N-X, where X is any amino acid residue. For example, the polypeptide and the coiled-coil peptide are linked via a peptide linker comprising the amino acid sequence D/N-GI.

In some embodiment of any one of the aspects described herein, the polypeptide and the coiled-coil peptide are linked via a peptide linker, wherein the linker comprises an amino acid sequence recognized by Trypsiligase. Thus, in some embodiments of any one of the aspects described herein, the polypeptide and the coiled-coil peptide are linked via a peptide linker, and wherein the linker comprises the amino acid sequence Y-RH.

In some embodiments of any one of the aspects described herein, the polypeptide and the coiled-coil peptide are linked via a non-peptide linker. For example, the polypeptide and the coiled-coil peptide are linked via a linker comprising ethylene glycol, e.g., PEG-3, PEG-4, PEG-4, PEG-5 or PEG-6.

Antibodies

In some embodiments of any one of the aspects described herein, the polypeptide linked at its C-terminus to the coiled-coil peptide is one of the chain of an antibody. For example, the polypeptide linked at its C-terminus to the coiled-coil peptide is a heavy chain of an antibody. Accordingly, in another aspect, provided herein is an antibody where a heavy chain of the antibody is linked at its C-terminus to the coiled-coil peptide.

As used herein an "antibody" refers to IgG, IgM, IgA, IgD or IgE molecules or antigen-specific fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

Generally, the antibody includes at least one immunoglobulin variable domain or immunoglobulin variable domain sequence and which specifically binds a given antigen. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized. In some embodiments, binding described herein can be preferential binding, e.g., binding between two molecules, compounds, cells and/or particles wherein the first entity binds to the second, target entity with at least 2 times greater specificity and affinity than it binds to a third entity which is a non-target.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody as described herein. Such functional activities include, e.g. the ability to bind to a target.

The antibody linked to the coiled-coil peptide can be a monoclonal antibody, a chimeric antibody, a CDR-grafted antibody, a human antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and/or a bispecific antibody.

In some embodiments of any one of the aspects described herein, the antibody is a monoclonal antibody.

In some embodiments of any one of the aspects described herein, the antibody is a human antibody or humanized antibody. For example, the antibody is a human or humanized monoclonal antibody.

Antibodies are well known in the art and amenable to linking with a coiled-coil peptide as described herein.

In some embodiments of any one of the aspects described herein, the antibody binds a cell polypeptide, e.g., cell surface receptor overexpressed in a disease or disorder. For example, the antibody binds a polypeptide, e.g., cell surface receptor overexpressed in cancer. Exemplary cell receptors that are overexpressed in cancer include, but are not limited to, G protein coupled receptors (GPCRs), epidermal growth factor receptor (EGFR), VEGF, integrins, folate receptors (FRs), transferrin receptors (TIRs), fibroblast growth factor receptors (FGFRs), sigma receptors (SRs), folic stimulating hormone receptors (FSHRs), biotin receptors (BRs), C-type lectin receptors (CLRs), asialoglycoprotein receptor (ASGPR) and NRP-1. Accordingly, in some embodiments of any one of the aspects described herein, the antibody binds to a GPCR, EGFR, VEGF, folate receptor, transferrin receptor, fibroblast growth factor receptor, sigma receptor, folic stimulating hormone receptor, biotin receptor, C-type lectin receptor, ASGPR or NRP-1.

G-protein coupled receptor 87 (GPR87) is a protein in humans encoded by the GPR87 gene. G-protein coupled receptors are important in cell growth and survival, metastasis, and drug resistance. Overexpression of GPR87 has been reported in many malignant tumors. Thus, in some embodiments of any one of the aspects described herein, the antibody is an anti-GPR87 antibody or an antigen binding fragment thereof. Exemplary αGPR87 antibodies are commercially available and include, but are not limited to, Afuco™ Anti-Human GPR87 ADCC Recombinant Antibody, ADCC Enhanced (CAT #: AFC-317CL, Creative Biolabs, Shirley, NY); Anti-Human GPR87 Recombinant Antibody (CAT #: TAB-331CL, Creative Biolabs, Shirley, NY) and Anti-Human GPR87 Therapeutic Antibody (C0812) (CAT #TAB-002CT, Creative Biolabs, Shirley, NY). Exemplary heavy chain and light chain amino acid sequences for anti-αGPR87 antibodies include, but are not limited to, EFAATMHSSALLC-CLVLLTGVRAEVQLQQSGPDLVKPGASMKISCK-ASGYSFTDYTMH WVKQSHGKNFEWIGLINPYNDGT-TYNQKFKGKATLTVDKSSSTAYMELLSLTSEDSAV YYCASLDYWGQGTSVTVSSAKTTPPSVY-PLAPGSAAQTNSMVTLGCLVKGYFPEPVTV TWNSGSLSSGVHTFPAVLQSDLYTLSSSVTVPSSTWPSETVTCNVAHPASSTKVDKKIVP RDCGCKPCICTVPEVSSVFIFPPKPKDVLTITLTPKVTCVVVDISKDDPEVQFSWFVDDVE VHTAQTQPREEQFNSTFRSVSELPIMHQDWLNGKEFKCRVNSAAFPAPIEKTISKTKGRP KAPQVYTIPPPKEQMAKDKVSLTCMITDFFPEDITVEWQWNGQPAENYK NTQPIMDTD GSYFVYSKLNVQKSNWEAGNTFTCSVLHEGLHNHHTEKSLSHSPGK (heavy chain, SEQ ID NO: 72) and NTTHYRETQAG*RLNGPSRLERPPLCWISAEFAATMHSSALLCCLVLLTGVRADVVMTQ TPL SLPVSLGDQASISCRSSQSLVHSSGN-TYLHWYLQKPGQSPKLLIYKVSNRFSGVPDR FSGSGSGTDFTLKISRVEAEDLGVYFCSQSTHVPY-TFGGGTKLEIKRADAAPTVSIFPPSS EQLTSGGASVVCFLNNFYPKDINVKWKIDGSERQNGVLNSWTDQDSKDSTYSMSSTLT LTKDEYERHNSYTCEATHKTSTSPIVKSFNRNEC (light chain, SEQ ID NO: 73)

Dual-endothelin 1/VEGFsp receptor (DEspR, formerly DEAR) is also known as FBXW7 antisense RNA 1. It is functionally coupled to a calcium-mobilizing transduction system, responding equivalently to both endothelin-1/EDN1 and angiotensin-2 peptides in a highly specific manner. DEspR can play a role in angiogenesis, cardiovascular, and neural development. Thus, in some embodiments of any one of the aspects described herein, the antibody is an anti-DEspR antibody or an antigen binding fragment thereof. Exemplary anti-DEspR antibodies are commercially available and include, but are not limited to, Anti-Human DEspR Recombinant Antibody (Hu7C5B2) (Cat. No. TAB-191MZ, Creative Biolabs, Shirley, NY); Human Anti-DEspR Recombinant Antibody (HPAB-2092LY) (Cat. No. HPAB-2092LY, Creative Biolabs, Shirley, NY) and Anti-Human DEspR Therapeutic Antibody (Cat. No. TAB-213CL, Creative Biolabs, Shirley, NY). Exemplary heavy chain and light chain amino acid sequences for anti-DEspR antibodies include, but are not limited to, EFAATMHSSALLCCLVLLTGVRAQVQLKESGPGLVAPSQSLSITCTVSGFSLTSYDISWIR QPPGKGLEWLGVIW TGGGTNYNSAFMSRLSISKDNSKSQVFLKMNSLQTDDTAIYYCV RDRDYDGWYFDVWGAGTTVTVSSAKTTPPSVYPLAPGCGDTTGSSVTLGCLVKGYFPE SVTVTWNSGSLSSSVHTFPALLQSGLYTMSSSVTVPSSTWPSQTVTCSVAHPASSTTVDK KLEPSGPISTINPCPPCKECHKCPAPNLEGGPSVFIFPPNIKDVLMISLTPKVTCVVVDVSE DDPDVQISWFVNNVEVHTAQTQTHREDYNSTIRVVSTLPIQHQDWMSGKEFKCKVNNK DLPSPIERTISKIKGLVRAPQVYILPPPAEQLSRKDVSLTCLVVGFNPGDISVEWTSNGHTE ENYKDTAPVLSDSDGSYFIYSKLNMKTSKWEKTDSF SCNVRHEGLKNYYLKKTISRSPGKD (heavy chain, SEQ ID NO: 74) and EFAATMHSSALLCCLVLLTGVRADVLMTQTPLSLPVSLGDQASISCRSSQSIVHSNGNTY LEWYLQKPGQSPKLLIYKVSNRFSGVPDRFSGSGSG TDFTLKISRVEAEDLGVYYCFQGS HVPYTFGGGTKLEIKRADAAPTVSIFPPSSEQLTSGGASVVCFLNNFYPKDINVKWKIDG SERQNGVLNSWTDQDSKDSTYSMSSTLTLTKDEYERHNSYTCEAT HKTSTSPIVKSFNR NECD (light chain, SEQ ID NO: 75)

In some embodiments of any one of the aspects described herein, the antibody is an anti-HER2 antibody. Exemplary heavy chain and light chain amino acid sequences for anti-DEspR antibodies include, but are not limited to, MHS-SALLCCLVLLTGVRAEVQLVESGGGLVQPGGSLRL SCAASGFNIKDTYIHWVRQAP GKGLEW-VARIYPTNGYTRYADSVKGRFTISADT SKNTAYLQMNSLRAEDTAVYYCSRW GGDGFYAMDYWGQGTLVTVSSASTKGPSVFPLAPSSKSTSGGTAALGCLVKDYFPEPV TVSWNSGALTSGVHTFPAVLQ SSGLYSLSSVVTVPSSSLGTQTYICNVNHKPSNTKVDK KVEPKSCDKTHTCPPCPA-PELLGGPSVFLFPPKPKDTLMISRTPEVTCVVVDVSH EDPEV KFNWYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNGQPEN NYKTTPPVLDSDGSFFLYSKLTVDKSRWQQGNVF SCSVMHEALHNHYTQKSLSLSPG*GD (heavy chain, SEQ ID NO: 76) and MHSSALLCCLVLLTGVRADIQMTQSPSSLSASVGDRVTITCRASQDVNTAVAWYQQKP GKAPKLLIYSASFLYSGVPSRFSGSRSGTDFTLTISSLQPEDFATYYCQQHY TTPPTFGQG TKVEIKRTVAAPSVFIFPPSDEQLKSGTASVVCLLNNFYPREAKVQWKVDNALQSGNSQ ESVTEQDSKDSTYSLSSTLTLSKADYEKHKVYACEV THQGLSSPVTKSFNRGECD (light chain, SEQ ID NO: 77)

In some embodiments of any one of the aspects described herein, the antibody is an anti-EGFR antibody. Exemplary anti-EGFR antibodies include, but are not limited to, Recombinant Anti-EGFR (phospho Y1068) antibody [EP774Y](Cat. No. ab40815, abcam, Cambridge, UK); Anti-EGFR antibody [EP38Y](Cat. No. ab52894, abcam, Cambridge, UK); Anti-EGFR antibody [13/EGFR](Cat. No. ab289889, abcam, Cambridge, UK); EGFR Monoclonal Antibody (H11) (Cat. No. MA5-13070, Invitrogen, Waltham, MA); EGFR Monoclonal Antibody (111.6) (Cat. No. MA5-13269, Invitrogen, Waltham, MA); EGFR Mouse Monoclonal Antibody [Clone ID: OTI2G8](Cat. No. TA506209, OriGene, Rockville, MD). Exemplary sequences of anti-EGFR antibodies include, but are not limited, to those disclosed in PCT publication WO2011156617, content of which is incorporated herein by reference in its entirety.

In some embodiments of any one of the aspects described herein, the antibody is an anti-folate receptor antibody. Exemplary anti-bodies that can bind the folate receptor include, but are not limited to, Folate Receptor alpha Monoclonal Antibody (548908) (Cat. No. MA5-23917, Invitrogen, Waltham, MA); Folate Receptor alpha Monoclonal antibody (C2) (Cat. No. MA5-43815, Invitrogen, Waltham, MA); FOLR Monoclonal Antibody (2B4B7) (Cat. No. 60307-1-IG, Proteintech, Rosemont, IL). Exemplary sequences of anti-folate receptor antibodies include, but are not limited, to those disclosed in PCT publication WO2013012722, content of which is incorporated herein by reference in its entirety.

In some embodiments of any one of the aspects described herein, the antibody is an anti-fibroblast growth factor receptor antibody. Exemplary anti-bodies that can bind a fibroblast growth factor receptor include, but are not limited to, Anti-Fibroblast Growth Factor-Basic antibody, Mouse monoclonal (FB-8) (Cat. No. F6162-.2ML, Millipore Sigma, Burlington, MA); Monoclonal Anti-Fibroblast Growth Factor-Basic antibody produced in mouse (10060) (Cat. No. F5305-500UG, Millipore Sigma, Burlington, MA). Exemplary sequences of anti-fibroblast growth factor receptor antibodies include, but are not limited, to those disclosed in U.S. Pat. No. 8,101,721, content of which is incorporated herein by reference in its entirety.

In some embodiments of any one of the aspects described herein, the antibody is an anti-transferrin receptor antibody. Exemplary anti-bodies that can bind the transferrin receptor include, but are not limited to, Transferrin Recombinant Rabbit Monoclonal Antibody (101) (Cat. No. MA5-30565, Invitrogen, Waltham, MA); Transferrin Monoclonal Antibody (12A6) (Cat. No. MA1-20106, Invitrogen, Waltham, MA); Transferrin Monoclonal Antibody (2B4C6) (Cat. No. 66171-1-IG, Proteintech, Rosemont, IL); TF Monoclonal Antibody (OTI5G2), TrueMAB™ (Cat. No. CF500848, OriGene, Rockville, MD); TF Monoclonal Antibody (1C2) (Cat. No. H00007018-M08, Abnova, Taipei, Taiwan, CN). Exemplary sequences of anti-transferrin receptor antibodies include, but are not limited, to those disclosed in U.S. Pat. No. 7,572,895, content of which is incorporated herein by reference in its entirety.

In some embodiments of any one of the aspects described herein, the antibody is an anti-sigma receptor antibody. Exemplary anti-bodies that can bind the sigma receptor include but are not limited to, Anti-Sigma Receptor Antibody (B-5) (Cat. No. sc-137075, Santa Cruz Biotechnologies, Santa Cruz, CA); Anti-Sigma Receptor Antibody (F-5) (Cat. No. sc-166392, Santa Cruz Biotechnologies, Santa Cruz, CA). Exemplary sequences of anti-sigma receptor antibodies include, but are not limited, to those disclosed in U.S. Pat. No. 10,800,844, content of which is incorporated herein by reference in its entirety.

In some embodiments of any one of the aspects described herein, the antibody is an anti-folic stimulating hormone receptor antibody. Exemplary anti-bodies that can bind the folic stimulating hormone receptor include, but are not limited to, Follicle Stimulating Hormone Monoclonal Antibody (P2B4) (Cat. No. MA5-14711, Invitrogen, Waltham, MA); Follicle Stimulating Hormone Monoclonal Antibody (1G6D12) (Cat. No. MIF2701, Invitrogen, Waltham, MA); Follicle Stimulating Hormone Monoclonal Antibody (P4G2) (Cat. No. MIF2709, Invitrogen, Waltham, MA); FSHB Monoclonal Antibody (OTI4E8), TrueMAB™ (Cat. No. TA600097, OriGene, Rockville, MD); FSHB Monoclonal Antibody (OTI2A6), TrueMAB™ (Cat. No. CF501581, OriGene, Rockville, MD); FSH Monoclonal Antibody (FB2) (Cat. No. 603-171, AbboMax, San Jose, CA); FSH Monoclonal Antibody (1038) (Cat. No. MUB0608S, MUbio, Susteren, Netherlands). Exemplary sequences of anti-folic stimulating hormone receptor antibodies include, but are not limited, to those disclosed in European Patent Publication No. EP0328248, content of which is incorporated herein by reference in its entirety.

In some embodiments of any one of the aspects described herein, the antibody is an anti-VEGF antibody. Exemplary anti-VEGF antibodies include, but are not limited to, VEGF Monoclonal Antibody (JH121) (Cat. No. MA5-13182, Invitrogen, Waltham, MA); VEGF Monoclonal Antibody (VG1) (Cat. No. MA-5-12184, Invitrogen, Waltham, MA); VEGF Monoclonal Antibody (16F1) (Cat. No. M808, Invitrogen, Waltham, MA); VEGF Recombinant Rabbit Monoclonal Antibody (SP07-01) (Cat. No. MA5-32038, Invitrogen, Waltham, MA); VEGF Monoclonal Antibody (OTI4E3), TrueMAB™ (Cat. No. TA500289, OriGene, Rockville, MD); VEGF Monoclonal Antibody (OTI4G3), TrueMAB™ (Cat. No. TA5000042, OriGene, Rockville MD). Exemplary sequences of anti-VEGF antibodies include, but are not limited, to those disclosed in U.S. Pat. No. 8,101,177, content of which is incorporated herein by reference in its entirety In some embodiments of any one of the aspects described herein, the antibody is an anti-biotin receptor antibody. Exemplary anti-bodies that can bind the biotin receptor include, but are not limited Avi Tag Monoclonal Antibody (1D11D10) (Cat. No., A01738-40, GenScript, Piscataway, NJ); Avi Tag Antibody (Cat. No. MAB10546, R&D Systems, Minneapolis, MN); AVI Tag Monoclonal Antibody (Cat. No. LS-C387443, LifeSpan BioSciences, Seattle, WA); Avi-Tag (8F3) Monoclonal Antibody (Cat. No. bsm-3164M, Bioss, Woburn, MA); Mouse Anti-Avi-tag Recombinant Antibody (6D8-1G7-2C3) (Cat. No. CBMAB-Z0078-LY, Creative Biolabs, Shirley, NY).

In some embodiments of any one of the aspects described herein, the antibody is an anti-C-lectin receptor antibody. Exemplary anti-bodies that can bind the C-lectin receptor include, but are not limited to, CLEC1A mouse monoclonal antibody, clone OTI1H8 (Cat. No. TA809213, OriGene, Rockville, MD); Anti-CLEC-2 antibody [AYP1](Cat. No. ab288665, abcam, Cambridge, UK); Monoclonal Mouse anti-Human CLEC4D/MCL Antibody (APC, aa52-215) (Cat. No. LS-C128189, LSBio, Seattle, WA); CLEC5A Monoclonal Antibody (283834) (Cat. No. MA5-23909, Invitrogen, Waltham, MA); CD368 (Clec6) Monoclonal Antibody (9B9), eFluor™ 660, eBioscience™ (Cat. No. 50-9113-42, Invitrogen, Waltham, MA); CD369 (Clec7a, Dectin-1) Monoclonal Antibody (15E2), PE, eBioscience™ (Cat. No. 12-9856-42, Invitrogen, Waltham, MA); CD370 (Clec9A) Monoclonal Antibody (9A11), PE, eBioscience™ (Cat. No. 12-3709-42, Invitrogen, Waltham, MA); CLEC10A Monoclonal Antibody (OTI2B10), TrueMAB™ (Cat. No. CF810180, OriGene, Rockville, MD); SCGF Monoclonal Antibody (4H11E4) (Cat. No. 60295-1-IG, Proteintech, Rosemont, IL); CLEC12A Monoclonal Antibody (687317) (Cat. No. MA5-24312, Invitrogen, Waltham, MA); CLEC14A Recombinant Rabbit Monoclonal Antibody (36) (Cat. No. MA5-31077, Invitrogen, Waltham, MA); KLRG1 Monoclonal Antibody (13F12F2), PE, eBioscience™ (Cat. No. 12-9488-42, Invitrogen, Waltham, MA). Exemplary sequences of anti-C-lectin receptor antibodies include, but are not limited, to those disclosed U.S. Pat. No. 9,751,933, content of which is incorporated herein by reference in its entirety.

In some embodiments of any one of the aspects described herein, the antibody is an anti-ASGPR antibody. Exemplary anti-bodies that can bind ASGPR include, but are not limited to, Human ASGR1/ASGPR1 Antibody, (Cat. No. MAB4394-SP, R&D Systems, Minneapolis, MN); R718 Mouse Anti-Human ASGPR 1 (Cat. No. 752137, BD Biosciences, East Rutherford, NJ); ASGPR, Rat, mAb 8D7 (Cat. No. HM3020, Hycult Biotech, Plymouth Meeting, PA); Mouse Anti-ASIALOGLYCOPROTEIN RECEPTOR Antibody (Cat. No. A8510-100ug, United States Biological, Swampscott, MA). Exemplary sequences of anti-ASGPR antibodies include, but are not limited, to those disclosed PCT Publication No. WO2014023709, content of which is incorporated herein by reference in its entirety.

In some embodiments of any one of the aspects described herein, the antibody is an anti-NPR-1 antibody. Exemplary anti-NPR-1 antibodies include, but are not limited to, CD304 (Neuropilin-1) Monoclonal Antibody (XML1Y1), eBioscience™ (Cat. No. 14-3042-82, Invitrogen, Waltham, MA); CD304 (Neuropilin-1) Recombinant Rabbit Monoclonal Antibody (ST05-30) (Cat. No. MA5-32179, Invitrogen, Waltham, MA); Neuropilin-1 Monoclonal Antibody (49H9)

(Cat. No. BSM-52479R, Bioss, Woburn, MA); NRP1 Monoclonal Antibody (3G6-2C5) (Cat. No. H00008829-M01, Abnova, Taipei, Taiwan, CN). Exemplary sequences of anti-ASGPR antibodies include, but are not limited to those disclosed US Patent Publication No. US20200123263, content of which is incorporated herein by reference in its entirety.

Coiled-Coil Peptide—Payload Conjugate

In another aspect provided herein is a coiled-coil peptide, wherein the coiled-coil peptide is covalently linked to a payload molecule, e.g., a ligand. The payload molecule, e.g., the ligand can be selected from small organic and inorganic molecules, amino acids, peptides, polypeptides, peptidomimetics, glycoproteins, lectins, nucleosides, nucleotides, monosaccharides, disaccharides, trisaccharides, oligosaccharides, polysaccharides, lipopolysaccharides, vitamins, steroids, hormones, and cofactors. For example, the ligand can be a therapeutic agent, diagnostic agent, imaging agent or a detectable label.

It is noted that the ligand can be attached to the coiled-coil peptide at any position in the peptide. For example, the ligand can be linked to an amino acid residue at the N-terminus of the coiled-coil peptide. In some other non-limiting examples, the ligand can be linked to an amino acid residue at the C-terminus of the coiled-coil peptide. In yet some other example, the ligand can be linked to an amino acid residue at an internal position of the polypeptide.

The ligand can be linked to the α-amino group, the carboxylic group or the side chain of the amino acid. In some embodiments of any one of the aspects described herein, the ligand is linked to a side chain of an amino acid residue of the coiled-coil peptide.

In some embodiments of any one of the aspects described herein, the ligand is linked to an amino acid reside selected from the group consisting of lysine, arginine, histidine, aspartic acid, glutamic acid, serine, threonine, asparagine, glutamine, cysteine, selenocysteine, methionine, phenylalanine, tyrosine, and tryptophan. For example, the ligand is linked to an amino acid reside selected from the group consisting of lysine, arginine, histidine, aspartic acid, glutamic acid, serine, threonine, asparagine, and glutamine. In some embodiments of any one of the aspects described herein, the ligand is linked to a lysine reside in the coiled-coil peptide. For example, the ligand is linked to the side chain of a lysine residue in the coiled-coil peptide.

In some embodiments of any one of the aspects described herein, the ligand is linked to the amino acid residue of the coiled-coil peptide via a linker. For example, the ligand is linked to the amino acid residue via a cleavable linker.

The coiled-coil peptide linked with a ligand can comprise a coiled-coil peptide amino acid sequence described herein. For Example, the coiled-coil peptide linked with a ligand can comprise an amino acid sequence selected from the group consisting of SEQ ID NOs: 1-46.

In some embodiments of any one of the aspects described herein, the coiled-coil peptide linked with a ligand comprises the amino acid sequence (LEEIVXE)$_4$, where each X is independently serine, tyrosine, or lysine (e.g., N-ε-azido-lysine) (SEQ ID NO: 56). For example, the coiled-coil peptide linked with a ligand comprises the amino acid sequence MK(LEEIVXE)$_4$VGER, where each X is independently serine, tyrosine, or lysine (e.g., N-ε-azido-lysine) (SEQ ID NO: 2).

In some embodiments of any one of the aspects described herein, the coiled-coil peptide linked with a ligand comprises the amino acid sequence (LEEIVSE)$_2$LEEIV(K-azido)ELEEIVYE, where K-azido is N-ε-azido-lysine (SEQ ID NO: 57). For example, the coiled-coil peptide linked with a ligand comprises the amino acid sequence MK(LEEIVSE)$_2$LEEIV(K-azido)ELEEIVYEVGER, where K-azido is 6-azido lysine (SEQ ID NO: 3).

In some embodiments of any one of the aspects described herein, the coiled-coil peptide linked with a ligand comprises the amino acid sequence (LEEIVX$^1$E)$_4$ (SEQ ID NO: 58), where each X$^1$ is independently serine, tyrosine, or lysine linked at the N-ε-position with —X$^2$-L, where X$^2$ is a linker and L is a payload molecule, e.g., a ligand, provided that one X$^1$ is lysine linked at the 6-position with —X$^2$-L. For example, the coiled-coil peptide linked with a ligand comprises the amino acid sequence MK(LEEIVX$^1$E)$_4$VGER (SEQ ID NO: 59).

In some embodiments of any one of the aspects described herein, the coiled-coil peptide linked with a ligand comprises the amino acid sequence (LEEIVSE)$_2$LEEIV(X$^1$)ELEEIVYE (SEQ ID NO: 60), where X$^1$ is lysine linked at the 6-position with —X$^2$-L, where X$^2$ is a linker and L is a payload molecule, e.g., a ligand. For example, the coiled-coil peptide linked with a ligand comprises the amino acid sequence MK(LEEIVSE)$_2$LEEIV(X$^1$)ELEEIVYEVGER (SEQ ID NO: 51) or SPEDEIQALEEENAQLEQENAALEEE LAQLEYGX$^1$K-azidoG (SEQ ID NO: 52).

Antibody-Drug Conjugate/ADC

The coiled-coil peptide linked to the polypeptide and the coiled-peptide can form heteromultimeric structures, e.g., heterodimers with each other. Accordingly, in another aspect provided herein is a conjugate comprising: (i) a coiled-coil peptide linked with a payload molecule, e.g., a ligand; and (ii) a polypeptide linked at its C-terminus with a coiled-coil peptide, where the coiled-coil peptide linked with the payload molecule forms a heterodimer with the coiled-coil peptide linked at the C-terminus of the polypeptide.

As described herein, the polypeptide linked to the coiled-coil peptide can be a chain of an antibody. Thus, in another aspect, provide herein is an antibody conjugate comprising: (i) an antibody comprising at least one antibody chain linked at its C-terminus with a first coiled-coil peptide and (ii) a second coiled-coil peptide linked with a payload molecule, e.g., a ligand, and where the coiled-coil peptide linked with the payload molecule forms a heterodimer with the coiled-coil peptide linked at the C-terminus of the antibody chain.

Linkers

Embodiments of the various aspects described herein include a linker. As used herein, the term "linker" means an organic moiety that connects two parts of a compound, e.g., two chemical moieties. Linkers typically comprise an atom such as oxygen or sulfur, a unit such as NR$^1$, C(O), C(O)O, C(O)NR$^1$, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^L)_2$, C(O), cleavable linking group, substituted or unsubstituted aryl, substituted or unsubstituted heteroaryl, substituted or unsubstituted heterocyclic; where $R^L$ is hydrogen, acyl, aliphatic or substituted aliphatic.

The linker can be a peptide linker containing one or more amino acid residues or a chemical linker. The linker can be a peptide linker. The term "peptide linker" as used herein denotes linker comprising one or more amino acid residues, e.g., a peptide with amino acid sequences, which is in some embodiments of synthetic origin. It is noted that peptide linkers may affect folding of a given polypeptide, and may also react/bind with other proteins, and these properties can be screened for by known techniques. A peptide linker can comprise 1 amino acid or more, 5 amino acids or more, 10 amino acids or more, 15 amino acids or more and beyond. Conversely, a peptide linker can comprise less than 20 amino acids, less than 15 amino acids or less than 10 amino acids.

In some embodiments of the various aspects described herein, the peptide linker comprises from 1 amino acid to about 30 amino acids. For example, the peptide linker can comprise from about 2 amino acids to about 25 amino acids, from about 3 amino acids to 20 amino acids, from about 4 amino acids to 15 amino acids, or from about 5 amino acids to about 10 amino acids.

In some embodiments of the various aspects described herein, the linker comprises, 1, 2, 3, 4, 5, 6, 7, 8, 9, 10, 11, 12, 13, 14 or 15 amino acids. For example, the linker comprises 2, 3, 4, 5, 6, 7, 8, 9 or 10 amino acids.

In some embodiments of any one of the aspects described herein, the linker comprises an amino acid sequence recognized by a peptide ligase, i.e., a recognition amino acid sequence for a peptide ligase. A "peptide ligase" is an enzyme that catalyzes the formation of peptide bonds with site and substrate specificity. Generally, the peptide ligase recognizes a specific amino acid for site-specific ligation, e.g., site-specific bonding of peptides and proteins. Exemplary peptide ligases that recognize amino acid sequences for site-specific bonding include, but are not limited to, Sortase A-D, Butelase 1 and Trypsiligase.

Accordingly, in some embodiments of any one of the aspects described herein, the linker comprises an amino acid sequence recognized by a sortase (e.g., Sortase A, Sortase B, Sortase C or Sortase D). Sortase A-D are peptide ligases that are responsible from the post-translational tethering of surface proteins to the cell wall of Gram-positive bacteria. The most commonly used enzyme is Sortase A from *Staphylococcus aureus*. Sortase A recognizes a C-terminal LPXTG (SEQ ID NO: 47) motif within its substrate and then cleaves the bond between the Thr-Gly (TG) residues. The acylenzyme intermediate can react with a variety of N-terminal poly-G payloads to couple two proteins or peptides of interest. Accordingly, in some embodiments of any one of the aspects described herein, the linker comprises the amino acid sequence LPXTG (SEQ ID NO: 47), where X is any amino acid. For example, the linker comprises the amino acid sequence LPETG (SEQ ID NO: 48). In some embodiments of any one of the aspects described herein, the linker comprises the amino acid sequence LPXTGGGGG (SEQ ID NO: 49), where X is any amino acid. For example, the linker comprises the amino acid sequence LPETGGGGG (SEQ ID NO: 50)

In some embodiments of any one of the aspects described herein, the linker comprises an amino acid sequence recognized by Butelase 1. Butelase 1 is a peptide ligase that is a naturally occurring cyclase involved in the biosynthesis of cyclotides. Butelase-1 recognizes a C-terminal tripeptide sequence D/N-HV tripeptide. It cleaves the bond between D/N and HV followed by forming a bond between the C-terminus of D/N and N-terminal residue. Accordingly, in some embodiments of any one of the aspects described herein, the linker comprises the amino acid sequence D/N-X, where X is any amino acid residue. For example, the linker comprises the amino acid sequence D/N-GI.

In some embodiment of any one of the aspects described herein, the linker comprises an amino acid sequence recognized by Trypsiligase. Trypsiligase is a mutant of trypsin and has been used for the selective modification of N- and C-terminal residues of several proteins with different reagents. It recognizes a tripeptide motif of Y-RH. Accordingly, in some embodiments of any one of the aspects described herein, the linker comprises the amino acid sequence Y-RH.

In some embodiments of the various aspects described herein, the linker can be a chemical linker. By a chemical linker is meant a linker that does not comprise an amino acid residue in the backbone. Chemical linkers are also referred to as non-peptide linkers herein. Chemical linkers can comprise an atom such as oxygen or sulfur, a unit such as NH, C(O), C(O)NH, SO, $SO_2$, $SO_2NH$, or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, or C(O). In some embodiments of any one of the aspects described herein, the chemical linker can be ethylene glycol or polyethylene glycol, e.g., diethyleneglycol (PEG-2), triethylene glycol (PEG-3), tetraethylene glycol (PEG-4), pentaethylene glycol (PEG-5), hexaethylene glycol (PEG-6), heptaethylene glycole (PEG-7), octaethylene glycol (PEG-8), nonaethylene glycol (PEG-9) or decaethylene glycol (PEG-10).

A linker can be a flexible linker or a rigid linker. As used herein, a "flexible linker" is a linker which does not have a fixed structure (secondary or tertiary structure) in solution and is therefore free to adopt a variety of conformations. Generally, a flexible linker has a plurality of freely rotating bonds along its backbone. In contrast, a rigid linker is a linker which adopts a relatively well-defined conformation when in solution. Rigid linkers are therefore those which have a particular secondary and/or tertiary structure in solution.

A linker can be a cleavable linker. Cleavable linkers are those that rely on processes inside a target cell to liberate the two parts the linker is holding together, as reduction in the cytoplasm, exposure to acidic conditions in a lysosome or endosome, or cleavage by specific enzymes (e.g. proteases or nucleases) within the cell. As such, cleavable linkers allow the two parts to be released in their original form after internalization and processing inside a target cell. Cleavable linkers include, but are not limited to, those whose bonds can be cleaved by enzymes (e.g., peptide linkers); reducing conditions (e.g., disulfide linkers); or acidic conditions (e.g., hydrazones and carbonates).

Generally, the cleavable linker comprises at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

One class of cleavable linking groups is redox cleavable linking groups, which can be used according to the present invention that are cleaved upon reduction or oxidation. An example of reductively cleavable linking group is a disulfide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-based cleavable linking groups, which can be used according to the present invention, are cleaved by agents that degrade or hydrolyze the phosphate group. An example of an agent that cleaves phosphate groups in cells are enzymes such as phosphatases in cells.

Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—, wherein Rk at each occurrence can be, independently, hydrogen, C1-C20 alkyl, C1-C20 haloalkyl, C6-C10 aryl, C7-C12 aralkyl. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid cleavable linking groups, which can be used according to the present invention, are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-based cleavable linking groups, which can be used according to the present invention, are cleaved by enzymes such as esterases and amidases in cells. Examples of ester-based cleavable linking groups include but are not limited to esters of alkylene, alkenylene and alkynylene groups. Ester cleavable linking groups comprise the group —C(O)O—, or —OC(O)—.

Peptide-based cleavable linking groups, which can be used according to the present invention, are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids.

In some embodiments of any one of the aspects described herein, the cleavable linker comprises a peptide-based cleavable linking group. For example, the cleavable linker comprises a peptide comprising the amino acid sequence valine-citrulline (VC). It is noted that the valine-citrulline dipeptide can be cleaved by cathepsin B. In the case of a cathepsin B cleavable linker the dipeptide can also be replaced with a tripeptide, glutamic acid-valine-citrulline, to enable stability in murine studies. See for example, Anami et al in 2018. Accordingly, in some embodiments of any one of the aspects described herein, the cleavable linker comprises a peptide comprising the amino acid sequence glutamic acid-valine-citrulline (EVC).

In some embodiments of any one of the aspects described herein, the cleavable linker comprises a linking group, e.g., a peptide-based cleavable linking group that is cleaved a metalloproteinase, e.g., a matrix metalloproteinase.

In some embodiments of any one of the aspects described herein, the linker comprises a self-immoliative linking group. As used herein, a "self-immoliative" linking group is a bifunctional chemical moiety which is capable of covalently linking together two chemical moieties into a normally stable molecule, releasing one of said chemical moieties from the stable molecule by means of cleavage of a cleavable linking group in the linker, and following said cleavage, spontaneously cleaving from the remainder of the molecule to release the other of said chemical moieties. Exemplary self-immoliative linking groups include, but are not limited to, p-aminebenzyloxycarbonyl, disulfide, heteroaminebifunctional disulfides, thiol-based pirydazinediones, Gly-Pro dipeptide, L-Phe-Sar dipeptide, trans-cyclooctene tetrazines, ortho hydroxy-protected aryl phosphoramidates, hydroxybenzyl, trimethyl carbamate, and quinone methides.

In some embodiments of any one of the aspects described herein, the linker comprises a cleavable linking group linked to a self-immoliative linking group. For example, the linker comprises a peptide-based cleavable linking group linked directly, e.g., by a bond to a self-immoliative linking group.

In some embodiments of any one of the aspects described herein, a cleavable linker comprises peptide comprising the amino acid sequence glutamic acid-valine-citrulline linked directly to a self-immoliative linking group. For example, the cleavable linker comprises valine-citrulline-p-aminobenzylcarbamate (VC-PBAC). In some embodiments of any one of the aspects described herein, the cleavable linker comprises glutamic acid-valine-citrulline-p-aminobenzylcarbamate (EVC-PBAC).

Some exemplary linkers include, but are not limited to, LPXTG, X is any amino acid (SEQ ID NO: 47), LPTEG (SEQ ID NO: 48), LPTXGGGGG (SEQ ID NO: 49), LPTEGGGGG (SEQ ID NO: 50), triethyleneglycol-valine-citrulline-p-aminobenzylcarbamate (PEG$_3$-VC-PBAC), triethyleneglycol-valine-citrulline-p-aminobenzylcarbamate (PEG$_3$-VC-PBAC), PEG-2, PEG-3, PEG-4, PEG-5, PEG-6, PEG-7, PEG-8, PEG-9, PEG-10, or any combination thereof.

Payload Molecule (Ligand)

Embodiments of the various aspects described herein include a payload molecule, e.g., a ligand. As used herein, a payload molecule, e.g. a ligand can be selected from small organic and inorganic molecules, amino acids, peptides, polypeptides, peptidomimetics, glycoproteins, lectins, nucleosides, nucleotides, monosaccharides, disaccharides, trisaccharides, oligosaccharides, polysaccharides, lipopolysaccharides, vitamins, steroids, hormones, and cofactors.

It is noted the payload molecule, e.g., the ligand can have some desirable properties or characteristics. For example, the payload molecule, e.g., the ligand can be a therapeutic agent, diagnostic agent, imaging agent or a detectable label.

In some embodiments of any one of the aspects described herein, the ligand is a nucleic acid. For example, the ligand is an siRNA, shRNA, antisense oligonucleotide, aptamer, ribozyme, miRNA, antigomir, triplex forming oligonucleotide, activating RNA, guide-RNA, cr-RNA, or mRNA.

Therapeutic Agents

Accordingly, in some embodiments of any one of the aspects described herein, the ligand is a therapeutic agent. The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

In some embodiments of any one of the aspects described herein, the therapeutic agent is an anti-cancer agent. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; gemicitabine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof.

In some embodiments, the anti-cancer agent is selected from the group consisting of gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Angew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin; lapatinib (Tykerb®); inhibitors of PKC-alpha, Raf, H-Ras, EGFR (e.g., erlotinib (Tarceva®)) and VEGF-A.

In some embodiments of any one of the aspects described herein, the anti-cancer agent is selected from the group consisting of doxorubicin, daunorubicin, actinomycin, camptothecins (e.g., such as irinotecan and topotecan), epipodophyllotoxins (such as etoposide and teniposide), taxane (e.g., such as paclitaxel and docetaxel), tyrosine kinase inhibitors (e.g., such as, rucaparib, olaparib, imatinib, masitinib, nilotinib and toceranib), and vinca alkaloids (e.g., such as vinblastine, vincristine, and vinorelbine).

In some embodiments of any one of the aspects described herein, the anti-cancer agent is Monomethyl auristatin E (MMAE). Monomethyl auristatin E (MMAE) is a synthetic antineoplastic agent. It is an antimitotic agent which inhibits cell division by blocking the polymerization of tubulin.

Detectable Label

In some embodiments, the ligand comprises a detectable label. As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

In some embodiments, the detectable label can be an imaging agent or contrast agent. As used herein, the term "imaging agent" refers to an element or functional group in a molecule that allows for the detection, imaging, and/or monitoring of the presence and/or progression of a condition(s), pathological disorder(s), and/or disease(s). The imaging agent can be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like. In some embodiments, the detectable labels also encompass any imaging agent (e.g., but not limited to, a bubble, a liposome, a sphere, a contrast agent, or any detectable label described herein) that can facilitate imaging or visualization of a tissue or an organ in a subject, e.g., for diagnosis of an infection.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound.

Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.18; Cy3.5™; Cy3™; Cy5.18; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DUPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydrohodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene);

NBD; NBD Amine; Nile Red; Nitrobenzoxadidole; Noradrenaline; Nuclear Fast Red; Nuclear Yellow; Nylosan Brilliant Iavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; Tru-Red; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include luminescent and bioluminescent markers (e.g., biotin, luciferase (e.g., bacterial, firefly, click beetle and the like), luciferin, and aequorin), radiolabels (e.g., 3H, 125I, 35S, 14C, or 32P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane. Suitable non-metallic isotopes include, but are not limited to, 11C, 14C, 13N, 18F, 123I, 124I, and 125I. Suitable radioisotopes include, but are not limited to, 99mTc, 95Tc, 111In, 62Cu, 64Cu, Ga, 68Ga, and 153Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir. In some embodiments, the radionuclide is bound to a chelating agent or chelating agent-linker attached to the antibody conjugate molecule. Suitable radionuclides for direct conjugation include, without limitation, 18F, 124I, 125I, 131I, and mixtures thereof. Suitable radionuclides for use with a chelating agent include, without limitation, 47Sc, 64Cu, 67Cu, 89Sr, 86Y, 87Y, 90Y, 105Rh, 111Ag, 111In, 117mSn, 149Pm, 153Sm, 166Ho, 177Lu, 186Re, 188Re, 211At, 212Bi, and mixtures thereof. Suitable chelating agents include, but are not limited to, DOTA, BAD, TETA, DTPA, EDTA, NTA, HDTA, their phosphonate analogs, and mixtures thereof. One of skill in the art will be familiar with methods for attaching radionuclides, chelating agents, and chelating agent-linkers to molecules such as the antibody conjugate molecules and carrier scaffolds disclosed herein.

In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the microbes isolated from or remained bound on the antibody conjugate substrate can be stained with at least one stain, e.g., at least one fluorescent staining reagent comprising a microbe-binding molecule, wherein the microbe-binding molecule comprises a fluorophore or a quantum dot. Examples of fluorescent stains include, but are not limited to, any antibody conjugate element (e.g., microbe-specific antibodies or any microbe-binding proteins or peptides or oligonucleotides) typically conjugated with a fluorophore or quantum dot, and any fluorescent stains used for detection as described herein. In some embodiments, the detectable label is a gold particle.

In some embodiments, the detectable label can be configured to include a "smart label", which is undetectable when conjugated to the microbe-binding molecules, but produces a color change when released from the engineered molecules in the presence of a microbe enzyme. Thus, when a microbe binds to the engineered microbe-binding molecules, the microbe releases enzymes that release the detectable label from the engineered molecules. An observation of a color change indicates presence of the microbe in the sample.

Methods of Preparing

In another aspect, provided herein is a method for preparing a polypeptide linked on its C-terminus to a coiled-coil peptide. The method comprises contacting a polypeptide comprising on its C-terminus a recognition amino acid sequence for a peptide ligase with a coiled-coil peptide in the presence of a peptide ligase under conditions under conditions wherein the peptide ligase catalyzes the formation of a peptide bond between N-terminus of the coiled-coil peptide and C-terminus of an amino acid in the recognition amino acid sequence.

In some embodiments of any one of the aspects described herein, the recognition amino acid sequence is linked at its C-terminus to an affinity tag. The affinity tags enable purification of the polypeptide via the use of affinity resins and/or column chromatography. Generally, the affinity tag is cleaved prior to ligation with the coiled-coil peptide. Thus, the affinity tag can be used to separate or purify the polypeptide ligated with the coiled-coil peptide from the unreacted polypeptide.

A number of epitope or affinity tags are known in the art. These are usually divided into 3 classes according to their size: small tags have a maximum of 12 amino acids, medium-sized ones have a maximum of 60 and large ones have more than 60. The small tags include the Arg-tag, the His-tag, streptactin binding domain, the avidin biotin, or streptavidin (Strep)-tag, the Flag-tag, the T7-tag, the V5-peptide-tag and the c-Myc-tag, the medium-sized ones include the S-tag, the HAT-tag, the calmodulin-binding peptide, the chitin-binding domain (CBD) and some cellulose-binding domains. The latter can contain up to 189 amino acids and are then regarded, like the glutathione-S-transferase (GST)- and maltose binding protein (MBP)-tag, as large affinity tags.

Some exemplary affinity tag sequences include, but are not limited to, GWSHPQFEK (SEQ ID NO: 61), 6-HIS tag (HHHHHH (SEQ ID NO: 62), HA tag (YPYDVPDYA, SEQ ID NO: 63), ac-Myc epitope (EQKLISEEDL, SEQ ID NO: 64), AU1 tag (DTYRYI, SEQ ID NO: 65), Flag-tag (DYKDDDDK, SEQ ID NO: 66). In some preferred embodiments, the affinity tag comprises a streptactin binding domain comprising the amino acid sequence of GWSHPQFEK (SEQ ID NO: 61).

In some embodiments of any one of the aspects described herein, the peptide ligase comprises peptidase activity. A peptide ligase having peptidase activity can be used to cleave a peptide bond between the recognition amino acid sequence and the affinity tag prior to ligation.

In some embodiments of any one of the aspects described herein, the coiled-coil peptide for ligation comprises the amino acid sequence GGGGG (SEQ ID NO: 55) at its N-terminus.

In some embodiments of any one of the aspects described herein, the polypeptide comprises the amino acid sequence LPETG-$X^T$ (SEQ ID NO: 54), where $X^T$ is an affinity tag, at its C-terminus.

After ligation, the polypeptide can be purified Exemplary purification methods include, but are not limited to affinity chromatography, anion exchange chromatography, cation exchange chromatography, boronate affinity chromatography, lectin affinity chromatography, immunoaffinity chromatography, immobilized metal affinity chromatography, protein affinity chromatography, and size exclusion chromatography.

In some embodiments, the method comprises preparing the polypeptide and/or coiled-coil peptide prior to ligation. Methods for preparing polypeptides and coiled-coil peptides are well known in the art and available to the practitioner. Such methods include, recombinantly expressing the polypeptides and peptides.

Uses

The conjugates, e.g. antibody conjugates described herein can be used for delivering an agent, e.g., a ligand to a cell. Generally, the method comprises providing to the cell a conjugate, e.g., an antibody conjugate described herein. Methods for providing a compound to a cell are well known and available to one of skill in the art. As used herein, providing the conjugate to the cell means contacting the cell with the conjugate so that the conjugate, e.g., antibody conjugate is taken up by the cell. Generally, the cell can be contacted with the conjugate in a cell culture e.g., in vitro or ex vivo, or the conjugate can be administrated to a subject, e.g., in vivo. The term "contacting" or "contact" as used herein in connection with contacting a cell includes subjecting the cells to an appropriate culture media, which comprises a conjugate, e.g., an antibody conjugate described herein. Where the cell is in in vivo, "contacting" or "contact" includes administering the conjugate, e.g., in a pharmaceutical composition to a subject via an appropriate administration route such that the conjugate contacts the cell in vivo. When the cell in in vivo, the subject can be a mammal. For example, the subject can be a human.

In some embodiments, the cell is in vivo in a subject, where the subject is in need of treatment for a disease or disorder, and wherein the conjugate comprises a ligand that is a therapeutic agent useful for treating the disease or disorder.

In some embodiments, the cell is a cancer cell and the conjugate comprises a ligand that is an anti-cancer agent. For example, the cancer cell is in vivo in a subject, where the subject is in need of treatment for cancer, and wherein the conjugate comprises a ligand that an anti-cancer agent.

As described herein, conjugates where the ligand is a therapeutic agent or a diagnostic agent can be used for treating or diagnosing a disease or disorder. Accordingly, in another aspect provided herein is a method for treating a disease or disorder in a subject. Generally, the method comprises administering a conjugate, e.g., an antibody conjugate described herein, where the ligand in the conjugate is a therapeutic agent is use for treating said disease or disorder. It is noted that the subject can be currently undergoing treatment or already has undergone treatment for the disease or disorder.

In some embodiments of the method for treating a disease or disorder, the method further comprises co-administering a second therapy to the subject, wherein the second therapy is useful for treating said disease or disorder. In some embodiments, the method for treating a disease or disorder further comprises co-administering a second conjugate, e.g. a second antibody conjugate, where the second conjugate comprises a ligand, i.e., a therapeutic that is different from the ligand (therapeutic agent) of the first conjugate and where the ligand, i.e., the therapeutic agent of the second conjugate is useful treating the disease or disorder.

In some embodiments of any one of the aspects described herein, the subject is in need for treatment for cancer. Accordingly, in another aspect, provided herein is a method for treating cancer. The method comprises administering a conjugate, e.g., an antibody conjugate described herein to a subject in need of treatment for cancer, and where the ligand in the conjugate, e.g., the antibody conjugate is an anti-cancer agent.

As used herein, the term "cancer" refers to a class of diseases or conditions that are characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

Examples of cancer that can be treated with the conjugates described herein include, but are not limited to, neuroma, acute lymphoblastic leukemia (ALL), adenocarcinoma, angiosarcoma, astrocytoma, basal cell carcinoma, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia), bile duct carcinoma, bladder cancer, bone cancer, brain tumor, breast cancer, bronchogenic carcinoma, cancer of the peritoneum, cervical cancer, chondrosarcoma, chordoma, choriocarcinoma, chronic lymphocytic leukemia (CLL), colon carcinoma, colorectal cancer, craniopharyngioma, cystadenocarcinoma, embryonal carcinoma, endometrial or uterine carcinoma, endotheliosarcoma, ependymoma, epithelial carcinoma, Ewing's tumor, fibrosarcoma, gastric cancer, glioblastoma, Hairy cell leukemia, head and neck cancer, heavy chain disease, hemangioblastoma, hepatocellular cancer, kidney or renal cancer, leiomyosarcoma, liposarcoma, liver cancer, lung carcinoma, lymphangioendothelial sarcoma, lymphangiosarcoma, lymphoma (Hodgkin's disease and non-Hodgkin's disease), medullary carcinoma, medulloblastoma, melanoma, meningioma, mesothelioma, multiple myeloma, myeloblastic leukemia, myxosarcoma, neuroblastoma, oligodendroglioma, osteogenic sarcoma, ovarian cancer, pancreatic cancer, papillary adenocarcinomas, papillary carcinoma, pinealoma, polycythemia vera, prostate cancer, renal cell carcinoma, retinoblastoma; leukemia (e.g. acute lymphocytic leukemia, chronic lymphocytic leukemia (CLL) and acute myeloid leukemia (myeloblastic; promyelocytic, myelomonocytic, monocytic and erythroleukemia), chronic leukemia (chronic myelocytic (granulocytic) leukemia and chronic lymphocytic leukemia)), rhabdomyosarcoma, salivary gland carcinoma, sebaceous gland carcinoma, seminoma, small cell lung carcinoma, squamous cell carcinoma, sweat gland carcinoma, synovial sarcoma, synovioma testicular cancer, thyroid cancer, vulvar cancer, Waldenstrom macroglobulinemia, Wilms' tumor, and post-transplant lymphoproliferative disorder (PTLD), as well as abnormal vascular proliferation associated with phakomatoses, edema (such as that associated with brain tumors), and Meigs' syndrome.

In some embodiments of the method for treating cancer, the method can further comprise co-administering an additional anti-cancer therapy to the subject. For example, administering a standard of care chemotherapeutic to the subject. Non-limiting examples of a standard of care chemotherapeutics or other anti-cancer therapy can include radiation therapy, surgery, Additional anti-cancer treatment can further include the use of radiation or radiation therapy. Further, the additional anti-cancer treatment can also include the use of surgical treatments.

Combination Therapy

The methods for treatment described herein can further comprise administering a second agent and/or treatment to the subject, e.g. as part of a combinatorial therapy. The additional therapy can be administered prior to, simultaneously with, or after administering the conjugate, e.g., antibody conjugate described herein.

The phrase "combination therapy" as used herein means administration a conjugate, e.g., an antibody conjugate and one or more additional therapies as part of a specific treatment regimen intended to provide a beneficial effect from the co-action of these. The beneficial effect of the combination includes, but is not limited to, pharmacokinetic or pharmacodynamic co-action resulting from the combination of therapeutic agents. Administration of these therapeutic agents in combination typically is carried out over a defined time period. The time period may be in minutes, hours, days or weeks depending upon the combination selected.

Combination therapy includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be done, for example, by administering to the subject a single pill having a fixed ratio of each therapeutic agent or in multiple, single pills for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered may or may not be important.

Combination therapy also can mean the administration of one or more ADCs in further combination with other compounds and non-drug therapies, such as, but not limited to, surgery or radiation treatment. Where the combination therapy further comprises radiation treatment, the radiation treatment may be conducted at any suitable time so long as a beneficial effect from the co-action of the combination of the therapeutic agents and radiation treatment is achieved.

Pharmaceutical Compositions

For administration to a subject, the conjugates described herein can be provided in pharmaceutically acceptable compositions. These pharmaceutically acceptable compositions comprise a conjugate, e.g., an antibody conjugate described herein formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, conjugates can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and 35 U.S. Pat. No. 3,270,960, content of all of which is herein incorporated by reference.

As used here, the term "pharmaceutically acceptable" refers to those conjugates, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject conjugate from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Examples of solid carriers include starch, sugar, bentonite, silica, and other commonly used carriers. Further non-limiting examples of carriers and diluents which can be used in the formulations comprising a conjugate of Formula (I) as disclosed herein of the present invention include saline, syrup, dextrose, and water.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The phrase "therapeutically-effective amount" as used herein means that amount of a conjugate, material, or composition which is effective for producing some desired therapeutic effect in at least a sub-population of cells in an animal at a reasonable benefit/risk ratio applicable to any medical treatment. According, a "therapeutically effective amount" refers to an amount effective, at dosage and periods of time necessary, to achieve a desired therapeutic result. A therapeutic result can be, e.g., lessening of symptoms, prolonged survival, improved mobility, and the like. A therapeutic result need not be a "cure."

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The conjugates can be formulated in a gelatin capsule, in tablet form, dragee, syrup, suspension, topical cream, suppository, injectable solution, or kits for the preparation of syrups, suspension, topical cream, suppository or injectable solution just prior to use. Also, conjugates can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., Remington's Pharmaceutical Sciences, Mack Publishing Co., Easton, Pa. 1985, 17th edition, Nema et al., PDA J. Pharm. Sci. Tech. 1997 51:166-171. Methods to make invention formulations include the step of bringing into association or contacting an ActRIIB conjugate with one or more excipients or carriers. In general, the formulations are prepared by uniformly and intimately bringing into association one or more conjugates with liquid excipients or finely divided solid excipients or both, and then, if appropriate, shaping the product.

The preparative procedure may include the sterilization of the pharmaceutical preparations. The conjugates may be mixed with auxiliary agents such as lubricants, preservatives, stabilizers, salts for influencing osmotic pressure, etc., which do not react deleteriously with the conjugates.

Examples of injectable form include solutions, suspensions and emulsions. Injectable forms also include sterile powders for extemporaneous preparation of injectable solutions, suspensions or emulsions. The conjugates of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin. A suitable carrier is 5% dextrose in saline. Frequently, it is desirable to include additives in the carrier such as buffers and preservatives or other substances to enhance isotonicity and chemical stability.

In some embodiments, conjugates can be administrated encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a pituitary cell) can also be used as pharmaceutically acceptable carriers.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or conjugates.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185; content of each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the conjugates are prepared with carriers that will protect the conjugate against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and Primogel™, and the like. The conjugates can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these conjugates may be incorporated with excipients and used in the form of tablets, capsules, elixirs, suspensions, syrups, and the like. Such compositions and preparations should contain at least 0.1% of conjugate. The percentage of the agent in these compositions may, of course, be varied and may conveniently be between about 2% to about 60% of the weight of the unit. The amount of conjugate in such therapeutically useful compositions is such that a suitable dosage will be obtained. Preferred compositions according to the present invention are prepared so that an oral dosage unit contains between about 100 and 2000 mg of conjugate. Examples of bases useful for formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives. The compositions can be given as a bolus dose, to maximize the circulating levels for the greatest length of time after the dose. Continuous infusion may also be used after the bolus dose.

The conjugates can also be administrated directly to the airways in the form of an aerosol. For administration by inhalation, the conjugates in solution or suspension can be delivered in the form of an aerosol spray from pressured container or dispenser which contains a suitable propellant, e.g., a gas such as carbon dioxide, or hydrocarbon propellant like propane, butane or isobutene. The conjugates can also be administrated in a no-pressurized form such as in an atomizer or nebulizer.

In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the conjugate described herein and a suitable powder base such as lactose or starch.

Representative intranasal formulations are described in, for example, U.S. Pat. Nos. 4,476,116, 5,116,817 and 6,391,452. Formulations that include a conjugate of Formula (I) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions The conjugates can also be administered parenterally. Solutions or suspensions of these conjugates can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of conjugate calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the conjugates are formulated into ointments, salves, gels, or creams as generally known in the art.

For oral or enteral formulations as disclosed herein for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982. As regards formulations for administering a conjugate of Formula I as disclosed herein, one particularly useful embodiment Also provided herein is a tablet formulation comprising a conjugate of Formula I with an enteric polymer casing. An example of such a preparation can be found in WO2005/021002. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof, binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient, e.g., conjugate of Formula I preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg of the active ingredient. Particularly preferably, the core contains 20, 30, 40, 50, 60, 80 or 100 mg of the active ingredient. The active ingredient can be present as is or as any pharmaceutically acceptable salt. If the active ingredient is present as a salt, the weight is adjusted such that the tablet contains the desired amount of active ingredient, calculated as free base or free acid of the salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

In some embodiments, an entericcoating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticizers and up to around 50 wt % of anti-tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%.

A seal coat can also be included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876. Other enteric-coated preparations of this sort can be prepared by one skilled in the art, using these materials or their equivalents.

For intravenous injections or drips or infusions, conjugates described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspension, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

Routes of Administration

It is noted that the terms "administered" and "subjected" are used interchangeably in the context of treatment of a disease or disorder. In jurisdictions that forbid the patenting of methods that are practiced on the human body, the meaning of "administering" of a composition to a human subject shall be restricted to prescribing a controlled substance that a human subject will be administer to the subject by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A conjugate, e.g., antibody conjugate or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, administration will generally be local rather than systemic.

The phrase "therapeutically-effective amount" as used herein means that amount of a conjugate, material, or composition comprising a conjugate described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to affect such treatment for the disease.

Depending on the route of administration, effective doses can be calculated according to the body weight, body surface area, or organ size of the subject to be treated. Optimization of the appropriate dosages can readily be made by one skilled in the art in light of pharmacokinetic data observed in human clinical trials. Alternatively, or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

Determination of an effective amount is well within the capability of those skilled in the art. Generally, the actual effective amount can vary with the specific conjugate, the use or application technique, the desired effect, the duration of the effect and side effects, the subject's history, age, condition, sex, as well as the severity and type of the medical condition in the subject, and administration of other pharmaceutically active agents. Accordingly, an effective dose of conjugate described herein is an amount sufficient to produce at least some desired therapeutic effect in a subject.

The data obtained from the cell culture assays and animal studies can be used in formulating a range of dosage for use in humans. The dosage of such conjugates lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a conjugate as disclosed herein can be about 0.01 µM to about 10 µM, about 0.2 µM to about 5 µM, or about 0.8 to about 3 µM in a subject, such as a rat, dog, or human.

Generally, the compositions are administered so that a conjugate of the disclosure herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The conjugates described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The conjugates can be administered as a single bolus or multiple boluses, as a continuous infusion, or a combination thereof. For example, the conjugate can be administered as a single bolus initially, and then administered as a continuous infusion following the bolus. The rate of the infusion can be any rate sufficient to maintain effective concentration, for example, to maintain effective plasma concentration. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the conjugate, such that the conjugate is administered via infusion at a rate sufficient to safely maintain a sufficient effective plasma concentration of conjugate in the bloodstream.

For in vivo administration, the compositions or preparations described herein can be administered with a delivery device, e.g., a syringe. Accordingly, an additional aspect described herein provides for delivery devices comprising at least one chamber with an outlet, wherein the at least one chamber comprises a pre-determined amount of any composition described herein and the outlet provides an exit for the composition enclosed inside the chamber. In some embodiments, a delivery device described herein can further comprise an actuator to control release of the composition through the outlet. Such delivery device can be any device to facilitate the administration of any composition described herein to a subject, e.g., a syringe, a dry powder injector, a nasal spray, a nebulizer, or an implant such as a microchip, e.g., for sustained-release or controlled release of any composition described herein.

Some exemplary embodiments of the various aspects described herein can be described as the following numbered embodiments:

Embodiment 1: An antibody, wherein a polypeptide chain of the antibody is linked on its C-terminus to a coiled-coil peptide, wherein the coiled-coil peptide is capable of forming a heterodimer with another coiled-coil peptide.

Embodiment 2: The antibody of Embodiment 1, wherein said polypeptide chain is a heavy chain of the antibody.

Embodiment 3: The antibody of Embodiment 1 or 2, wherein the coiled-coil peptide comprises an amino acid sequence selected from the group consisting of SEQ ID NOs: 1-46.

Embodiment 4: The antibody of any one of Embodiments 1-3, wherein the coiled-coil peptide comprises the amino acid sequence of SEQ ID NO: 1.

Embodiment 5: The antibody of any one of Embodiments 1-4, wherein the coiled-coil peptide is linked to the C-terminus of the heavy chain via a peptide linker.

Embodiment 6: The antibody of Embodiment 5, wherein the linker comprises a recognition amino acid sequence for a peptide ligase.

Embodiment 7: The antibody of Embodiment 6, wherein the linker comprises a Sortase A recognition sequence.

Embodiment 8: antibody of any one of Embodiments 5-7-, wherein the linker comprises the amino acid sequence LPETG (SEQ ID NO: 48) or LPETGGGGG (SEQ ID NO: 50).

Embodiment 9: antibody of any one of Embodiments 1-8, wherein the antibody is an anti-GPR87 antibody (331CL) or anti-DEspR antibody (7c5).

Embodiment 10: antibody of any one of Embodiments 1-9, wherein the antibody is a monoclonal antibody.

Embodiment 11: antibody of any one of Embodiments 1-11, wherein the antibody is a humanized antibody.

Embodiment 12: An antibody conjugate comprising an antibody of any one of Embodiments 1-11 and a ligand conjugated with a coiled-coil peptide, wherein the coiled-coil peptide forms a heterodimer with the coiled-coil peptide linked to the heavy chain of the heavy chain.

Embodiment 13: The antibody conjugate of Embodiment 12, wherein the coiled-coil peptide conjugated with the ligand comprises an amino acid sequence selected from the group consisting of SEQ ID NOs: 1-46.

Embodiment 14: The antibody conjugate of Embodiment 12 or 13, wherein the coiled-coil peptide conjugated with the ligand comprises the amino acid sequence MK(LEEIVXE)$_4$VGER where each X is independently serine, tyrosine, or a N-ε-azido lysine (SEQ ID NO: 2), MK(LEEIVSE)$_2$LEEIV(K-azido)ELEEIVYEVGER, where K-azido is N-ε-azido lysine (SEQ ID NO: 3), or SPEDEIQALEEENAQLEQE-NAALEEE LAQLEYGK-azidoG (SEQ ID NO: 4).

Embodiment 15: The antibody of conjugate of any one of Embodiments 12-14, wherein the coiled-coil peptide conjugated with the ligand comprises the amino acid sequence MK-LEEIVSE-LEEIVSE-LEEIV(X$^1$)E-LEEIVYE-VGER (SEQ ID NO: 51) or SPEDEIQALEEENAQLEQENAA-LEEE LAQLEYGX$^1$KG (SEQ ID NO: 52), where X$^1$ is lysine linked at N-ε position with —X$^2$-L, where X$^2$ is a linker and L is a ligand.

Embodiment 16: The antibody of conjugate of any one of Embodiments 12-15, wherein the ligand is selected from the group consisting of small organic and inorganic molecules, amino acids, peptides, polypeptides, peptidomimetics, glycoproteins, lectins, nucleosides, nucleotides, monosaccharides, disaccharides, trisaccharides, oligosaccharides, polysaccharides, lipopolysaccharides, vitamins, steroids, hormones, and cofactors.

Embodiment 17: The antibody of conjugate of any one of Embodiments 12-16, wherein the ligand is a therapeutic agent, an imaging agent or a detectable label.

Embodiment 18: The antibody of conjugate of any one of Embodiments 12-17, wherein ligand is a therapeutic agent (e.g., anti-cancer agent).

Embodiment 19: The antibody of conjugate of any one of Embodiments 12-18, wherein the ligand is linked to the peptide via a linker comprising a cleavable linking group.

Embodiment 20: The antibody of conjugate of any one of Embodiments 12-19, wherein the linker linking the ligand to the peptide comprises the tripeptide glutamic acid-valine-citrulline (EVC).

Embodiment 21: The antibody of conjugate of any one of Embodiments 12-20, wherein the linker comprises triethyleneglycol-glutamic acid-valine-citrulline-p-aminobenzylcarbamate (PEG3-EVC-PABC).

Embodiment 22: The antibody of conjugate of any one of Embodiments 12-21, wherein the ligand is linked to an internal amino acid of the peptide.

Embodiment 23: A pharmaceutical composition comprising an antibody conjugate of any one Embodiments 12-22 and a pharmaceutically acceptable carrier.

Embodiment 24: A method for preparing a polypeptide linked on its C-terminus to a coiled-coil peptide, the method comprising: contacting a polypeptide comprising on its C-terminus a recognition amino acid sequence for a peptide ligase with a coiled-coil peptide in the presence of a peptide ligase under conditions under conditions wherein the peptide ligase catalyzes the formation of a peptide bond between N-terminus of the coiled-coil peptide and C-terminus of an amino acid in the recognition amino acid sequence.

Embodiment 25: The method of Embodiment 24, wherein the recognition amino acid sequence is linked at its C-terminus to an affinity tag.

Embodiment 26: The method of Embodiment 24 or 25, wherein the peptide ligase comprises peptidase activity.

Embodiment 27: The method of any one of Embodiments 24-26, wherein the ligase cleaves a peptide bond between the recognition amino acid sequence and the affinity tag prior to ligation.

Embodiment 28: The method of any one of Embodiments 24-27, wherein the coiled-coil peptide comprises the amino acid sequence GGGGG (SEQ ID NO: 55) at its N-terminus.

Embodiment 29: The method of any one of Embodiments 24-28, wherein the polypeptide comprises the amino acid sequence LPXTG-X$^T$ (SEQ ID NO: 53) or LPETG-X$^T$ (SEQ ID NO: 54), where X is any amino acid and X$^T$ is an affinity tag.

Embodiment 30: A method of delivering at least one ligand to a cell, the method comprising providing to the cell an antibody conjugate of any one of Embodiments 24-29

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other than in the operating examples, or where otherwise indicated, all numbers expressing quantities of ingredients or reaction conditions used herein should be understood as modified in all instances by the term "about." The term "about" when used to described the present invention, in connection with percentages means±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

The term "statistically significant" or "significantly" refers to statistical significance and generally means a two standard deviation (2SD) or greater difference.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; (3) bringing about ameliorations of the symptoms of the disease or condition; or (4) curing the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively, or additionally, the treatment can be administered after initiation of the disease or condition, for a therapeutic action.

In some embodiments, treatment is therapeutic and does not include prophylactic treatment.

The terms "co-administration" or the like, as used herein, are meant to encompass administration of the selected therapeutic agents to a single patient and are intended to include treatment regimens in which the agents are administered by the same or different route of administration or at the same or different time. The particular combination of therapies (therapeutics or procedures) to employ in such a combination regimen will take into account compatibility of the desired therapeutics and/or procedures and the desired therapeutic effect to be achieved.

As used herein, the term "subject" refers to any living organism which can be administered conjugate and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult, child and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the conjugates and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc.

In some embodiments, the subject is a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of viral-infections.

It is noted that a human subject can be of any age, gender, race or ethnic group, e.g., Caucasian (white), Asian, African, black, African American, African European, Hispanic, Middle eastern, etc.

In addition, the methods described herein can be used to treat domesticated animals and/or pets. A subject can be male or female. A subject can be one who has been previously diagnosed with or identified as suffering from or having a viral infection, but need not have already undergone treatment.

In some embodiments of any one of the aspects, the subject is human.

Other terms are defined herein within the description of the various aspects of the invention.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims.

EXAMPLES

The technology described herein is further illustrated by the following examples which in no way should be construed as being further limiting.

Example 1: Synthesis and Characterization of Coiled-Coil Mediated Antibody Fluorophore and Drug Conjugates Production of the CCK Labeled αGPR87 Antibody A step in actualizing the concept of antibody conjugates via coiled-coil assembly is producing and purifying an antibody expressing the CCK peptide on the C termini (Ab-CCK). Two different methods were employed to achieve this goal.

The first method is to append the CCK peptide sequence onto the C terminus of the heavy chain of an antibody via a pentaglycine linker with recombinant techniques. The plasmids encoding the light and heavy chains of the modified murine αhGPR87 IgG1 antibody (331CL) were procured from Creative Biolabs and produced in DH5α E. coli cells in the presence of the antibiotic carbenicillin, collected and purified, and sequenced to confirm the plasmid integrity had been maintained. The antibody was produced with the Expi293 mammalian cell expression system (Gibco) with the heavy chain to light chain plasmids maintained at a 1:2 ratio for transfection. The transfection protocol provided by the manufacturer was used, and unmodified and antibodies were collected on day 7 following transfection. The culture was centrifuged and the supernatant collected and purified with a rProtein A column (Cytiva). An optimized buffer system (high pH and high salt concentration) was employed to facilitate the use of a Protein A column despite the decreased affinity of Protein A for mouse IgG1 antibodies. A mild pH buffer (pH 5.5) can be used to elute the antibodies from a Protein A column whereas for a Protein G column one must use harsh pH (pH 2.5) conditions for elution. The 331CL-CCK antibody was produced, approximately 10 mg/L, with high purity and low endotoxin content. Similar yields were achieved with either a Protein A or Protein G column, indicating the Protein A column affinity is acceptable. The 331CL antibody was also produced in the same manner. Confirmation of the addition of the CCK peptide tails onto the heavy chains was done with a reducing SDS-PAGE and comparing the native 331CL to the 331CL-CCK (FIG. 1A). There is a slight increase in MW for the 331CL-CCK heavy chain relative to that of the native antibody, without a shift in the light chain, which should be unaffected. The native antibody is produced in higher yields, indicating that there is a loss of yield in the addition of the CCK peptide "tails" onto the antibody.

The second method is used for antibodies that do not readily accommodate the addition of the peptide tails during antibody expression in mammalian systems for unknown reasons. The expression was investigated of a murine IgG2b antibody (7c5) which targets a different human receptor, dual endothelin-1/signal peptide$^{VEGF}$ receptor (DEspR), following the first method described. While the antibody 7c5-CCK was able to be produced via this method, the yield was low, <1 mg/L. It is unclear why the 7c5 antibody yield was affected by the addition of the CCK tails than that of the 331CL antibody; however, it is possible that the difference in murine IgG subclass may have non-trivial significance. The murine IgG2b subclass features an additional inter-heavy disulfide linkage compared to the IgG1 subclass, which allows for less flexibility in the hinge region of the antibody. While the antibody is not modified at the hinge region specifically, the addition of the peptides may cause some unpredicted strain that can be alleviated in the IgG1 but not the IgG2b subclass.

In any case, as the yield was low, an alternative method was employed. In this method, the 7c5 antibody was expressed with a short tag on the C termini (LPETGGWSHPQFEK (SEQ ID NO: 70)) which is comprised of a Sortase A recognition sequence (LPETG (SEQ ID NO: 48)) followed by a streptactin binding sequence (GWSHPQFEK (SEQ ID NO: 61)). The Sortase A enzyme recognizes the LPETG (SEQ ID NO. 48) sequence, cleaving between the T and G residues, and facilitates the ligation following the threonine residue of any peptide featuring a pentaglycine N terminal motif. The result after the Sortase A enzymatic reaction is an antibody with the tag (LPETGGGGG (SEQ ID NO. 50)) followed by the CCK peptide sequence. The 7c5-CCK antibody was purified via a Protein A column and any unmodified 7c5-sortase antibody was removed via a Streptactin column as the unmodified antibody retains the streptactin binding sequence. As shown in FIG. 1B, the 7c5-CCK antibody was produced and purified in this manner and similarly displays a distinctive shift in the heavy chain MW as compared to the native 7c5 antibody due to the CCK peptide addition.

Synthesis and Characterization of Fluorophore Labeled Peptide

With the αGPR87-CCK antibody produced in good yield, the next step was to develop a method for conjugating desirable moieties such as fluorophores, drugs, aptamers, etc, onto the CCE peptide. The peptide itself is produced via solid phase synthesis (Abclonal) and therefore was not limited to endogenous amino acids. By utilizing an unnatural amino acid, it was ensured that the loading is bio-orthogonal and therefore does not preclude the use of any endogenous residues within a drug linker or any other structures one may want to incorporate in the future. Additionally, many chemotherapeutics are costly, and it is preferable to use low excess of such materials. Finally, the final product must be biocompatible. Therefore, a coupling method was wanted that had high efficiency without the need for use of highly toxic catalysts. Copper-free click chemistry was chosen as it is highly efficient, requires no catalyst, can proceed under biological conditions, and is bio-orthogonal. In order to facilitate this type of reaction, the amino acid N-ε-azido-lysine was utilized, which does not inhibit solid phase synthesis and is easily incorporated into the peptide sequence. The resulting CCE peptide sequence is then as follows: MK-LEEIVSE-LEEIVSE-LEEIV(K-azido)E-LEEIVYE-VGER (SEQ ID NO: 3). The azido lysine residue undergoes strain-promoted azide-alkyne cycloaddition with dibenzocyclooctyne (DBCO) labeled moieties to produce the labeled peptides. For example: the CCE peptide in PBS pH 7.4 was reacted with 1.5 eq of DBCO-Alexa Fluor 647 (Click Chemistry Tools) dissolved in minimal DMF for 1 hour at room temperature. The labeled peptide was then purified via three times through 7 kDa MWCO desalting columns to exchange into nanopure water, and then lyophilized and stored at −20° C. Peptide purity was assessed via RP-HPLC with a representative chromatogram shown in FIG. 2. The CCE peptide alone (black solid and dotted lines) shows no absorbance in the 648 nm channel and has a retention time of approximately 12 minutes. The Alexa Fluor 647 labeled CCE peptide (CCE-AF647, blue solid and dotted lines) demonstrates strong absorbance in the 648 nm channel and a shift in retention time to approximately 10 minutes, indicative of the polar nature of the fluorophore and the corresponding effect on the overall polarity of the peptide-fluorophore conjugate. Control chromatograms of fluorophore alone after purification confirm that the unreacted fluorophore is largely removed via the desalting columns. The split peaks of the peptide on HPLC are consistently observed with every DBCO labeling of the peptide and do not correspond to different molecular weights, as labelings of the peptide with DBCO-TAMRA have been analyzed by MALDI-TOF and only have one major species of the conjugated peptide at the expected molecular mass. It is therefore likely that these are 1,4-triazole and 1,5-triazole regioisomers, which are typical for copper free DBCO reactions. [2] The reaction between CCE and DBCO-AF647 requires only a slight excess of DBCO, proceeds quickly (no unconjugated CCE after 1 hour as observed by HPLC) and is purified easily with desalting columns and lyophilization.
Synthesis and Characterization of an αGPR87 Antibody Fluorophore Conjugate In order to validate the efficacy and facility of the coiled-coil based antibody conjugation method, the fluorophore labeled CCE peptide (CCE-AF647) was first used to form the antibody fluorophore conjugate (AFC). While useful in its own right for a variety of in vitro and in vivo assays, the AFC is also a significant control for investigating the stability and specificity of the coiled-coil interaction. The CCE-AF647 peptide features highly stable amide linkages between the fluorophore and the peptide. Therefore, any dissociation of the fluorophore from the antibody in the AFC construct can be largely attributed to the stability of the antibody-peptide coiled-coil complex and not the linkage between the fluorophore and CCE peptide.

First, the formation of the coiled-coil complex was confirmed and was uninhibited by either the addition of the fluorophore onto the CCE peptide or the positioning of the CCK peptides on the antibody. It was also ensured that any association of the CCE-AF647 peptide to the antibody was specific to presence of the CCK peptides and not due to any confounding ionic or hydrophobic interactions. To assess this, both the Ab-CCK as well as the native Ab were incubated, which lacks the CCK peptides, with an excess of CCE-AF647. Ab-CCK and CCE-AF647 alone were additional controls. Following a short incubation period, the samples were analyzed via size exclusion chromatography (SEC) while monitoring the absorbances at 280 nm and 650 nm for protein and fluorophore, respectively. SEC separates samples by size, with larger molecules taking a less tortuous path through the column and eluting earlier. As seen in FIG. 3, the Ab-CCK alone elutes at around 6 minutes and has no corresponding absorbance at 650 nm. The CCE-AF647 alone, being a much smaller molecule, elutes much later (between 10-12 min) and has a strong absorbance at 650 nm. There are seemingly two populations for the peptide. The peptide is highly negatively charged; however, it also features many hydrophobic residues. It is possible that at higher concentrations the peptide will aggregate to bury those hydrophobic residues, but this aggregation is likely highly unfavorable due to the abundance of negative charges. The peptide largely exists as a monomer, as seen by the difference in peak heights between the larger MW (10 min) and smaller MW (11 min) peaks. Incubation of the native antibody with the CCE-AF647 peptide demonstrated no association between the peptide and the antibody, as evidenced by the lack of a corresponding 650 nm signal for the antibody at 8 min and no effect on the peak heights corresponding to the CCE-AF647 peptide from 10-12 min. However, when the Ab-CCK and CCE-AF647 peptide are incubated together, the antibody now has a corresponding 650 nm signal at 6 min, indicating formation of the AFC. Furthermore, the two peaks of the CCE-AF647 peptide previously observed are now a single peak at 11 min and with decreased height. Not only does this indicate that a proportion of the CCE-AF647 peptide is now associated with the antibody, but also that whatever larger aggregate species of the peptide previously present was not stable, and it was highly preferable to form the AFC as a means of burying the hydrophobic residues.

While the results from this experiment were indicative of the system working appropriately, there were a few significant pieces of data that were unexpected. The native antibody elutes at 8 min, whereas the Ab-CCK antibody elutes earlier at around 6 min. (FIG. 4A) The peptide tails on the antibody contribute around 8 kDa to the overall antibody size, which is approximately 150 kDa. This difference in size alone does not account for such a difference in retention time, even taking into consideration how the tails may affect the hydrodynamic radius of the antibody as well. In fact, by utilizing a standard curve, it was determined that the Ab-CCK typically exhibits a size of about 945 kDa when analyzed by SEC, which is approximately 6 times the expected molecular weight. This is due to the peptide tails. The "hexamer" formed was consistent across many batches of Ab-CCK, different periods of incubation at 4° C., and was also observed with the 7c5-CCK antibody. The hexameric structure is not apparent from SDS-PAGE analysis. Different buffers with additives of arginine and glutamic acid were investigated and citrate phosphate buffer at pH 7.3 induced a second peak of smaller MW (still larger than the expected 150 kDa of an antibody) to appear, however it did not resolve the issue entirely. However, it could be seen from the same AFC specificity study, that there are essentially three populations of AFC that arise of approximately 945, 460, and 190 kDa, which correspond to approximately 6, 3, and 1 antibody populations, respectively. (FIG. 4B) It seems that whatever hexameric structure exists can be disrupted and replaced by the "correct" supramolecular assembly with the CCE-AF647 peptide. It is important to note however, that all three populations have a corresponding 650 nm absorbance, indicating that the hexamer structure does not preclude association with the CCE-AF647 peptide.

Using the AFC, it was investigated further how the distribution of the populations could be manipulated, with the intent of driving all the populations to the monomeric AFC. One thought was that the CCE-AF647 peptide complex with the CCK peptide on the antibody should be the most thermodynamically stable and therefore given enough time the monomeric AFC population would dominate. However, this did not end up being the case. When forming the AFC, it was incubated with 10 eq of the CCE-AF647 peptide. It was then investigated whether increasing equivalents of CCE-AF647 would change the distribution of populations. As seen in FIG. 4C, increasing equivalents had a minimum effect on the populations, slightly decreasing the amount of hexameric AFC and converting to monomeric AFC, with the trimeric AFC remaining the dominant species. Buffer and incubation temperature were also explored. The rationale was that a citrate phosphate buffer was able to help dissociate some of the hexameric antibody into the trimeric species and therefore would be beneficial for the AFC. Additionally, it was thought the hydrophobic nature of the peptide tails that was causing aggregation and that increasing the incubation temperature could help decrease the strength of that association, allowing for the coiled-coil formation to occur properly. In FIG. 4D, the difference between a 1:1 mixture of citrate phosphate buffer (CP) and PBS and PBS alone is clear and indicates that citrate phosphate buffer is a better buffer for the formation of monomeric AFC. More prominent, however, is the difference between the incubations at room temperature and 50° C. Incubation at the higher temperature resulted in the monomeric AFC becoming the dominant species in both buffer systems. Different lengths of incubation at 50° C. were investigated as well, but beyond 1 hour there did not seem to be any significant improvement. In summary, the method for formation of the monomeric AFC is in a citrate phosphate buffer pH 7.3, incubated at 50° C. for 1 hour prior to purification. Purification was done via 50 kDa MWCO spin filters for a minimum of three washes to remove excess CCE-AF647 peptide. The fluorophore to antibody ratio was monitored via UV-Vis analysis (Nanodrop) to determine how many washes were necessary.

With an optimized protocol for AFC production, the stability of the AFC in both human and murine plasma over the course of 4 weeks was investigated. Based on several reported studies of ADCs [1, 3-5], ADC concentrations in plasma in vivo over a week after single injections doses of 3-20 mg/kg can vary between approximately 0.3 to 10 µg/ml. The AFC was minimally diluted to 10 µg/ml in either human plasma, Balb/c mouse plasma, or PBS and incubated the samples with gentle shaking at 37° C. for 0 hours, 4 hours, and 1, 2, 3, 7, 14, and 29 days as shown in FIG. 5. Samples as well as the stock AFC solution were flash frozen and stored at −80° C. until further analysis. A custom indirect ELISA was utilized which consisted of the following layers: GPR87 antigen was plated overnight on Nunc Maxisorp plates and after washing, wells were blocked with 5% BSA in PBS. Samples were then incubated and detected by an HRP labeled αAlexaFluor647 antibody followed by read out with ABTS solution. Thus, the intact AFC was detected as only the intact AFC will both recognize the plated GPR87 antigen and be recognized by the αAlexaFluor647 antibody. Samples were diluted to within the dynamic range of the ELISA and compared to a standard curve generated from the same batch of AFC used for the study to ensure no batch to batch variability biasing results. Additionally, all samples were normalized to their corresponding 4-hour time point (day 0) to account for any pipetting errors when assembling the samples. The PBS samples contained minimal concentrations of AFC and this was due to the lack of blocking proteins and therefore loss of the low concentration of AFC on the sides of the Eppendorf tubes. The plasma samples on the other hand were close to the expected concentration of 100 ng/ml (ranging between 88 and 113 ng/ml) after dilution and demonstrated high stability of the AFC complex over the 4 weeks, with both human and mouse plasma samples showing no statistically significant difference between day 1 and day 29 of incubation. The coiled-coil complex is therefore stable over a month at 37° C. in the presence of both mouse and human serum proteins. Additionally, the AFC does not significantly aggregate or fall out of solution as all samples were centrifuged before analysis to remove precipitates.

Synthesis and Characterization of Drug Loaded CCE Peptide

While the AFC was useful for investigating the integrity of the coiled-coil complex because of the highly stable linkage between the fluorophore and the CCE peptide, the design of the linkage was considered between a highly potent chemotherapeutic and the peptide for the ADC. There are various linker chemistries for ADCs in use clinically and being investigated, as described in Chapter One. A common motif in ADCs is the valine-citrulline dipeptide which is recognized by human Cathepsin B, a lysosomal enzyme. The full motif typically used is valine-citrulline-p-aminobenzylcarbamate-monomethyl auristin E (vc-MMAE). The p-aminobenzyl carbamate group undergoes a 1,6-elimination after cleavage by Cathepsin B, releasing the highly potent microtubule inhibitor monomethyl auristatin E (MMAE). The vc-MMAE structure is used in several FDA approved ADCs (brentuximab vedotin, polatuzumab vedotin, enfortumab vedotin) which target both hematologic and solid tumors. Furthermore, MMAE demonstrated high potency in preliminary studies of toxicity in human NSCLC lines NCI-H520 and NCI-H226, with $IC_{50s}$ of 42 and 294 pM, respectively, therefore it was decided to proceed with this structure.

Another consideration was the model. The efficacy of the ADC in a murine model was evaluated. It was reported by Anami et al. that while the valine-citrulline motif is stable in human blood, it is degraded by murine extracellular carboxylesterases, decreasing in vivo stability in murine models. [1] They reported the addition of a glutamic acid, creating the tripeptide glutamic acid-valine-citrulline (EVC), stabilized the structure in mouse blood while still being recognized by murine and human Cathepsin B. Therefore, this sequence was utilized in the design to ensure increased stability of the drug linker in the murine model. To facilitate conjugation with the CCE peptide, the molecule was capped with a DBCO moiety.

Figure 6:
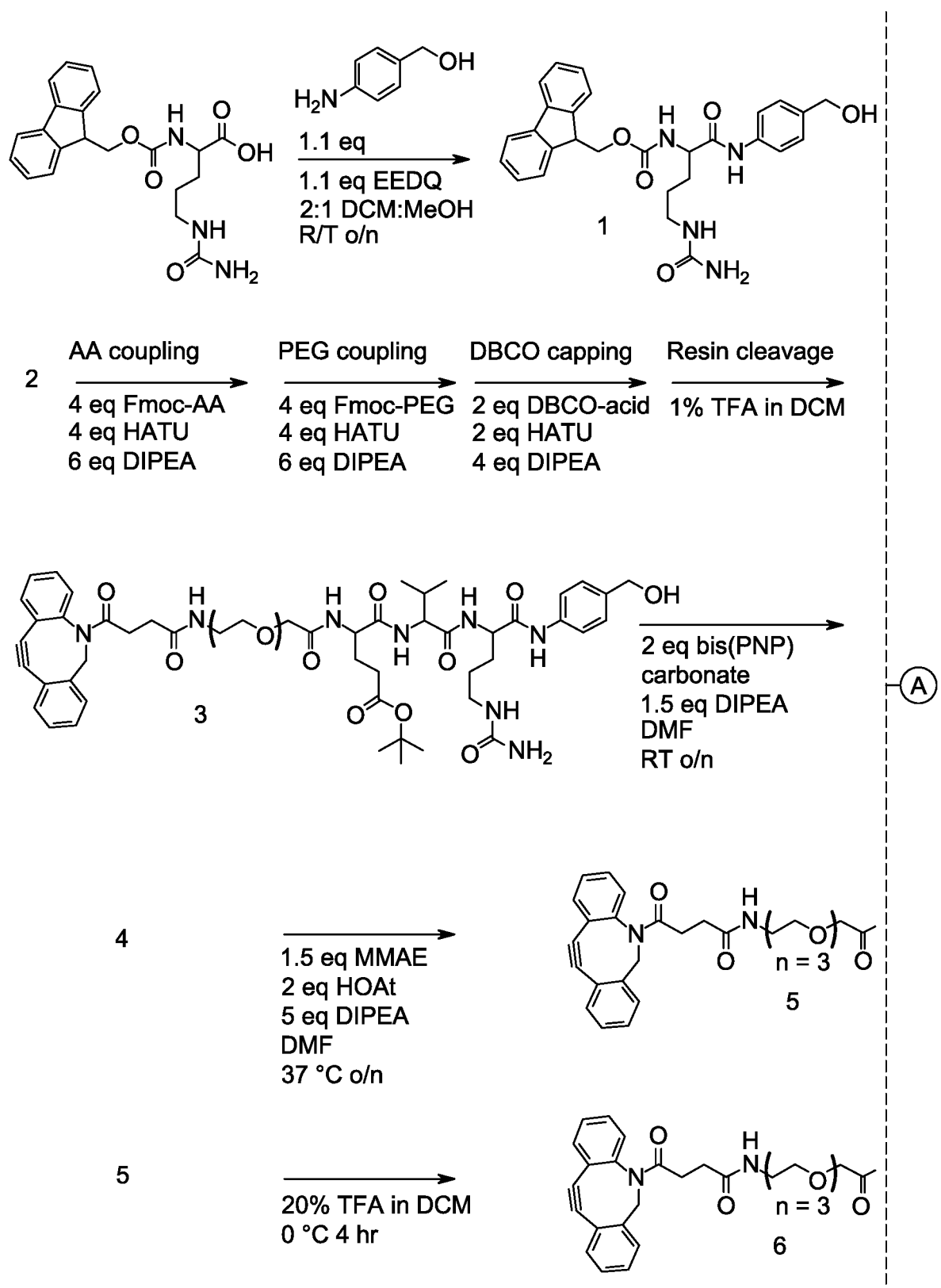
FIG. 6 is a synthesis protocol for the molecule DBCO-PEG3-glutamic acid-valine-citrulline-p-aminobenzylcarbamate-MMAE (DBCO-MMAE) as adapted from Anami et al.
Figure 6:
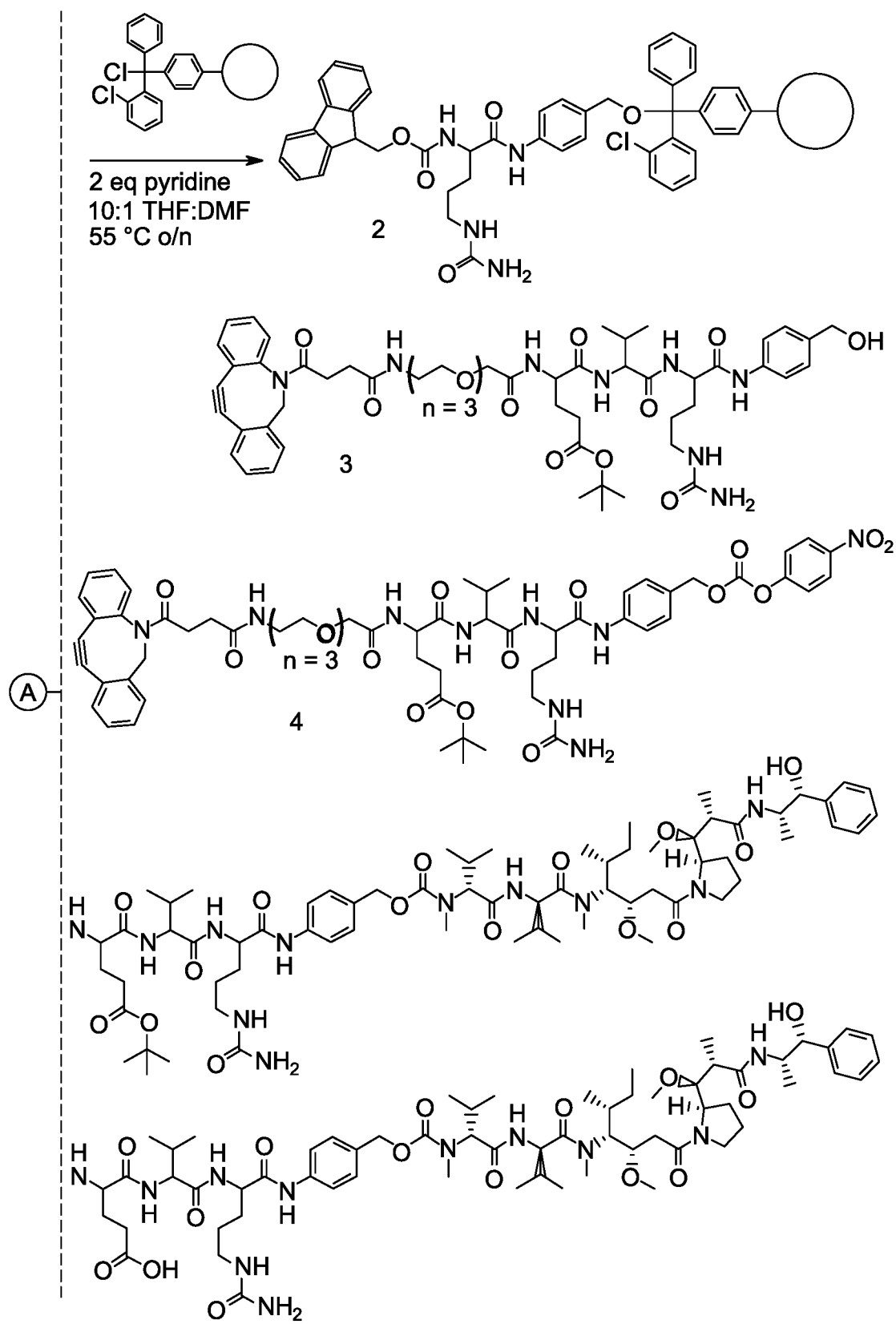

A small amount of the glutamic acid-valine-citrulline tripeptide was synthesized. It was originally attempted to react DBCO-N-hydroxysuccinimidyl ester with the N-terminus of the tripeptide and was largely unsuccessful, likely due to steric hinderance between the bulky DBCO group and the tert-butyl protecting group on the glutamic acid side chain. Insertion of a short PEG spacer resolved this issue and has the added benefit of enhancing the solubility of the hydrophobic MMAE. Therefore, the final structure of the drug-linker is DBCO-PEG3-EVC-PABC-MMAE, as shown in FIG. 7A. The solution phase synthesis of the full DBCO labeled drug molecule (DBCO-MMAE) has been developed, which will be able to produce the drug molecule on a large scale. However, for proof of concept, only a small amount (on the order of milligrams) of the DBCO-MMAE molecule is necessary. A modified synthesis procedure was utilized from Anami et al., as shown in FIG. 6. [1]

Briefly, this method utilizes solid phase synthesis with Fmoc/piperidine chemistry to construct the molecule DBCO-PEG3-E(t-butyl)VC-PABOH. Following preparative HPLC purification, the p-aminobenzyl alcohol is converted to an activated carbonate. Here the procedure was modified, activating the alcohol with bis(4-nitrophenyl)carbonate overnight and purifying via precipitation in cold diethylether. This was found to improve the yield of the activated molecule over purification with prep-HPLC. The molecule was then reacted with MMAE to form a carbamate linkage to the monomethylamino group of MMAE. Finally, the glutamic acid was deprotected and purified with prep-HPLC, in which both the final product and undeprotected product could be collected. Identity of the final DBCO-MMAE product was confirmed by both $^1$H NMR and MALDI-TOF. (FIG. 7B).

The DBCO-MMAE was surprisingly water soluble and therefore the reaction with CCE in PBS was allowed to proceed. DBCO has a strong absorbance at 310 nm that decreases following reaction with azide, allowing us to monitor the kinetics of the reaction by the change in absorbance at 310 nm. However, whereas the previous reaction with DBCO-AF647 was rather quick and proceeded in under 1 hour, the reaction with DBCO-MMAE proceeded much more slowly. (FIG. 7A) By fitting the decrease in absorbance at 310 nm, the half-life was found of the DBCO-MMAE reaction to be approximately 52 min. This is due to the solubility of the DBCO-MMAE in a completely aqueous solution, as it is more hydrophobic than DBCO-AF647.

Figure 7C:
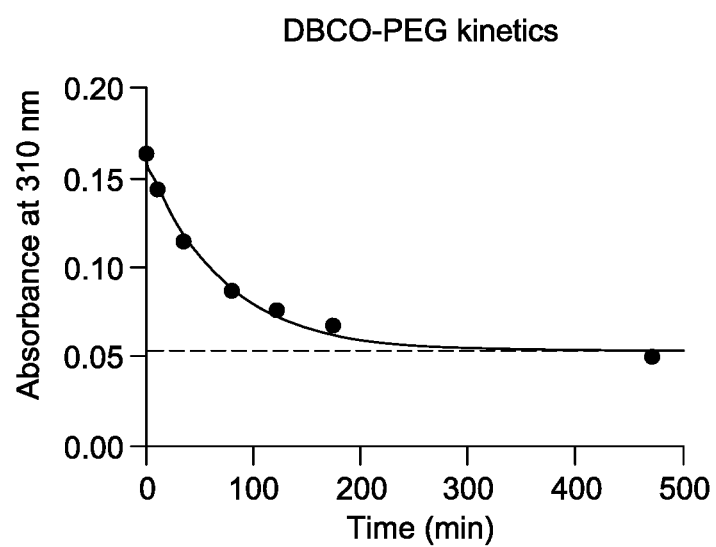

However, a stock solution of DBCO-AF647 in DMF was utilized which could influence the solubilities as well. The kinetics were characterized of the DBCO-AF647 further by rerunning the AF647 conjugation in an aqueous environment. Surprisingly the reaction that previously was so quick, was much slower, with a half-life of around 194 min. However, in an effort to keep the concentration of the reaction in a range where the fluorophore absorbance was not saturated so as to function as an internal standard, the reaction was run at a much lower concentration (0.24 mg/ml peptide). The reaction was rerun at a similar concentration as the CCE-MMAE reaction (0.66 mg/ml peptide). This time the half-life was 73 min, more similar to that of the CCE-MMAE reaction. More specifically however, the reaction was around 2.7 times more concentrated, and resulted in around a 2.6 times shorter half-life. So rather than the hydrophobicity, which may play a role, it seems the concentration has a larger influence on the kinetics of the reaction. Another reaction was run, this time with DBCO-PEG (MW 10 kDa) at a high concentration of 2.7 mg/ml of the peptide. However, the half-life of the reaction was still around 50 min. Therefore, there is a limit to how much the concentration of the reaction can increase the kinetics, and other factors such as relative size and hydrophobicity are still relevant. For subsequent peptide conjugations a final concentration was targeted of 1-2 mg/ml and for the DBCO-MMAE reaction it was allowed to proceed overnight to ensure the reaction went to completion. After purification with 7 kDa MWCO desalting columns, the CCE-MMAE peptide was lyophilized and analyzed by RP-HPLC. When necessary, further purification to remove unreacted peptide was done with prep-HPLC, resulting in pure CCE-MMAE, as shown in FIG. 7C.

Synthesis and Characterization of the ADC

Figure 8A:
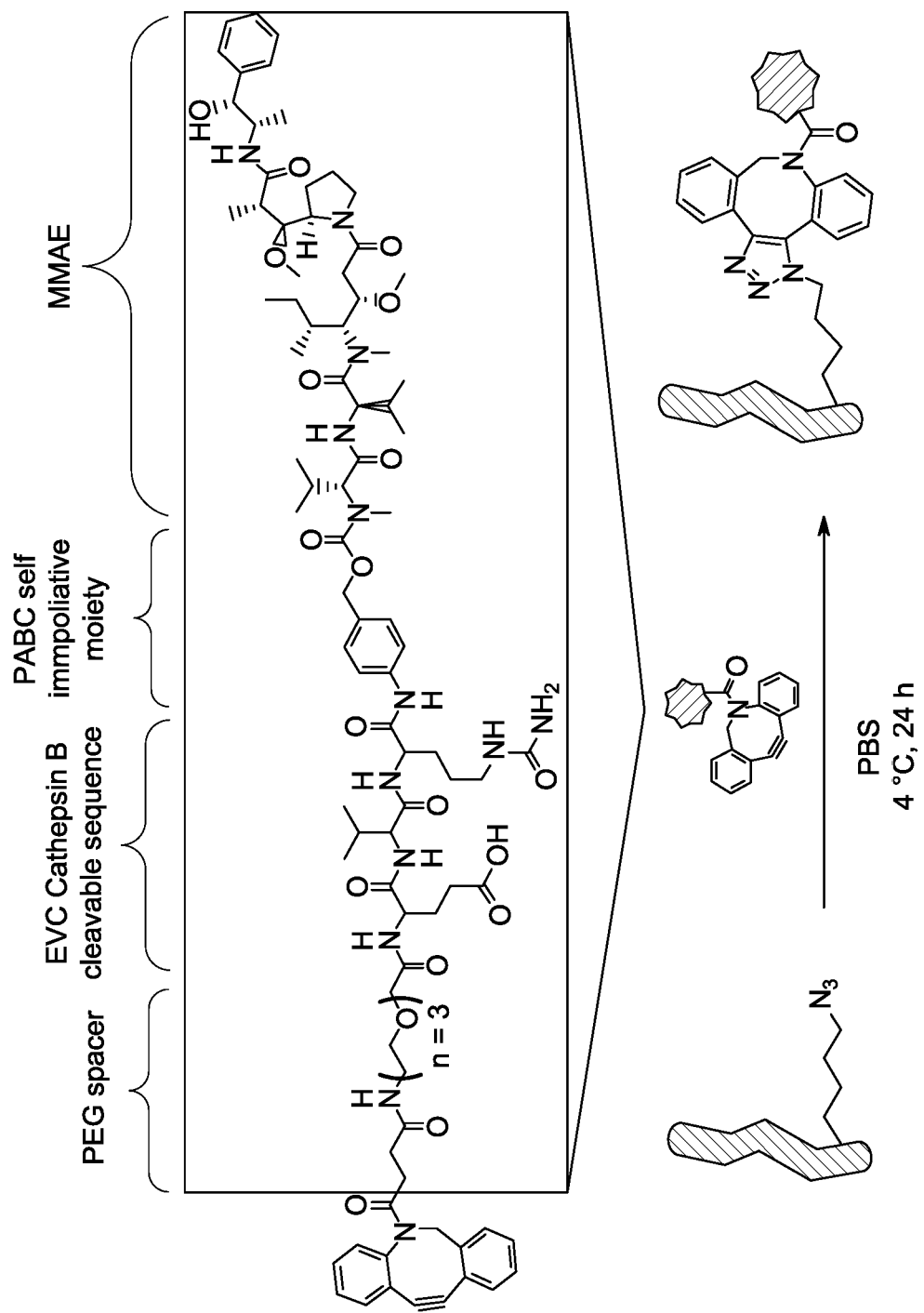
FIG. 8A is a schematic representation of the structure and components of the full DBCO-MMAE molecule.
Figure 8C:
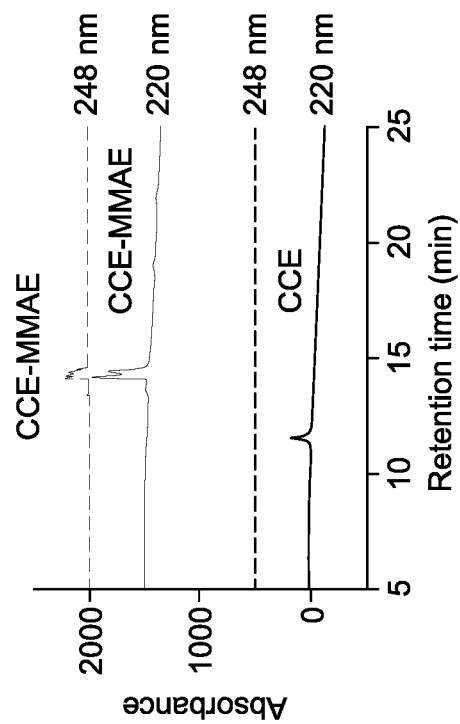
FIG. 8C is a RP-HPLC chromatograph of purified CCE-MMAE compared to CCE showing a distinctive shift in retention time and increased absorbance at 248 nm due to the addition of MMAE.
Figure 8B:
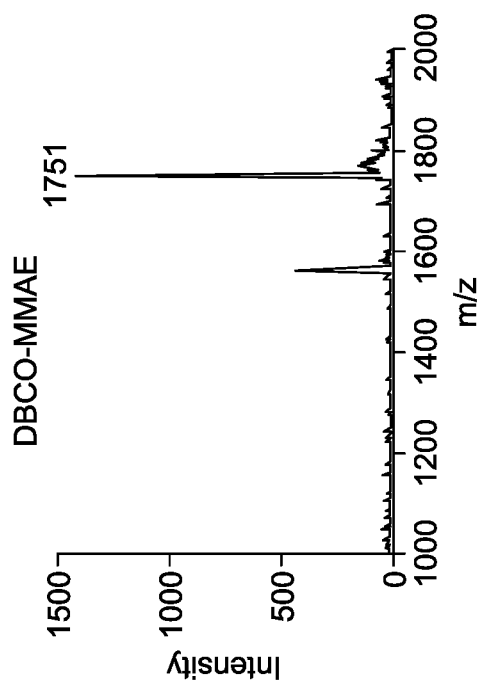
FIG. 8B is a MALDI-TOF spectrogram confirming the identity of the DBCO-MMAE molecule in combination with $^1$H NMR analysis. Expected m/z: 1729, detected m/z 1751 [M+Na]$^+$.

With the CCE-MMAE peptide successfully synthesized and previous optimization of the antibody loading process with the AFC, it was facile to translate the method to formulating the ADC. The same populations arise by SEC that were observed previously for the AFC, as shown in FIG. 8A and FIG. 8B. Using a similar custom ELISA as before, but with a secondary antibody recognizing mouse antibody, it was contemplated whether the loading of CCE-MMAE, the 50° C. incubation, or even the expression of the peptide tails affected the binding affinity of the antibody. (FIG. 8C) What was found was initially surprising, which was that by adding the peptide tails onto the antibody, the Kd was affected. Specifically, the Ab has a Kd of 0.4 nM and the Ab-CCK has a Kd of 2.8 nM. With the addition of CCE-MMAE, the Kd was about half that of the Ab-CCK, approximately 1.3 nM and not affected by temperature of incubation. This was perplexing, as it was clear adding the CCE-MMAE peptide to form the ADC did not decrease the affinity relative to the Ab-CCK antibody, but both Ab-CCK and the ADC had a decreased affinity relative to the native Ab. However, if it was taken into consideration the SEC data showing the larger aggregates formed by these antibodies, the results are more consistent. The original analysis was done by using the wt/vol concentration of the antibodies. However, if there are larger aggregates forming such as hexamers of Ab-CCK or hexamers, trimers, and monomers of the ADC, then equivalent wt/vol concentrations will vary by molarity. If it was assumed the Ab-CCK exists as a hexamer and therefore at the same wt/vol concentration as the native Ab is at one sixth the molar concentration, the binding data can be reanalyzed with these adjusted molarities. Similarly, it can be assumed the ADC is forming on average trimers and adjust the molar concentration by one third accordingly. The resulting curves are similar, with the Ab, Ab-CCK, and ADC having Kds of approximately 0.43, 0.46, and 0.41 nM, respectively. These results have the caveat that the differences are assumed to be in molarity based on SEC. However, the raw absorbances of the Ab vs. Ab-CCK show the Ab plateauing at an absorbance of around 0.8 whereas the Ab-CCK plateaus around 1.2, indicating that more secondary antibody binds Ab-CCK possibly as a result of more binding sites for the secondary antibody as a hexamer.

Conclusions

The αGPR87-CCK antibody is produced and purified in reasonable yields using a mammalian expression system and Protein A columns. The DBCO mediated conjugation of both fluorophore and drug to the CCE peptide is accomplished with low equivalents and is purified via desalting columns or prep-HPLC if necessary. The AFC and ADC are both produced by incubating Ab-CCK with an excess of appropriately labeled CCE peptide for 1 hour at 50° C. and purifying by washing with spin columns (FIGS. 9A-9B). The Ab-CCK antibody and subsequent AFC and ADC form higher order aggregates in a reliable manner. Despite forming larger order structures, the AFC shows good stability in both human and mouse plasma at 37° C. over the course of 4 weeks and the binding affinity of the ADC is unchanged from the Ab-CCK antibody and is not affected by the 50° C. incubation (FIGS. 9C-9D).

REFERENCES

1. Anami, Y., et al., Glutamic acid-valine-citrulline linkers ensure stability and efficacy of antibody-drug conjugates in mice. Nature Communications, 2018. 9(1): p. 1-9.
2. Bouvet, V., M. Wuest, and F. Wuest, Copper-free click chemistry with the short-lived positron emitter fluorine-18. 2011.
3. Gupta, N., et al., Computationally designed antibody-drug conjugates self-assembled via affinity ligands. Nature Biomedical Engineering, 2019. 3(11): p. 917-929.
4. Li, F., et al., Mouse Strains Influence Clearance and Efficacy of Antibody and Antibody-Drug Conjugate Via Fc-FcγR Interaction. 2019.
5. Sun, X., et al., Effects of Drug-Antibody Ratio on Pharmacokinetics, Biodistribution, Efficacy, and Tolerability of Antibody—Maytansinoid Conjugates. 2017.

Figure 10B:
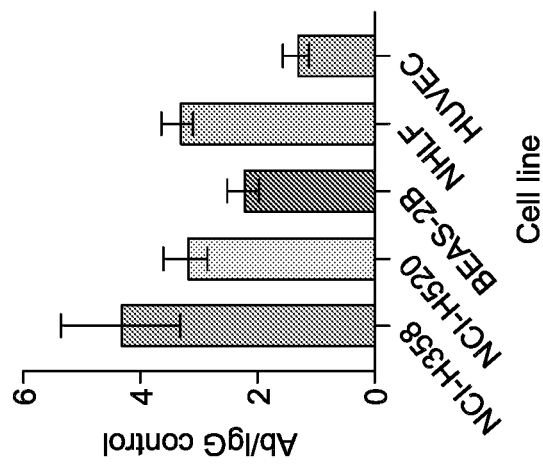
FIG. 10B is a bar graph showing flow cytometry based analysis of GPR87 expression in the NSCLC lines NCI-H358 and NCI-H520, normal human lung lines BEAS-2B (epithelial) and NHLF (fibroblasts), and normal human endothelial line HUVEC. Data are the mean fluorescence intensities of gated populations normalized to the mean fluorescence intensities of an IgG control after subtracting background fluorescence.
Figure 10A:
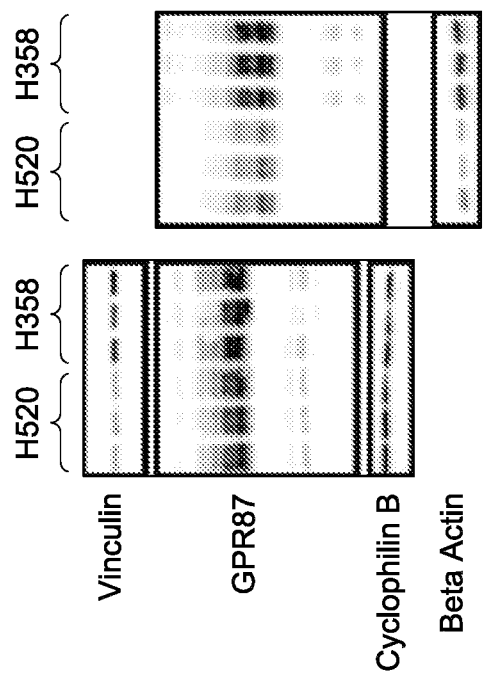
FIG. 10A shows Western blot analysis of the NSCLC cell lines NCI-H520 (H520) and NCI-H358 (H358) with staining for the loading controls vinculin, cyclophilin B, and beta actin and for GPR87.

Example 2: In Vitro and In Vivo Efficacy of αGPR87 Antibody Fluorophore and Drug Conjugates Characterization of GPR87 Expression in NSCLC Lines and Normal Human Cell Lines Via Flow Cytometry We first characterized two NSCLC cell lines that had been reported to show high mRNA expression of GPR87, the adenocarcinoma line NCI-H358 [1] and the squamous cell carcinoma (SCC) line NCI-H520 [2]. We first attempted to confirm and compare expression via Western blotting. While we were able to confirm expression, it was difficult to compare expression levels as the choice of loading control had a significant impact on the results, as seen in FIG. 10A. Additionally, there were multiple bands, some of which were also reported by the antibody manufacturer (Abcam). While it was clear both lines expressed GPR87, we were not confident from these results about the relative expression between the two lines or whether the different bands were correlated with surface expression. As surface expression levels of GPR87 are what will be relevant for our ADC, we moved forward with flow cytometry analysis. Additionally, flow cytometry data would provide us an indication of surface GPR87 expression levels normalized per cell. We also analyzed the normal human cell lines NHLF (lung fibroblasts, LONZA), BEAS-2B (lung epithelial cells, LONZA), and HUVEC (umbilical vein endothelial cells, LONZA), which were expected to have low GPR87 expression, as GPR87 has been reported to have low expression in normal lung tissues. We included the HUVEC line as the ADC will be administered intravenously, therefore it is important that it does not interact with endothelial cells.

While we have prepared an AFC that would be suitable for surface staining, we wanted to characterize the expression levels with relevant controls, in this case a non-specific murine IgG1 isotype that had the same fluorophore to antibody ratio. Therefore, for GPR87 staining we used the native αGPR87 antibody, to target the same GPR87 epitope as the ADC, and a fluorescently labeled secondary antibody. In this way we compared the mean fluorescence intensities (MFI) between the antibody and IgG control groups without concerns for differences in fluorophore to antibody ratio biasing results. All cell lines also had an unstained control to characterize the background fluorescence. For our analysis, we subtracted the unstained MFI from the samples and then normalized the Ab MFI to that of the IgG control. The results are shown in FIG. 10B, which indicate that the GPR87 expression levels are not dramatically overexpressed in the two cancer cells lines when compared to the normal lung cell lines, especially the NHLFs. This was surprising based on the literature and the tissue staining of primary patient samples in Chapter Two, where normal lung tissue had low GPR87 expression. We ran a Tukey's multiple comparisons test to determine if the differences between cell lines were significant and stratified the cell lines into "low," "medium," and "high" expression levels based on these results. HUVEC cells had low expression of GPR87 and will be considered our GPR87 "low" cell line, with BEAS-2B having "medium" expression, and NCI-H358, NCI-H520, and NHLF cell lines having "high" expression. However, these levels are only for the purposes of interpreting further in vitro assays.

Internalization of AFC in NSCLC Lines

Figure 11:
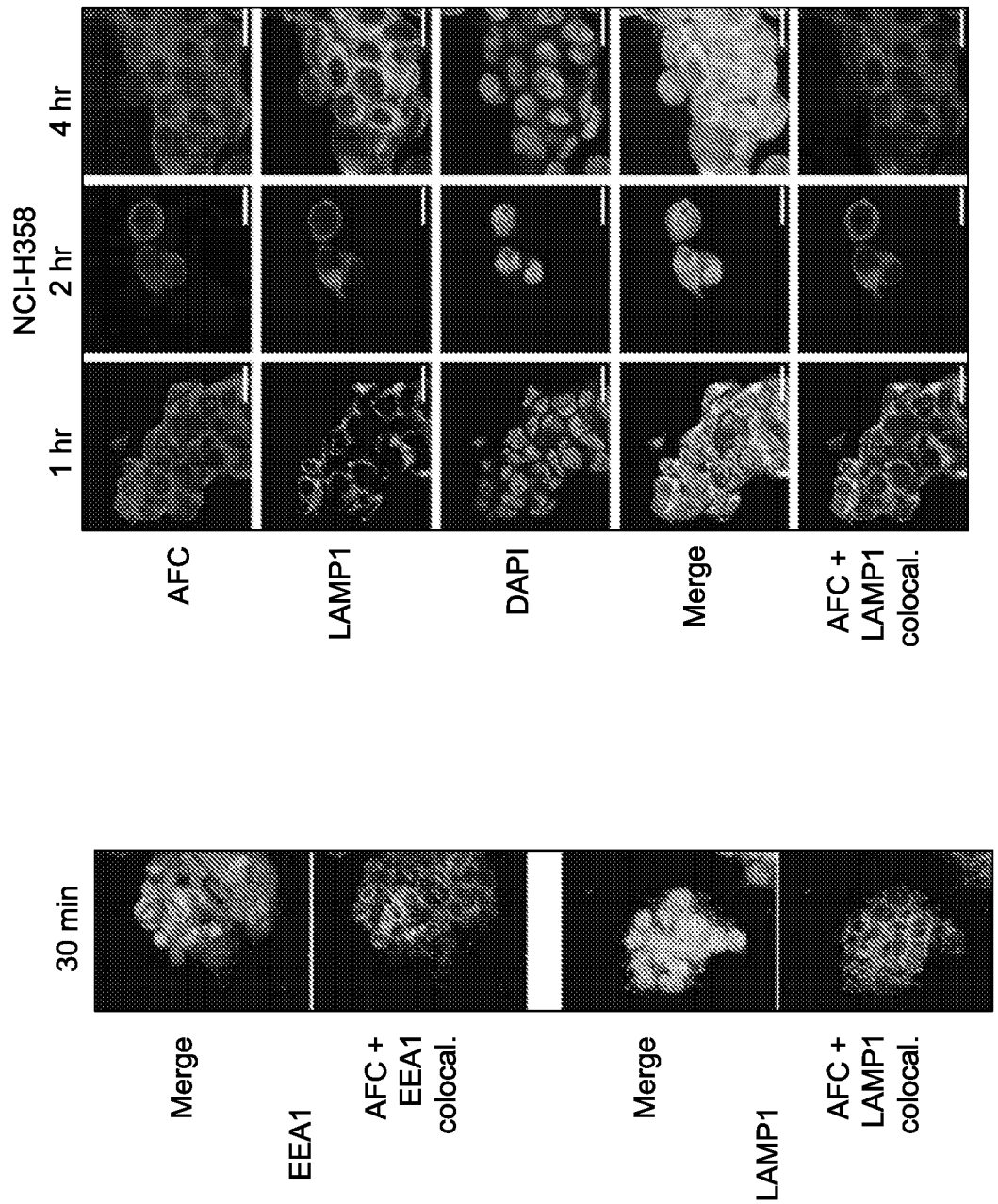
FIG. 11 are confocal images of the NCIH358 cell line after 1, 2, and 4 hours of incubation with AFC. The cells are stained for LAMP1 and with DAPI. The individual channels as well as the merged image are shown in addition to the AFC and LAMP1 channels isolated and colocalized pixels shown. Scale bar=20 µm.

The GPR87 receptor is a G-protein coupled receptor (GPCR), a class of receptors which are activated by an extracellular ligand, initiating activation of associated intracellular G proteins for downstream signaling. Following activation, GPCRs are often internalized and recycled to prevent prolonged stimulation. [3, 4] However, it has not been explicitly demonstrated previously that an αGPR87 antibody will be internalized upon binding the GPR87 receptor. Therefore, we wanted to confirm the uptake of our αGPR87 AFC in the two GPR87 high expressing NSCLC cell lines, NCI-H358 and NCI-H520. We cocultured the cells with 3 µg/ml of AFC for either 30 minutes or 1 hour and fixed and permeabilized the cells before immunofluorescently staining for either the early endosomal marker EEA1 or the lysosomal marker LAMP1. Shown in FIG. 11 are the images from these studies with the AFC signal, either the EEA1 or LAMP1 signal, and DAPI. The merged images are shown as well as the AFC and either EEA1 or LAMP1 signals merged, with colocalization. NCI-H520 appears to demonstrate some colocalization between the AFC and the early endosomal marker at both the 30 minute and 1 hour timepoints while having almost no colocalization with the lysosomal marker at 30 minutes and increased colocalization at 1 hr. This was encouraging as a demonstration of the AFC being internalized and trafficking to the lysosome over the course of an hour. However, the adenocarcinoma line NCI-H358 showed only mild colocalization with the endosomal marker at 30 minutes and 1 hour and very little colocalization with the lysosomal marker at either time point. To investigate this further, we increased the concentration of AFC to 10 µg/ml and increased the incubation times to 1, 2, and 4 hours. The resulting images showed that at 1 hour, the AFC does colocalize with lysosomes, however it also appears to be predominantly localized to what is likely the cell membrane, surrounding the lysosomes. By 2 hours, the AFC now is highly colocalized with the lysosomes and further colocalizes by the 4-hour timepoint while also showing less of a membranous staining pattern. From these analyses, we can determine that the AFC is indeed internalized by the human NSCLC cancer cell lines NCI-H520 and NCI-H358, albeit with different apparent kinetics.

In Vitro Cytotoxicity of the αGPR87ADC in NSCLC and Normal Human Cell Lines

Figure 12C:
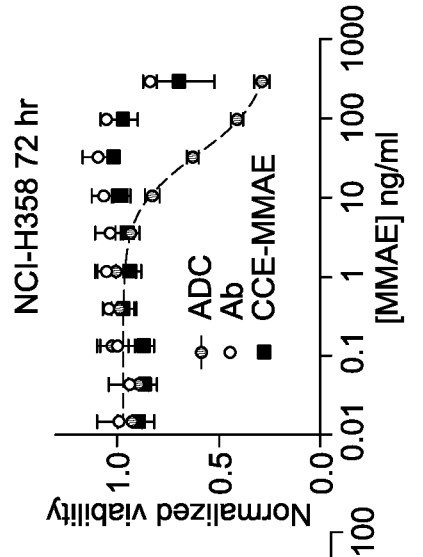
FIGS. 12A-12C are graphs showing the cytotoxicity of an exemplary ADC of the disclosure in NIH-3T3 cells compared to equivalent MMAE and antibody concentrations over 72 hours (FIG. 12A), in NCI-H358 cells either with 72 hours of incubation or 24 hours of incubation followed by fresh media and another 48 hours of incubation without treatment (FIG. 12B), in NCI-H358 cells compared to equivalent antibody or CCE-MMAE controls over 72 hours (FIG. 12C).
Figure 12B:
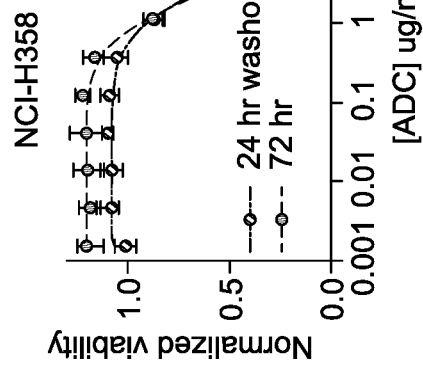
Figure 12A:
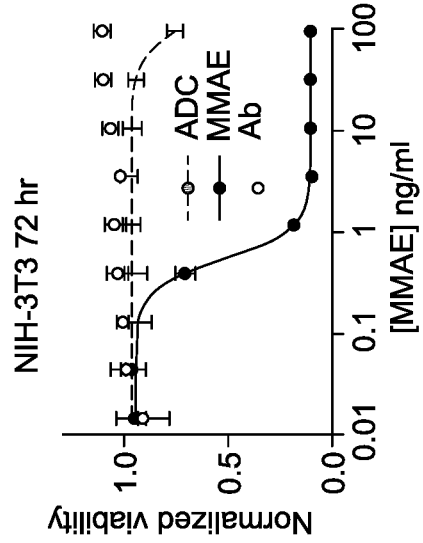
Figure 12F:
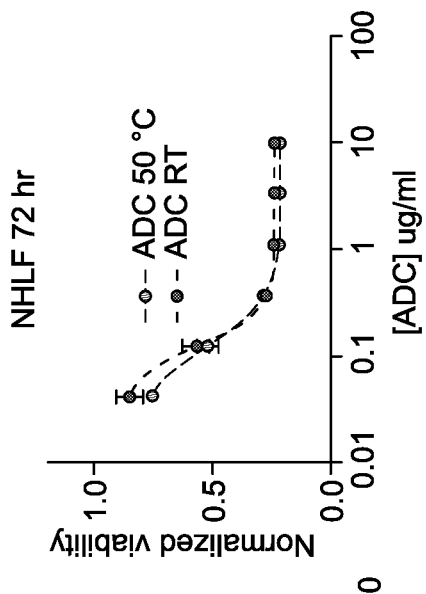
FIGS. 12D-12F are graphs showing the cytotoxicity of ADC prepared at either 50° C. or room temperature (RT) in NCI-H520 (FIG. 12D), in BEAS-2B (FIG. 12E) and in NHLF (FIG. 12F) cell lines.
Figure 12E:
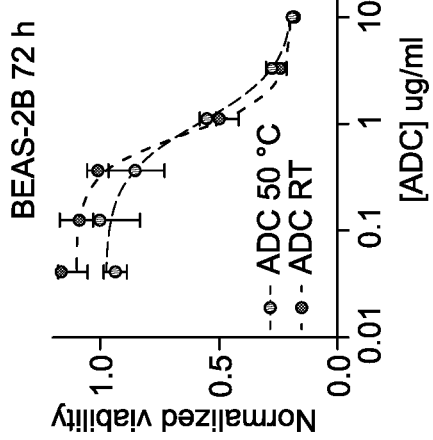
Figure 12D:
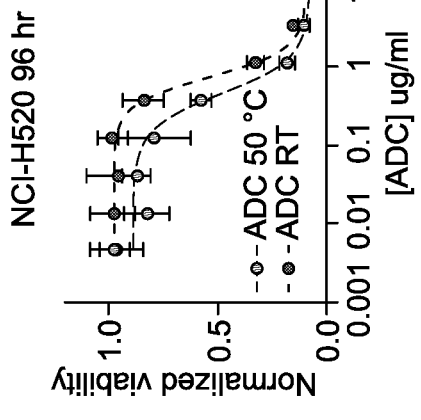
Figures 13E, 14:
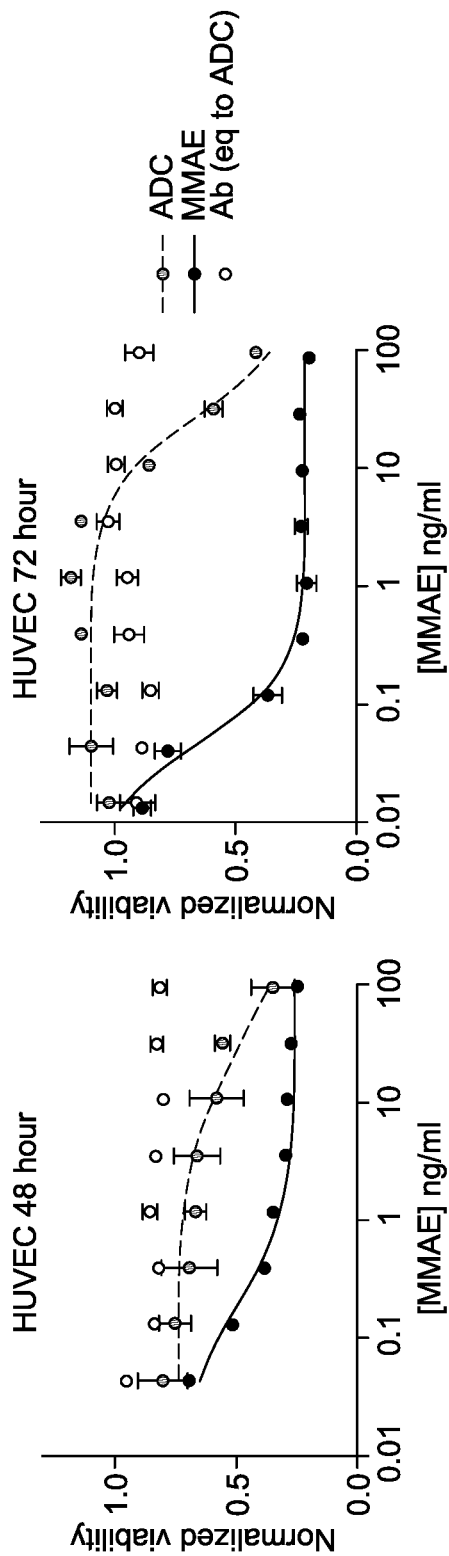

We next investigated the efficacy of the ADC in vitro in the NSCLC cell lines NCI-H358 and NCI-H520, normal human lung lines NHLF and BEAS-2B, and normal human endothelial cell line, HUVEC. The murine fibroblast line NIH-3T3 was our negative control, as the αGPR87 antibody does not recognize the murine GPR87 epitope. We incubated NIH-3T3s with up to 10 µg/ml of ADC (67 nM, equivalent to 96 ng/ml of MMAE) along with the native antibody and MMAE alone at equivalent concentrations. As expected, the antibody and ADC did not show any significant cytotoxicity except for the highest dose of ADC (~76% viability at 10 µg/ml) which is likely due to nonspecific uptake. (FIG. 12A) The equivalent dose of MMAE, on the other hand, was highly toxic, indicating the MMAE is successfully linked to the ADC. We next investigated the toxicity in a GPR87+ cell line, NCI-H358. We utilized two different incubation methods. For one set of cells, we incubated with ADC for 24 hours before removing the media and replacing with fresh media containing no treatment. These cells were then incubated for a further 48 hours, resulting in a total incubation period of 72 hours (FIG. 12C). The control cells were incubated with ADC for the entire 72 hours. (FIG. 12B) We found no significant difference between the two treatment groups, indicating that internalization of the ADC occurs within the first 24 hours, in good agreement with the internalization data presented in Section One. We next interrogated whether the CCE-MMAE peptide alone could account for the toxicity we observed and compared the ADC to equivalent concentrations of antibody and CCE-MMAE. Toxicity was only observed at the highest concentration of CCE-MMAE, equivalent to the 10 µg/ml ADC dose, which again may be due to non-specific uptake. It is not equivalent to the toxicity observed with the ADC, therefore we do not suspect the ADC-peptide coiled-coil complex is dissociating during incubation in media and that the antibody targeting component of the ADC is necessary for its toxicity. We also confirmed that the incubation at 50° C. during ADC formulation does not affect the potency of the attached MMAE, having already confirmed that incubation temperature does not affect the binding affinity of the antibody in Chapter Four. We tested three different lines, an SCC line, NCI-H520, and two normal cell lines, BEAS-2B and NHLF, with ADC prepared at both 50° C. and room temperature (RT). (FIGS. 12D-12F) We observed the largest difference between the $IC_{50s}$ in the NCI-H520 line, 3.0 nM vs 4.9 nM for 50° C. and RT, respectively. In the BEAS-2B cell line, the difference in $IC_{50s}$ was decreased and in the opposite direction, 6.8 nM vs 5.3 nM for 50° C. and RT, respectively. In the NHLF line the $IC_{50s}$ were identical, 0.8 nM. The differences between the two ADC formulations did not follow a trend and were minor, additionally the maximal efficacies (i.e. lowest viabilities) were the same between both formulations. From these results, we concluded that the 50° C. incubation did not significantly affect the potency of the ADC.

We then incubated the human cell lines with ADC, and equivalent concentrations of MMAE and native Ab for both 48 hours and 72 hours, the results of which can be seen in FIG. 13A-13E. We expected the results to correlate with the GPR87 expression we observed by flow cytometry. For the normal cell lines, this was the case. As detailed in FIG. 14, the line that was most sensitive to the ADC were the NHLFs, followed by the BEAS-2Bs, and the line with the lowest GPR87 expression, the HUVECs, had the highest $IC_{50}$ after 72 hours. However, both the NSCLC cell lines had relatively high $IC_{50s}$ given the GPR87 expression status of these lines.

What can also be observed from the table is that the difference between 48 and 72 hour $IC_{50s}$ is the smallest for the NHLFs, being almost identical. In comparison, NCI-H358 and NCI-H520 see approximately a 4-fold or 2-fold decrease in $IC_{50}$, respectively, between the two time points. On the other hand, the NCI-H520 line has almost a 10-fold increase in MMAE $IC_{50}$ at 72 hours compared to 48 hours. The results are likely because the cell lines are different sizes and morphologies and therefore are at different confluencies when plated at the same number of cells per well and are therefore likely to be in different parts of their log growth phase during treatment. For example, the NSCLC lines are typically at very low confluency at a plating density of 5,000 cells per well and may not reach log phase growth until later in the assay. As MMAE affects actively dividing cells, this will affect the results of the assay. While 72 hours was not the optimized end time point for all five cell lines, in order to have a standardized cell plating density, and therefore same ADC:cell ratio, going past 72 hours for some of the cell lines would lead to confluency or death in untreated control cells, which would also confound results. Thus, we incubated the two NSCLC lines for longer periods of time to allow the control cells to become more confluent by the assay endpoint, and to see how this would affect the ADC $IC_{50}$. (FIGS. 15A-15B) We found the $IC_{50s}$ for NCI-H520 decreased over time, from 12.87 to 5.24 ng/ml of MMAE equivalent ADC and stayed similar for NCI-H358, from 9.11 to 8.69 ng/ml of MMAE equivalent ADC.

We investigated analyzing other parameters, such as the area under the curve (AUC) for the five cell lines as we noted that the hill slope was variable between different cell lines and between ADC and MMAE treatments. By assessing the AUC, we could interpret the total cytotoxicity of the treatment over all concentrations tested. Those results are reported in FIG. 16. Rather than the large (>100) fold differences in ADC and MMAE $IC_{50s}$ observed in FIG. 14, FIG. 16 indicates the difference in toxicity between the two are less pronounced, on the order of 1-3-fold difference. However, comparing the toxicity of the ADC across the cell lines, the relationships, or lack thereof, between toxicity and GPR87 expression remain largely the same.

Figures 17A, 17B, 18:
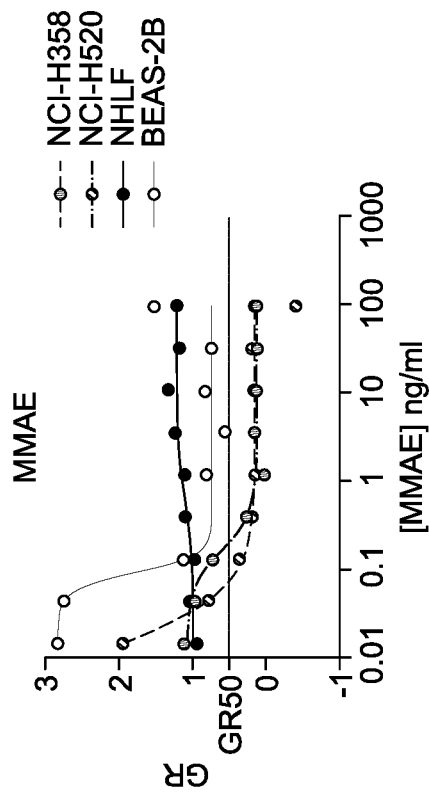
FIGS. 17A and 17B are GR plots for NCI-H358, NCI-H520, NHLF, and BEAS-2B cell lines for ADC (FIG. 17A) and MME (FIG. 17B). A dotted line is plotted indicating where the GR$_{50}$ value is calculated.
FIG. 18 is a table showing the GR$_{50}$ values for the various cell lines as calculated from FIGS. 17A and 17B for either the ADC or MMAE. GR$_{50}$ values are expressed as ng/ml of MMAE.
Figure 19A:
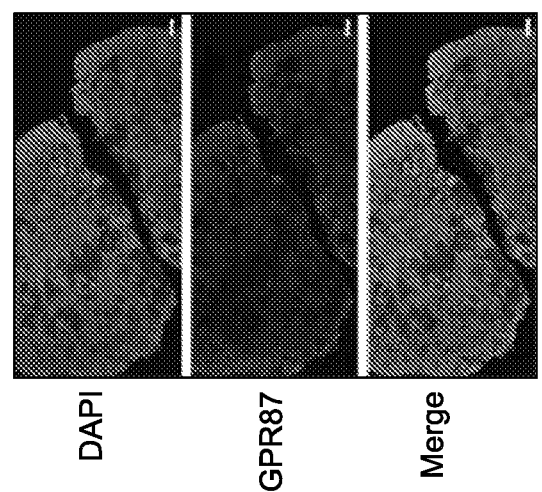
FIG. 19A are photographs showing immunofluorescent staining for GPR87 in a stage 4 mucinous lung adenocarcinoma PDX tumor. DAPI is shown, GPR87 is shown and the merge image is also shown. Scale bar=100 µm.
Figure 19B:
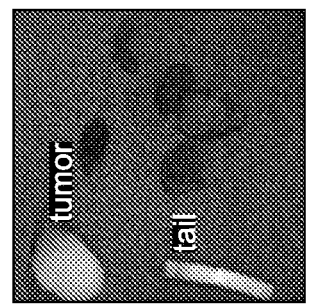
FIG. 19B is a photograph showing fluorescent imaging of tail, tumor, and major organs collected from a PDX tumor bearing mouse 24 hours following injection of the AFC. Signal is primarily seen in the tail (injection site) and the tumor.

Standard cytotoxicity assays, like the MTT assays ran here, measure or rather, approximate the cell number at an end point and compare to control untreated cells. Effectively what is measured is a comparison between growth rates. When comparing the efficacy of a drug, particularly a mitotic inhibitor, among different cell lines, division rate differences due to biology, media additives, or seeding density can have a dramatic effect on the $IC_{50}$, an issue brought up by Hafner et al. [5] They reported with both modeling and in vitro assays how using the $IC_{50}$ as a metric can actually mask the true mechanism of a drug, for example the microtubule inhibitor paclitaxel. They suggest instead utilizing the parameter normalized growth rate inhibition (GR). GR values indicate whether a drug inhibits growth (0<GR<1), is cytostatic (GR=0) or cytotoxic (GR<0). To calculate this parameter, one needs cell count data for at least two different time points and compares experimental growth rates to the growth rate of control cells. From this data the $GR_{50}$, or the concentration at which the growth rate of treated cells is half that of control cells, can replace $IC_{50}$. They found that the $GR_{50}$ was a more robust parameter than $IC_{50}$, including in the case of paclitaxel, and able to replicate in vivo efficacy patterns more effectively. Consequently, we reviewed the data at our two time points to perform a similar analysis. We plated at the same seeding density for both the 48 and 72 hour time points. As MTT is an endpoint assay rather than a kinetic assay like MTS, we can use MTT signal as a proxy for cell count. The only cell line where the MTT data did not seem to fit this assumption were the HUVEC cells, which appeared to decrease in viability in the control wells between 48 and 72 hours. Therefore, we excluded this cell line from our analysis. The results from our GR50 analysis are plotted in FIGS. 17A-17B and tabulated in FIG. 18. We are technically assessing the effect the ADC or equivalent MMAE has on the growth rate of cells at 60 hours, as we are measuring at t=x±delta t, with x being 60 and delta t being 12 hours. Ideally, we would assess an earlier time point or even multiple time points. However, even from this data, we see that GR agrees with what is observed experimentally. The $IC_{50s}$ were unchanged between 48 hours and 72 hours in NHLF because at 60 hours both the ADC and MMAE essentially had no negative effect on growth rate (GR≥1), resulting in relative viability graphs that are almost identical. (FIGS. 19A-19D). Conversely, both NCI-H520 and NCI-H358 are cytotoxic (GR<0) at higher concentrations of ADC at this time point. For the NSCLC lines, both the ADC and MMAE have a measurable GR50, whereas the NHLFs do not reach that value. In the BEAS-2B line however, the ADC and not MMAE is cytotoxic at 60 hours and in fact the $GR_{50}$ cannot be calculated for MMAE in this cell line. We do note that while the other three lines at least doubled in cell count between 48 and 72 hours, the BEAS-2B line only increased by 1.4 fold. While the $GR_{50}$ data is still not in agreement with GPR87 expression, it does indicate that this type of analysis at other, earlier, time points is useful in assessing the dynamics of ADC and MMAE cytotoxicity in these cell lines.

Preliminary In Vivo Analysis of AFC Clearance and Biodistribution

We had access to a stage four mucinous lung adenocarcinoma patient derived xenograft (PDX) model. We assessed the GPR87 positivity in the tumor and found it to be positive for GPR87. (FIG. 19A) We ran a preliminary study using the AFC to determine whether the AFC would traffic to the tumor in vivo. Twenty-four hours following injection in the tail at 2.5 mg/kg, the tail, tumor, and major organs were collected and imaged with an IVIS system. The tail (injection site) and tumor both showed high fluorescence, with little fluorescence in the major organs. (FIG. 19B) We moved forward with a preliminary study of the AFC in PDX tumor bearing NSG mice. Four mice were injected with 10 mg/kg of AFC once the tumor reached approximately 200-300 mm³ and blood was drawn at 4 hours, 3 days, and 2 weeks. The mice were intended to be kept for 2 weeks, but one animal had to be euthanized at day 3 due to tumor size. At the 2-week time point, we euthanized the other animals and harvested the organs. The plasma and organ AFC levels were analyzed by a custom ELISA which detects intact AFC, as described in Chapter Four. The results are seen in FIG.

20A. The AFC appeared to be rapidly cleared. We also ran an ELISA with an anti-mouse IgG secondary to determine the total Ab concentrations and assess whether the AFC was being cleared or was not stable (FIG. 20B). The Ab readout detected a higher concentration of Ab than AFC, however, the general trend of clearance is maintained. The concentration even by 3 days is markedly low for our AFC. Whereas we detect <1 µg/ml of AFC at 3 days by either AFC or Ab readout, levels above 10 µg/ml have been reported with similar ADC DAR ratio (~2) and dose (10 mg/kg). [6] However we are utilizing NSG mice to facilitate the PDX model. It has been reported that NSG mice have enhanced clearance rates of both antibodies and ADCs. [7] However, even in comparison to the clearance rates in NSG mice noted by Li et al., AFC clearance is fast.

We also analyzed the organs at the 3 day and 2 week time point with an ELISA (FIGS. 20C-20D). These results are preliminary and require a higher n to determine the biodistribution of the AFC. The concentration of the AFC is highest in the tumor at 3 days and at 2 weeks compared to liver, kidney, spleen, heart and lung (FIG. 20C).

Conclusions

We completed a full pharmacokinetic study with non-tumor bearing NSG mice at 10 mg/kg where we compared the clearance rates of the AFC to the native antibody to assess whether the coiled-coil conjugation method is resulting in faster clearance rates or whether it is the NSG model. We assessed efficacy of a single injection of the ADC in the PDX model compared to saline, native antibody, and a standard of care chemotherapeutic (paclitaxel). MMAE alone was not used as it is prohibitively toxic and is not used clinically for this reason.

REFERENCES

1. Kita, Y., et al., Inhibition of Cell-surface Molecular GPR87 With GPR87-suppressing Adenoviral Vector Disturb Tumor Proliferation in Lung Cancer Cells. Anticancer Res, 2020. 40(2): p. 733-741.
2. Glatt, S., et al., hGPR87 contributes to viability of human tumor cells. Int J Cancer, 2008. 122(9): p. 2008-16.
3. Calebiro, D. and A. Godbole, Internalization of G-protein-coupled receptors: Implication in receptor function, physiology and diseases. Best Pract Res Clin Endocrinol Metab, 2018. 32(2): p. 83-91.
4. Pavlos, N. J. and P. A. Friedman, GPCR Signaling and Trafficking: The Long and Short of It. Trends Endocrinol Metab, 2017. 28(3): p. 213-226.
5. Hafner, M., et al., Growth rate inhibition metrics correct for confounders in measuring sensitivity to cancer drugs. Nat Methods, 2016. 13(6): p. 521-7.
6. Sun, X., et al., Effects of Drug-Antibody Ratio on Pharmacokinetics, Biodistribution, Efficacy, and Tolerability of Antibody-Maytansinoid Conjugates. Bioconjug Chem, 2017. 28(5): p. 1371-1381.
7. Li, F., et al., Mouse Strains Influence Clearance and Efficacy of Antibody and Antibody-Drug Conjugate Via Fc-FcgammaR Interaction. Mol Cancer Ther, 2019. 18(4): p. 780-787.

Example 3

Figure 21A:
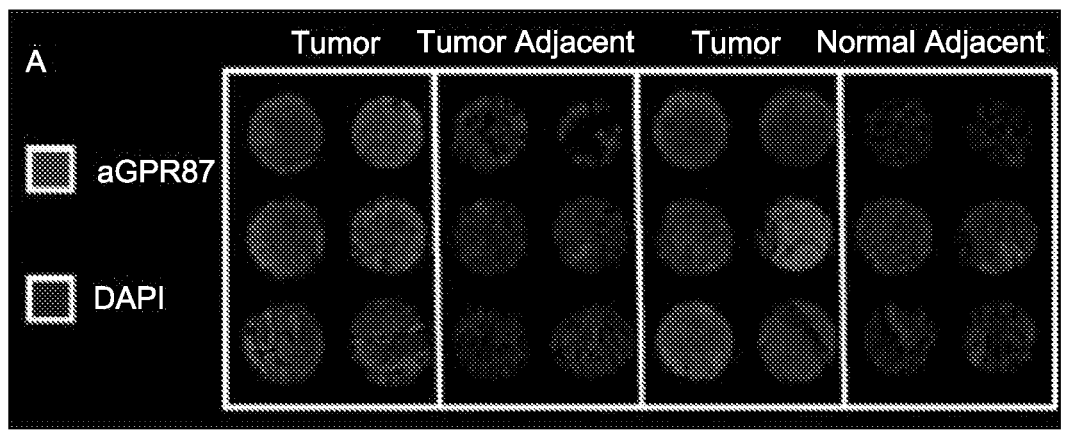
FIG. 21A depicts immunohistochemical staining of primary lung patient tumor and matched adjacent tissue samples for GPR87 counterstained with DAPI for nuclear staining.
Figure 21B:
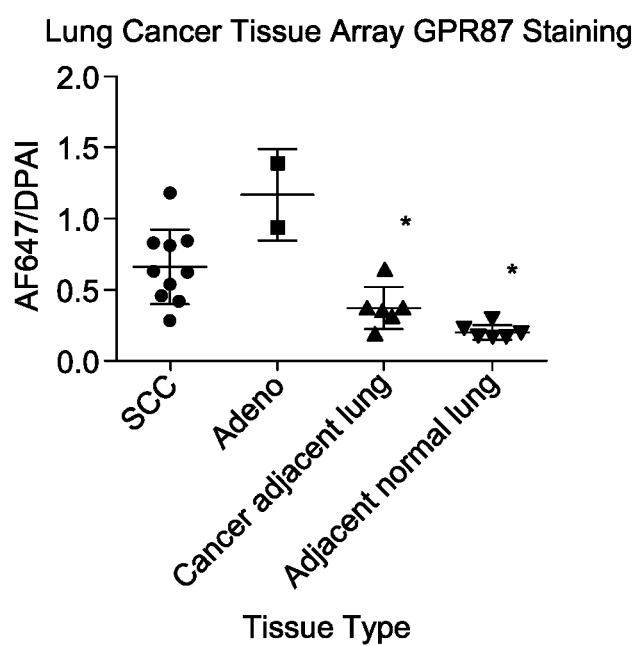
FIG. 21B is a graph showing AlexaFluor 647 signal (AF647) normalized to DAPI signal for each sample and both cancer adjacent tissue and normal adjacent tissue showed significantly ($p<0.05$) less staining for GPR87.

In this study, we describe an additional antibody formulation that targets the G coupled protein receptor GPR87, which has been shown to be overexpressed in many squamous cell carcinomas such as those of the lung, head and neck, as well as pancreatic cancer. In FIG. 21A-21B, we investigated the expression of GPR87 in lung cancer patient samples and saw significantly higher staining for the receptor in the tumor samples compared to matched tumor adjacent (<1.5 cm away from margin) or normal adjacent (>1.5 cm away from margin) samples.

The antibody can be modified to contain the docking peptide sequence appended onto the C termini of the heavy chains via a pentaglycine spacer. This is achieved by inserting the pentaglycine spacer and receiving peptide sequence (MK(LKKIKSV)$_4$VGER, SEQ ID NO: 69) into the heavy chain plasmid using typical molecular biology techniques. The light chain plasmid of the antibody remains the same. Both plasmids are grown and purified from DH5α E. coli and then used to transiently transfect Expi293 cell cultures, after which the antibody is purified from the culture supernatant using Protein A chromatography.

Herein we additionally describe another method of conjugating drug to the docking peptide. The docking peptide sequence is as follows: MK(LEEIVXE)$_4$VGER (SEQ ID NO: 2), where X is either serine, tyrosine, or a 6-azido-lysine in different combinations. For example, one iteration of the docking peptide sequence may follow the sequence MK(LEEIVSE)$_2$LEEIVK-azidoELEEIVYEVGER (SEQ ID NO: 3) with serine in the X position for the first two repeating heptads, followed by 6-azido-lysine and then tyrosine. The serine residue serves as a hydrophilic amino acid which is significant for coiled-coil formation. The tyrosine serves as both an aromatic amino acid for quantification of the peptide at 280 nm and as a reactive moiety for 4-phenyl-1,2,4-triazole-3,5-dione (PTAD) based chemistry while the 6-azido-lysine serves as a reactive moiety for bio-orthogonal "click" chemistries such as copper-catalyzed alkyne chemistry or copper-free dibenzocyclooctyne (DBCO) or bicyclo[6.1.0]nonyne chemistries.

As such, the linker between the active agent to be delivered (such as drug, siRNA, enzyme, etc) is designed to accommodate the different coupling techniques. The core part of the linker comprises of a valine-citrulline dipeptide, which is cathepsin B cleavable. However, this can be modified to be degradable by other enzymes, such as matrix metalloproteinases, or under other conditions such as high glutathione conditions (disulfide linkages), acidic conditions (hydrazone linkage), etc. In the case of a cathepsin B cleavable linker the dipeptide can also be replaced with a tripeptide, glutamic acid-valine-citrulline, to enable stability in murine studies, as shown by Anami et al in 2018. A para-aminobenzyl alcohol group can also be incorporated to allow for its self-immoliative properties, enabling release of free active agent after enzyme cleavage. The active agent, such as a highly potent chemotherapeutic such as mertansine or monomethylauristatin E (MMAE), can be coupled to the alcohol of the para-aminobenzyl group to form a thiocarbonate (with a thiol containing molecule, like mertansine) or carbamate (with an amine containing molecule, like MMAE). The N-terminus of the enzyme cleavable peptide sequence can be modified with a short polyethyleneglycol (PEG) spacer and then capped with either 4-phenyl-urazole or DBCO, allowing for conjugation to the docking peptide of the coiled coil. An example of such a linker design is shown in FIG. 22, comprising of DBCO, PEG, tripeptide EVC, PABC, and MMAE.

Figure 22:
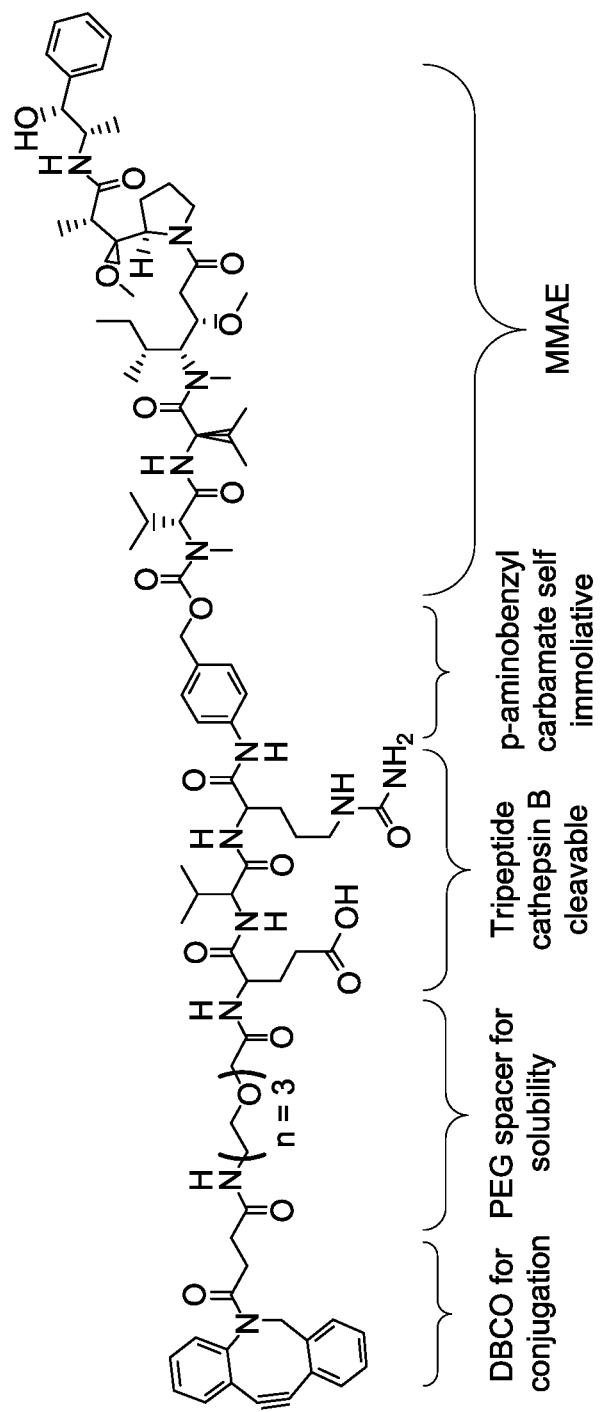
FIG. 22 depicts a representative example of the linker chemistry, comprising of DBCO for copper-free click chemistry with the 6-azido-lysine on the docking peptide, PEG as a short spacer to improve DBCO coupling as well as to improve solubility of highly hydrophobic drugs, tripeptide EVC which is a cathepsin B cleavable sequence that is stable in murine blood, PABC as a self-immoliative moiety, and MMAE as the active agent of interest.
Figure 23:
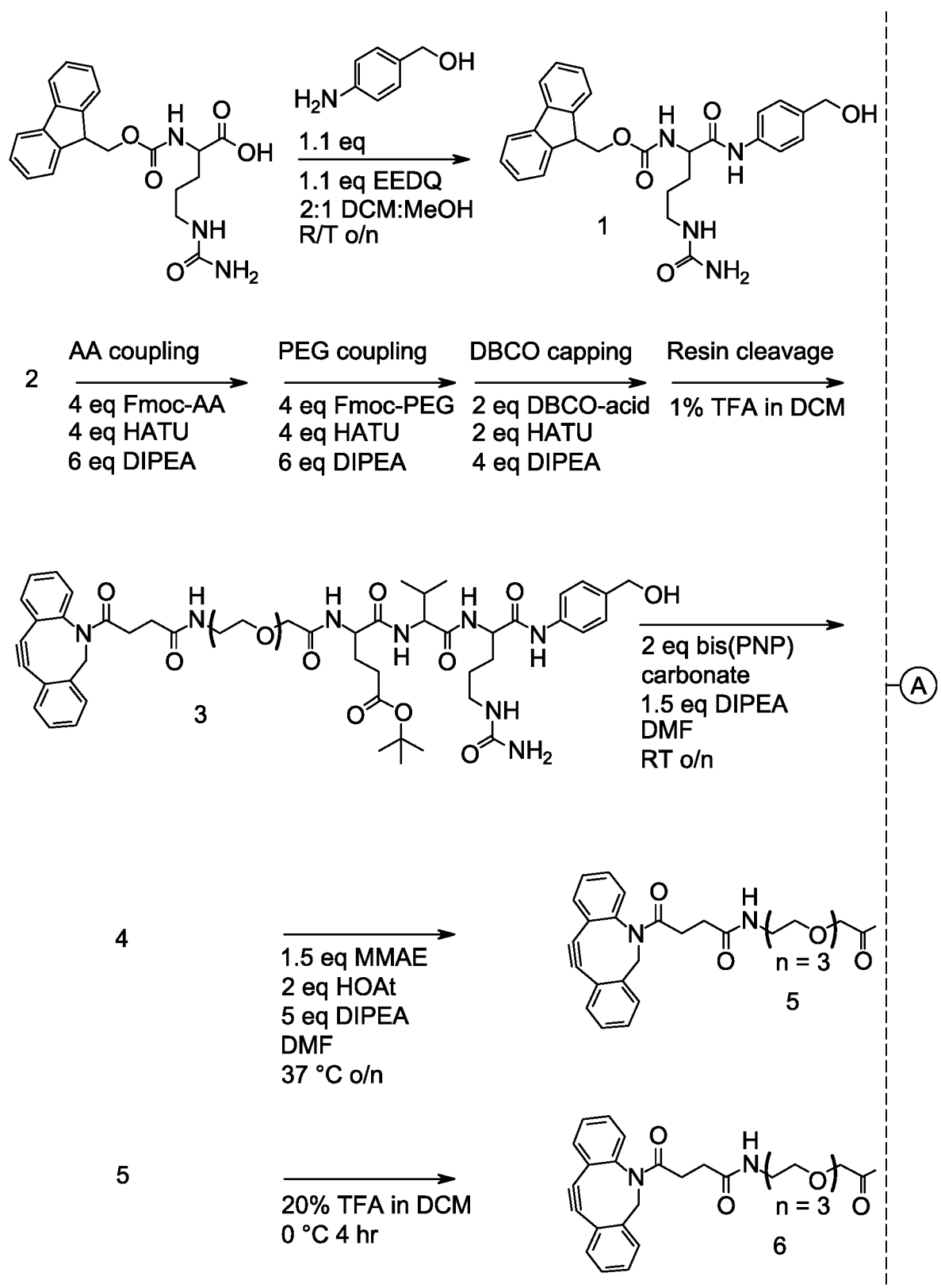
FIG. 23 is an exemplary synthesis scheme for the synthesis of the exemplary linker shown in FIG. 22 which utilizes solid phase synthesis. Briefly, fmoc-citrulline is coupled with para-aminobenzyl alcohol and then loaded onto a 2-chlorotrityl chloride resin. Valine, then 5-tert-butyl ester glutamic acid, then NH2-PEG(3)-CH2COOH are added following typical Fmoc/piperidine based chemistry. The linker molecule is then capped with DBCO-acid and cleaved from the resin using 1% TFA in DCM. The linker alcohol is reacted with bis(paranitrophenol) carbonate to form an activated carbonate and then reacted with MMAE. The final deprotection of the tert-butyl ester is then performed and the molecule purified via prep HPLC.
Figure 23:
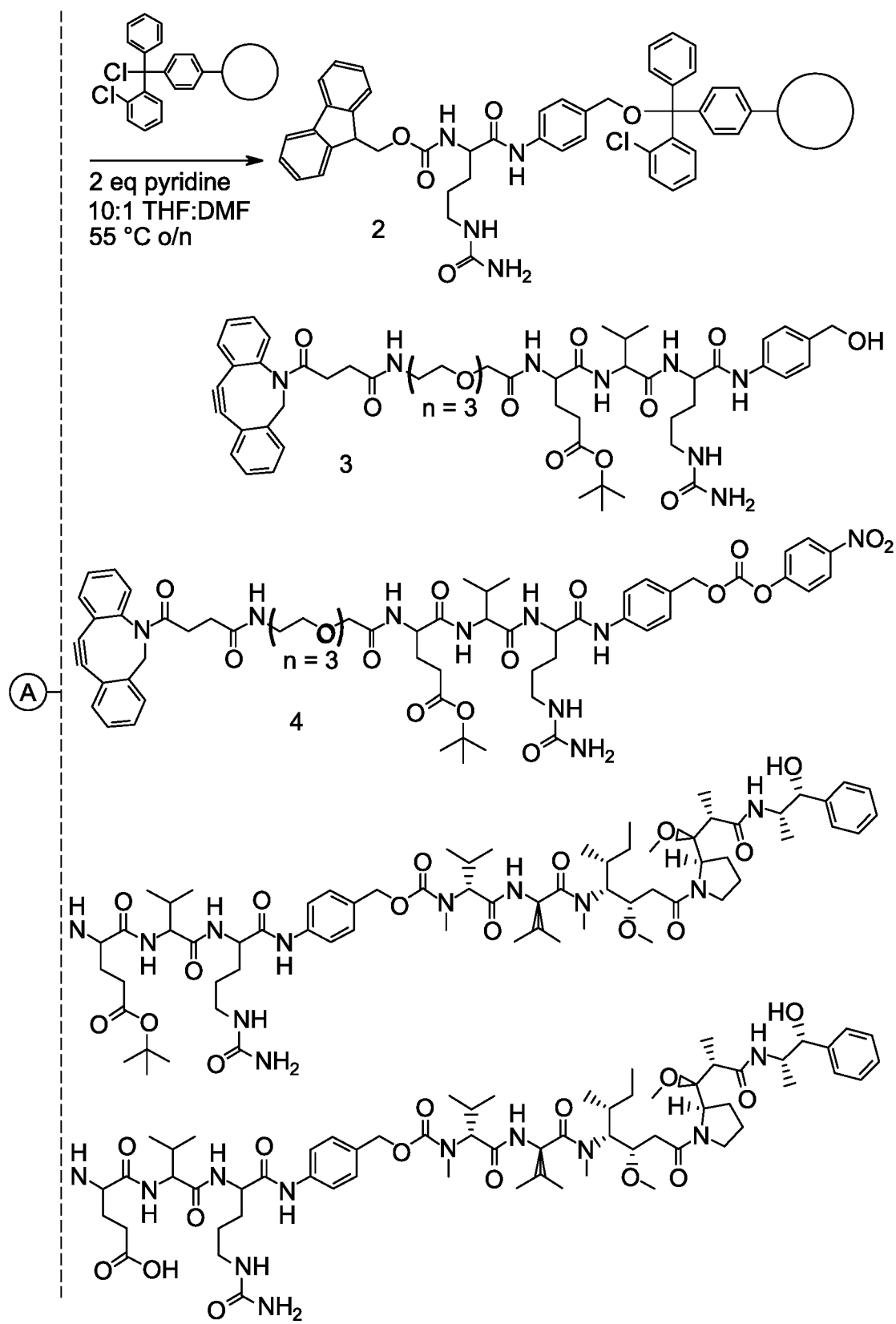

We have devised two synthetic schema for the linker-drug molecule shown in FIG. 22. One method is modified from Anami et al and follows a solid-phase synthesis based route, shown in FIG. 23 and was able to produce pure product as shown in FIG. 24A-24C by $^1$H NMR, HPLC and MALDI analysis. This method is limited in the yields produced and therefore a second method, using solution phase synthesis has also been developed.

Figure 25:
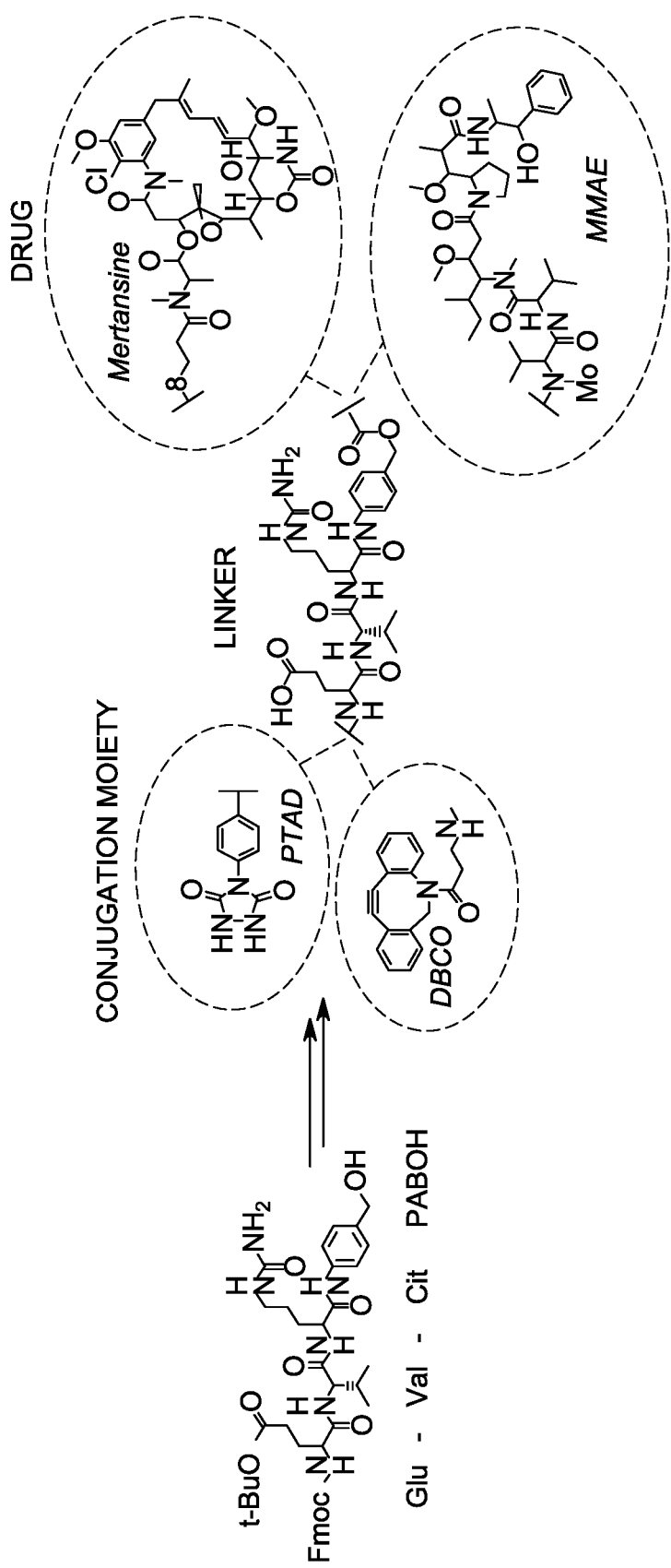
FIG. 25 depicts exemplary versatile linker functionalization strategy with representative examples of payloads (mertansine or MMAE) and conjugation moieties (DBCO or PTAD) on the cathepsin B cleavable peptide Glu-Val-Cit stable in murine blood and bearing PABC as a self-immoliative moiety.

The solution phase synthesis was designed with a versatile and scalable strategy, allowing functionalization with a variety of payloads (mertansine and MMAE) and conjugation moieties (PTAD or DBCO) as described in FIG. 25. The synthesis in solution allows the isolation of the synthetic intermediates and thus optimization of each step, as well as purification by silica gel chromatography or precipitation, suitable for multi-gram scale synthesis.

Figure 26:
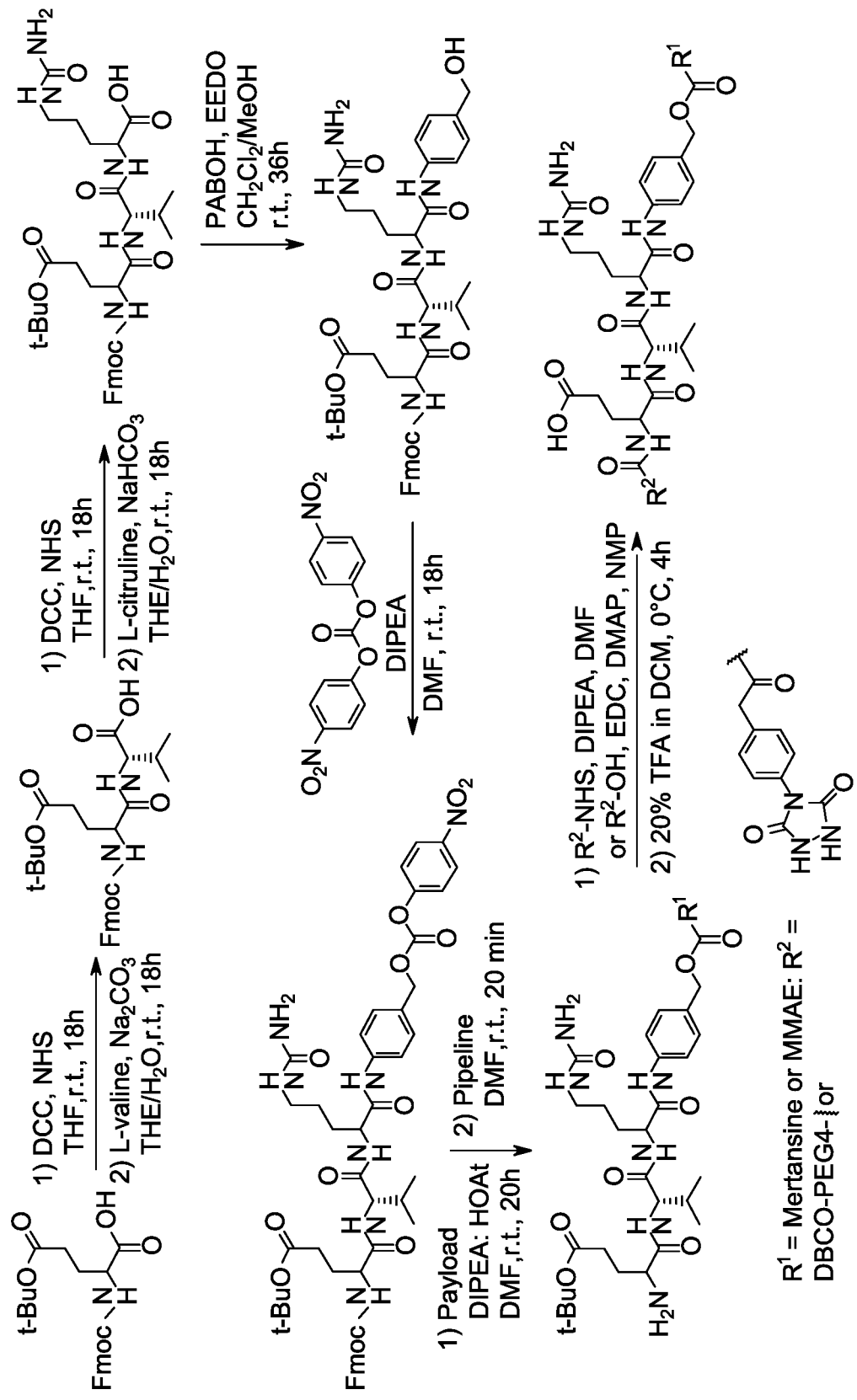
FIG. 26 is a synthesis scheme for the structures shown in FIG. 25. Briefly, tert-butyl ester protected fmoc-glutamic acid is activated as an NHS ester before addition of valine in basic aqueous conditions, and the dipeptide product is purified by silica gel chromatography or by precipitation. Citrulline is added following the same strategy and the tripeptide intermediate is purified by precipitation. It is then coupled with para-aminobenzyl alcohol, reacted with 4-nitrophenyl chloroformate and the activated linker is purified by silica gel chromatography or precipitation before further functionalization. The payload is added in basic conditions before Fmoc deprotection. DBCO or PTAD moieties are then reacted either as an NHS-ester activated acid or a carboxylic acid bearing. The final deprotection of the tert-butyl ester is finally performed and the molecule purified via prep HPLC or precipitation.
Figure 27A:
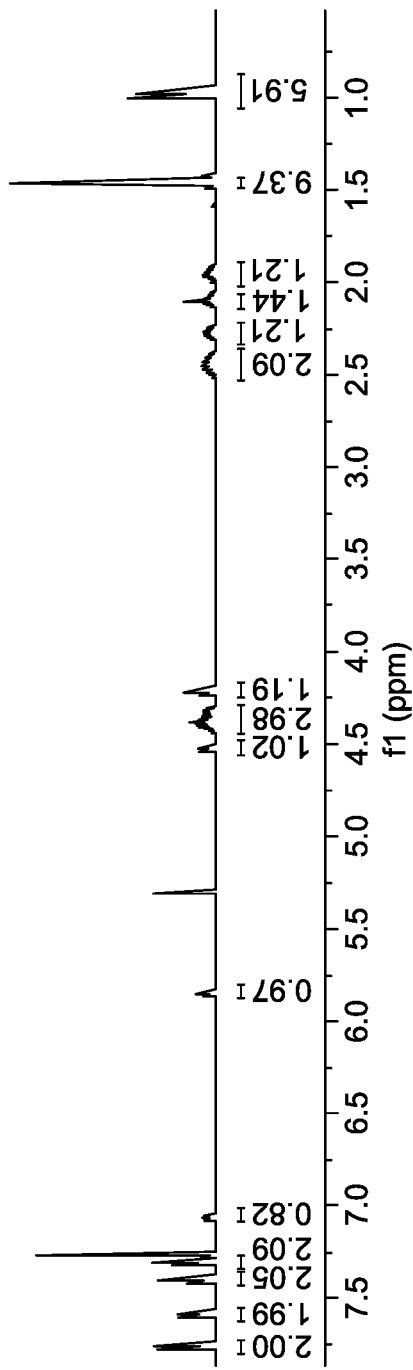
FIG. 27A-27C are NMR spectra of Fmoc-Glu(OtBu)-Val-OH after purification by silica gel chromatography, in chloroform d-1 (FIG. 27A), Fmoc-Glu(OtBu)-Val-Cit-OH after purification by precipitation, in methanol d-4 (FIG. 27B) and the product of addition of MMAE on activated Fmoc-Glu(OtBu)-Val-Cit-PABOH after precipitation in diethyl ether, in methanol d-4 (FIG. 27C).
Figure 27B:
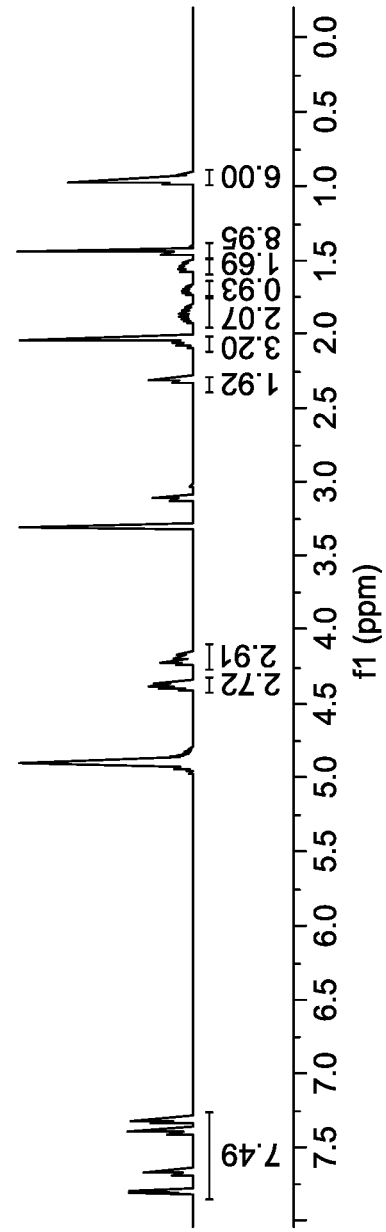
Figure 27C:
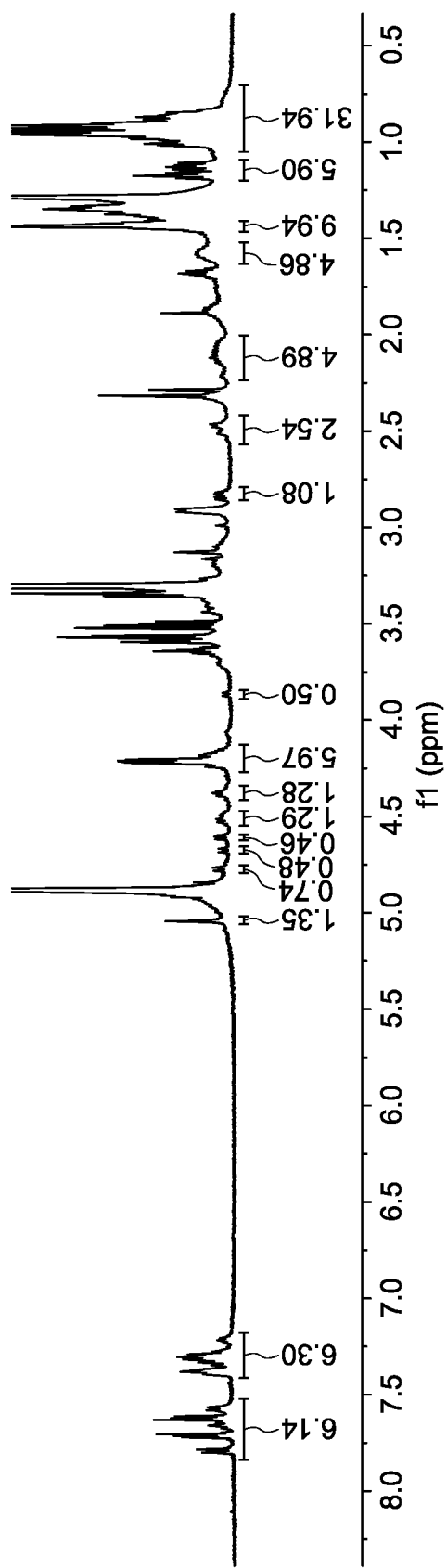

As described in FIG. 26, the tripeptide is synthesized from the N-terminus by sequences of NHS activation of the fmoc-protected amino acid or peptide, followed by addition on a basic aqueous solution of an amino acid. The first dipeptide intermediate is purified by extraction with 1M HCl/EtOAc followed by stepwise precipitation in 50% and 60% diethyl ether in heptanes. The second tripeptide intermediate is purified by extraction with water/EtOAc followed by precipitation in diethyl ether. The obtained peptides are shown by the 1NMR of the pure products in FIG. 27A and FIG. 27B. After coupling with PABOH and addition of a 4-nitrophenyl carbonate moiety, the activated linker can be used without further purification or precipitated by diethyl ether and then can be reacted with various payloads by nucleophilic addition in basic conditions. Then, Fmoc-deprotection free the amine of the tripeptide which can further be functionalized with conjugation moieties via an adapted strategy. For example, a carboxylic acid can be coupled via classic peptide coupling chemistry (EDC, HATU, etc.) and an activated NHS-ester can be added directly in the presence of a base. We confirmed the reactivity of the activated linker by addition of MMAE to Fmoc-protected tripeptide. In optimal conditions, complete reaction was shown by isolation of the pure product of addition (FIG. 27C).

Figure 28A:
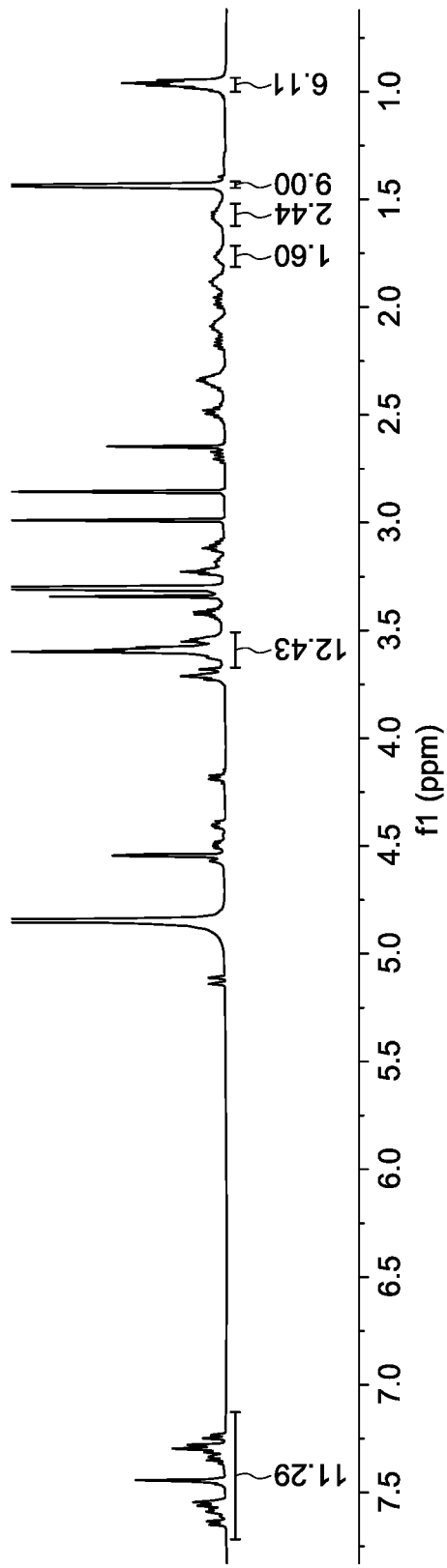
FIG. 28A-28C are NMR spectra of DBCO-PEG4-Glu(OtBu)-Val-Cit-PABOH after precipitation in cold diethyl ether followed by centrifugation at 13K RPM, in methanol d-4 (FIG. 28A), the product of addition of MMAE on activated DBCO-PEG4-Glu(OtBu)-Val-Cit-PABOH after precipitation in diethyl ether, in methanol d-1 (FIG. 28B) and the final deprotected linker-MMAE purified by precipitation in diethyl ether, in methanol d-4 (FIG. 28C).

Besides, we showed that free the amine of the tripeptide can be further conjugated it with DBCO-PEG$_4$-NHS (FIG. 28A). The resulting DBCO-PEG$_4$-Glu(OtBu)-Val-Cit-PABOH still can be conjugated with MMAE under the same conditions that are described above (FIG. 28B). The final deprotected product DBCO-PEG$_4$-Glu-Val-Cit-PABOC-MMAE after cold diethyl ether precipitation is shown in the FIG. 28C.

Figure 28B:
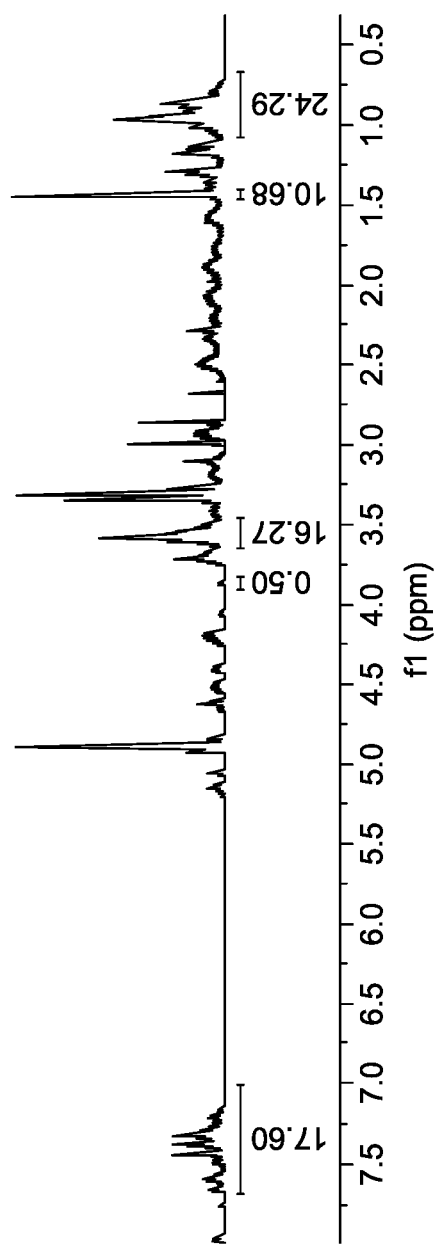
Figure 28C:
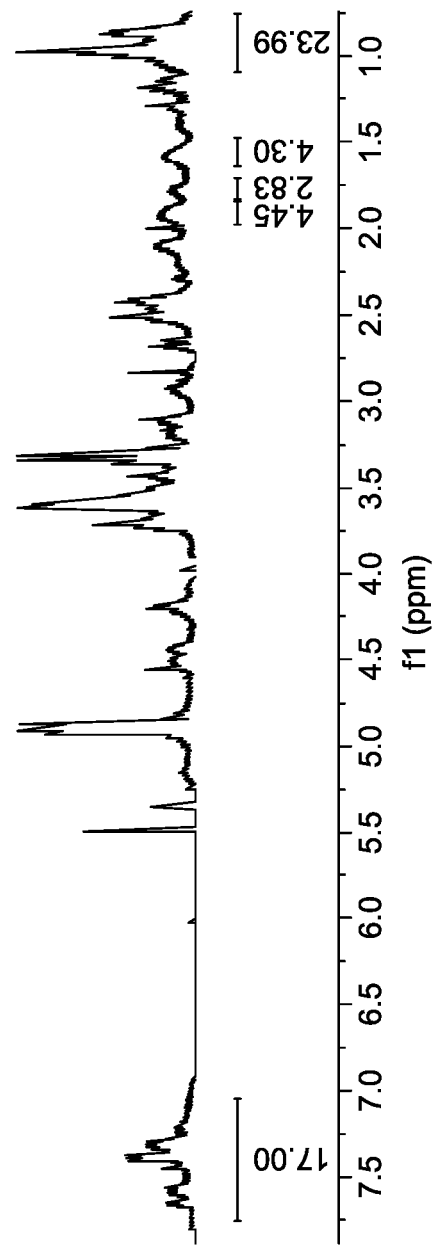

We have also shown that the DBCO/6-azido-lysine coupling is efficient, requiring only a 1.5 excess of DBCO tagged active agent such as a fluorophore or MMAE. Conjugation of the active agent to the docking peptide is confirmed by MALDI and IPLC analysis, as shown in FIG. 28A-28C. Similar results have been found for commercial DBCO-linked fluorophores such as FAM, TAMRA, and AlexaFluor 647.

Figures 29A, 29B:
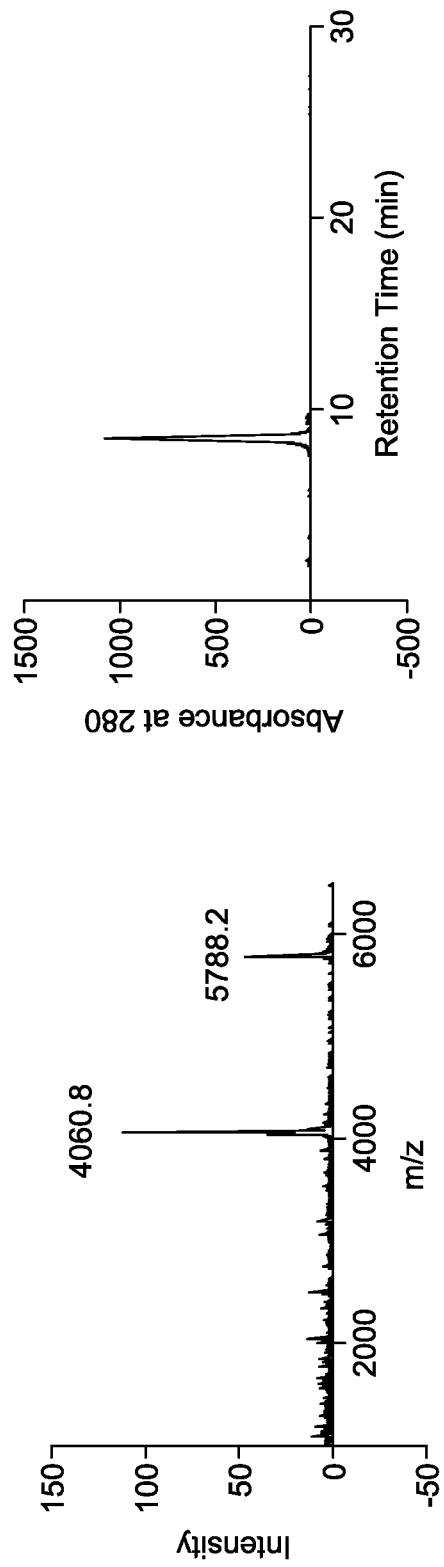
FIG. 29A is a MALDI spectrum of the docking peptide-DBCO-MMAE conjugate, showing the expected molecular weight (Expected 5790, observed 5788.2).
FIG. 29B is a HPLC chromatogram of the docking peptide-DBCO-MMAE conjugate of FIG. 29A showing the shift in retention time from the unconjugated peptide and high purity.

Using the TAMRA labelled docking peptide, V/E-TAMRA, we conducted an experiment to confirm that coiled coil formation on the antibody occurs and is not impeded by the conjugation of a fluorophore. We used size exclusion chromatography (SEC) and the following samples: V/E-TAMRA alone, Ab-V/K alone, Ab and V/E-TAMRA, and Ab-V/K and V/E-TAMRA. The samples were measured at both 280 nm (for general peptide/protein absorbance) and 553 nm (for TAMRA absorbance). The Ab and V/E-TAMRA was expected to not form the coiled coil and therefore have no absorbance at 553 nm as the antibody in this case does not have the receiving peptide sequence. Conversely, the antibody which does have the receiving peptide sequence, Ab-V/K, should have a corresponding absorbance at 553 nm as the coiled coil is formed and the antibody-fluorophore conjugate is created. As seen in the SEC chromatograms in FIG. 8, these predictions were proven correct. Additionally, the binding affinity of the antibody to its antigen after coiled coil formation was investigated and was found to not be affected by loading with the fluorophore labeled docking peptide, as shown by the ELISA results in FIG. 29.

Figure 30B:
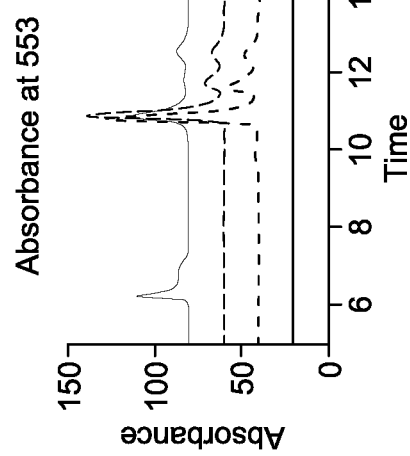
FIG. 30B is a SEC chromatogram of the sample absorbances at 553 nm. Notably, the only sample that has an absorbance at 553 nm that doesn't correspond to the V/E-TAMRA peptide is the sample group Ab-V/K+V/E-TAMRA. This demonstrates that the coiled coil is formed and the fluorophore is loaded onto the antibody. Additionally, this conjugation is specific to the coiled coil formation as the same antibody lacking the receiving peptide sequence does not form a fluorophore/antibody complex.
Figure 30A:
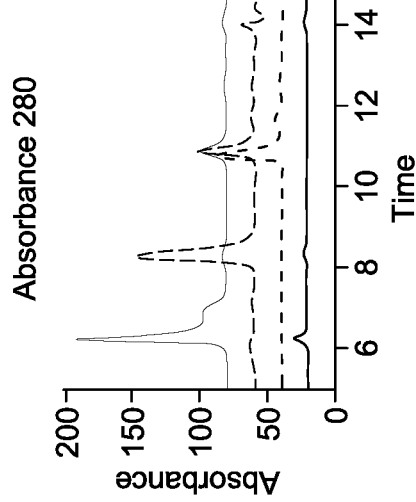
FIG. 30A is a SEC chromatogram showing absorbances at 280 of the different sample groups. Notably, Ab-V/K elutes at a retention time of around 6 min and V/E-TAMRA elutes around 11 min.

Additionally, we showed that the proposed conjugation approach can be extended to different antibodies and different architecture of coiled-coil peptides. For example, we produced human epidermal growth factor receptor 2 antibodies (αHER2) with inserted peptide sequences into heavy chain via recombinant techniques described previously in this patent (peptides sequences—P1: SPEDEIQQLEEE-IAQLEQKNAALKEKNQALKYGKG (SEQ ID NO: 10); P2: SPEDKIAQLKEKNAALKEKNQQLKEKLQALKYG (SEQ ID NO: 11); P3: SPEDEIQQLEEEIAQLEQK-NAALKEKNQALKYG (SEQ ID NO: 12); P4: SPEDKI-AQLKQKIQALKQENQQLEEENAALEYG (SEQ ID NO: 13). The chosen peptide sequences were shown to form orthogonal coiled-coil dimers instead of tetramers shown above (T. Lebar et al. 2020). According to the Circular Dichroism (CD) spectroscopy all resulting antibody-peptide formulations did not change the natural 3-sheet folding of antibodies (FIG. 30A).

Figure 30D:
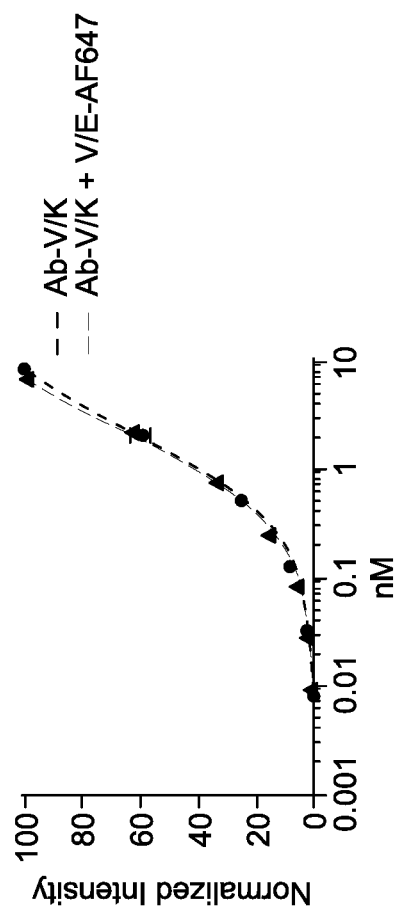
FIG. 30D is the same data in FIG. 30C, but with normalized intensities to better illustrate the that binding is the same between the two groups.
Figure 30C:
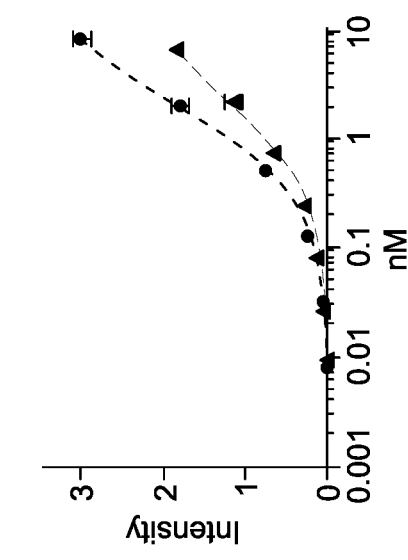
FIG. 30C is a graph showing results of ELISA demonstrating binding affinity of the antibody is not affected by loading with fluorophore, although it does hinder the binding of the secondary antibody used for read-out. Ab-V/K Kd: 2.18+/−0.08 nM and Ab-V/K+V/E-AF647 Kd: 2.20+/−0.15 nM.

However, they were of different molecular weight, which appeared as shortened retention time on Size Exclusion Chromatography (SEC). Similar to the CCK peptide, peptides with predominantly the same charge led to antibody aggregation while antibodies modified with P3 or P4 appeared as uniform narrow peaks making them preferable for ADC formulation (FIG. 30B). Nonetheless, compared to the tetrameric coiled-coil architecture, the difference between the elution times of native and modified antibodies is much smaller, indicating that the dimeric approach results in less protein aggregation. We further confirmed the modifications of antibodies with peptide tails by running non-reducing and reducing SDS-page gel for αHER2-P3 composition. The total molecular weight of the antibodies expressing the peptide was slightly increased compared to commercial trastuzumab antibodies and native antibodies (FIG. 30C). As expected, a similar change in molecular weight occurred for the αHER2-P3 heavy chain, while the light chain remained intact when running the reducing gel. Finally, we showed that the expressed P3 peptide does not interfere with the antibodies ability to recognize its target using a similar custom ELISA as before (FIG. 30D).

Figure 31B:
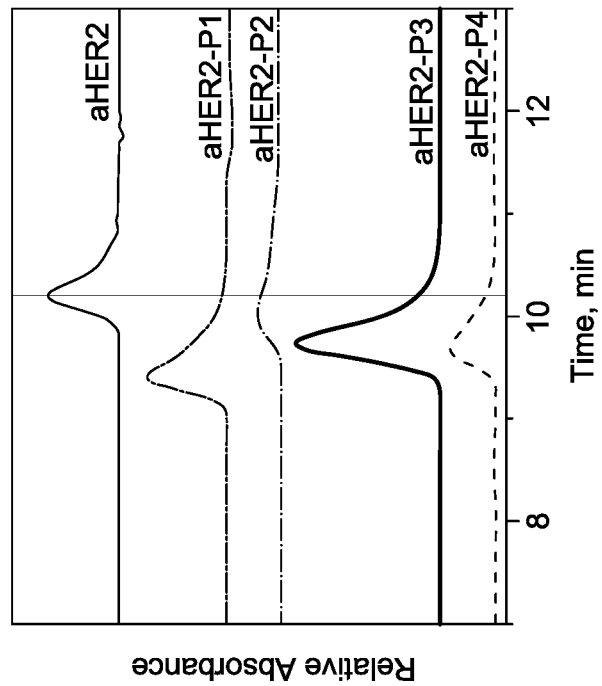
FIG. 31B depicts SEC analysis of native antibodies, αHER2-P1, αHER2-P2, αHER2-P3, and αHER2-P4 at 280 nm.
Figure 31A:
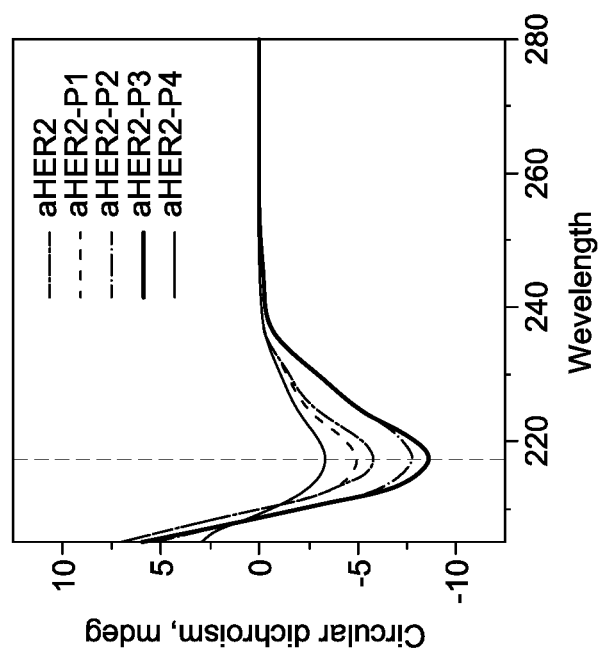
FIG. 31A is a CD spectra of native antibodies, αHER2-P1, αHER2-P2, αHER2-P3, and αHER2-P4 showing the 3-sheet folding of the antibodies.
Figure 31D:
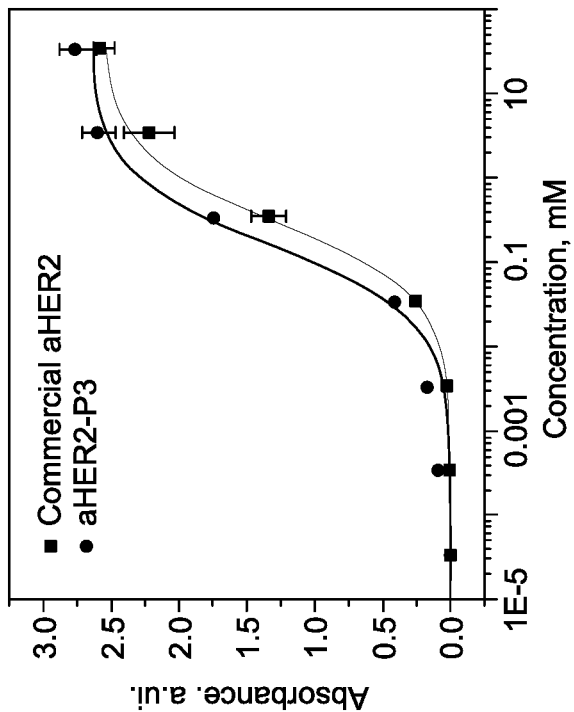
FIG. 31D shows ELISA based binding analysis of commercial antibodies compared to αHER2-P3.

To confirm that coiled-coil forming peptides are able to form dimeric structure being attached to an antibody we performed BLI experiment studying the binding of αHER2-P3 to immobilized biotinylated P4 peptide. Our results show that P3 being introduced into protein sequence is able to form stable structure with corresponding pairing peptide P4 with Kd of $6 \times 10^{-10}$ M (FIG. 31A).

Figure 31C:
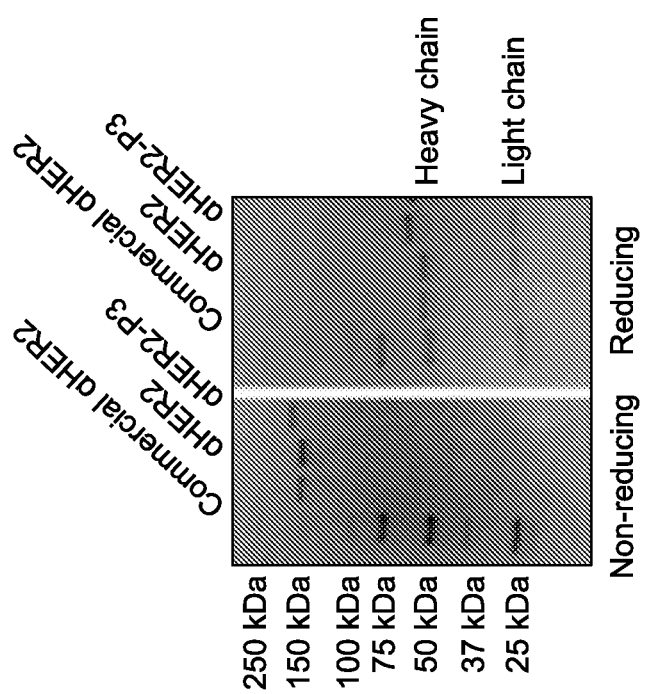
FIG. 31C is a SDS-PAGE gel of non-reduced and reduced commercial and produced αHER2 antibodies or αHER2 antibodies modified with P3 peptide showing a shift to higher molecular weight region for modified samples.
Figure 32B:
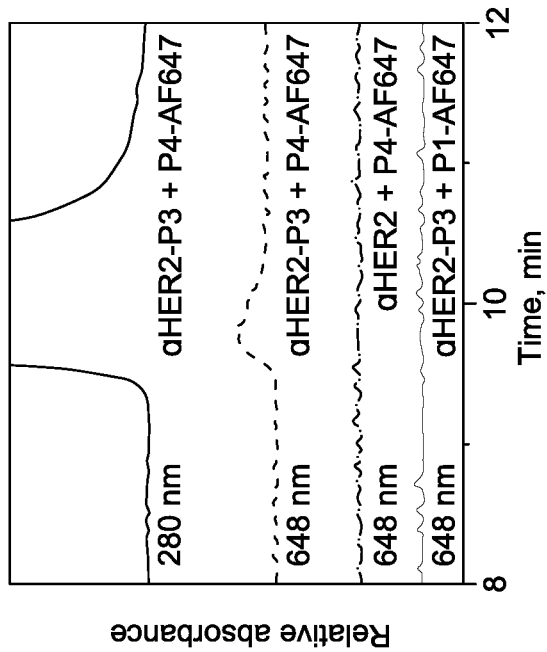
FIG. 32B is a size exclusion chromatogram showing the specific formation of AFC between αHER2-P3 antibody and pairing P4-AF647 peptide.
Figure 32A:
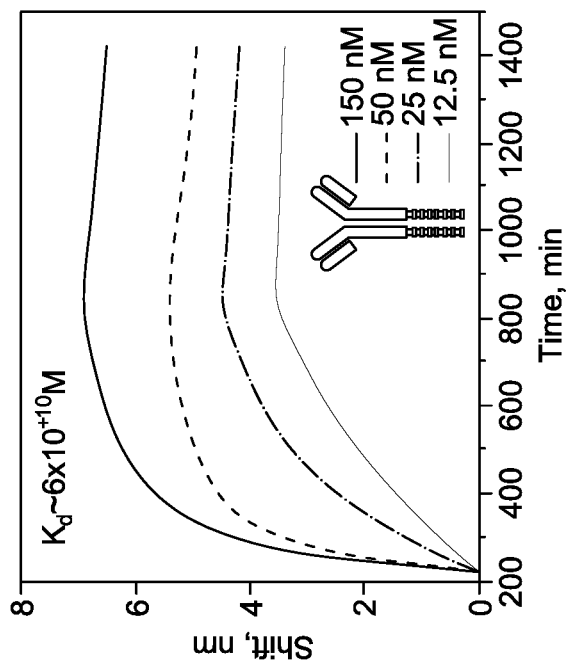
FIG. 32A depicts representative profiles of the binding of αHER2-P3 to P4 coated BLI tip at different concentrations.

To evaluate the specificity of coiled-coil based conjugation we used AlexaFluor647 labeled P4 peptide (AF647-P4) to form AFC as described above. The specific association of AF647-P4 with αHER2-P3 was confirmed with SEC by monitoring the absorbance at 280 and 648 nm. According to the chromatogram at 280 nm, which corresponds to proteins absorbance maxima, the antibodies elute around 10 min (FIG. 31B). When mixed with fluorophore-modified peptides, a small absorption peak appears at 648 nm for the αHER2-P3+AF647-P4 sample, while the other samples have no absorption, indicating specificity of coiled-coil formation. Finally, the efficacy of coiled-coil based payload loading was validated by calculating fluorophore-antibody ratio (FAR) using UV-Vis (FIG. 31C). Since the antibody consists of two P3-modified heavy chains, two AF647-P4 can form a dimer structure with each antibody, making the expected FAR equal to two. By measuring AFC absorbance at 280 nm and 647 nm, we determined an average FAR of ~1.8, which is close to our expectation, confirming effective payload loading.

As described previously, we prepared MMAE bearing ADC based on αHER2-P3 antibodies using pairing P4 peptide and DBCO-PEG4-Glu(OtBu)-Val-Cit-PABOC-MMAE linker. The toxicity of the new ADC was investigated in vitro in the HER2-positive cell lines: SKBR-3 and A549. We treated the cells with up to 10 µg/ml of ADC (equivalent to 100 ng/ml of MMAE) along with native antibodies and free drug at equivalent concentrations. As expected, native antibodies with no drug showed no cytotoxicity even at highest doses; however, the equivalent doses of MMAE and ADC reduced cell viability to 20% in 72 h.

Figure 33A:
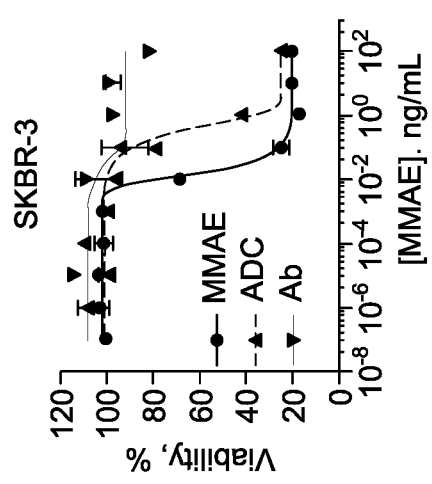
FIGS. 33A and 33B are cytotoxicity data of the ADC and equivalent MMAE and native antibodies for SKBR-3 (FIG. 33A) and A549 (FIG. 33B) cell lines over 72 hours of treatment.
Figure 33B:
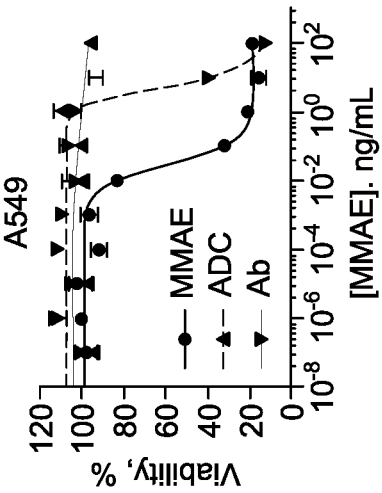
Figure 32C:
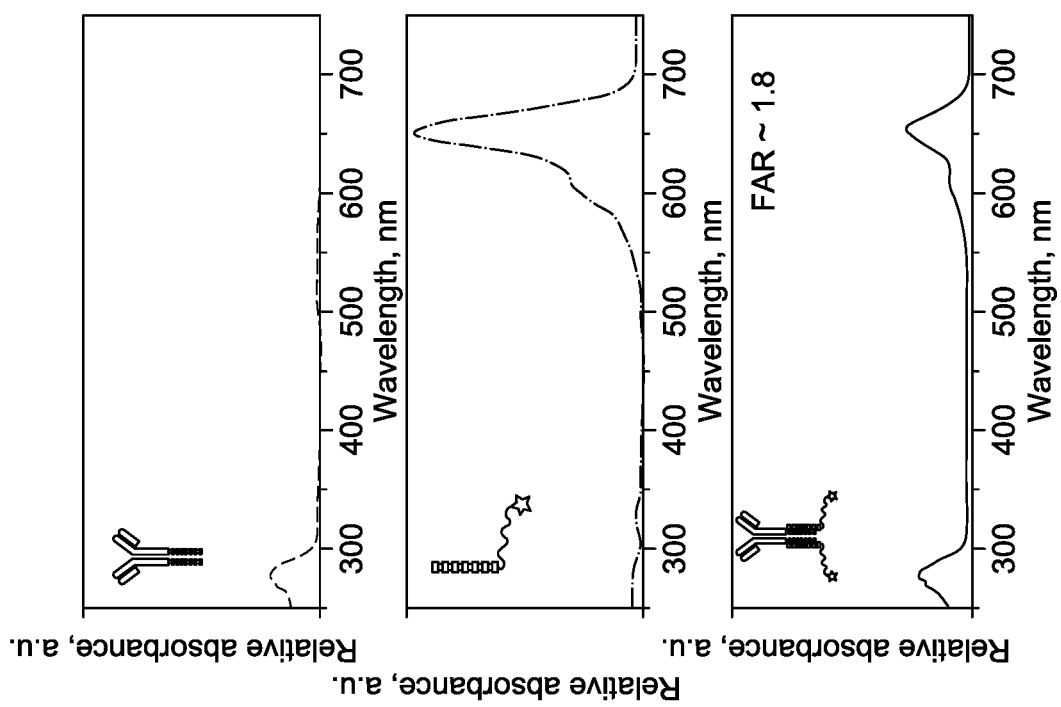
FIG. 32C shows absorbance spectra of αHER2-P3, P4-AF647 and AFC demonstrating the efficacy of AFC formation with fluorophore to antibody ratio (FAR) of 1.8.
Figure 34:
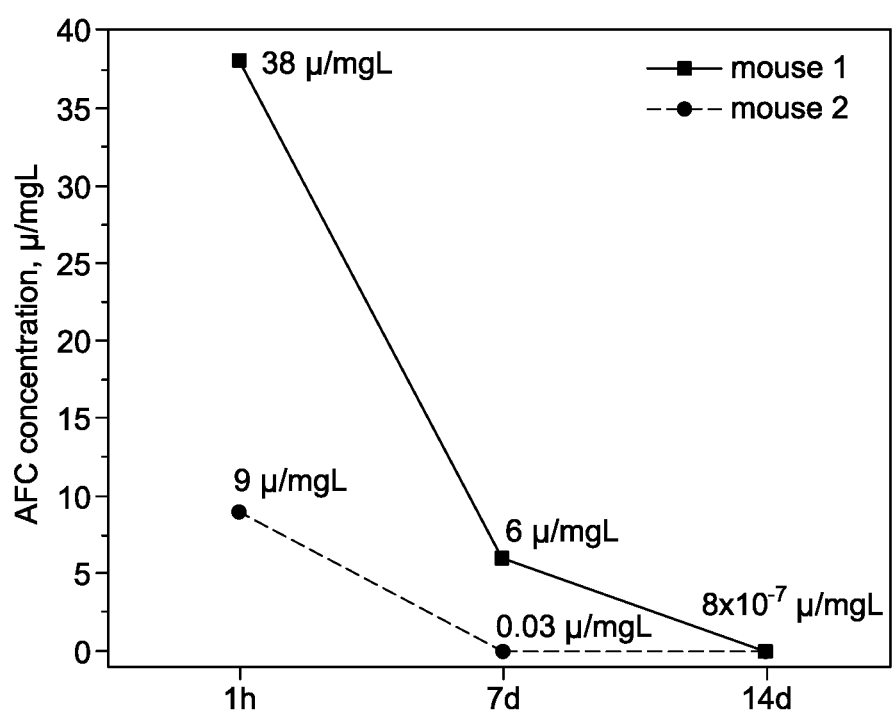
FIG. 34 depicts ELISA based analysis AFC concentration in mouse plasma over 2 weeks after single intravenous injection (10 mg/kg).
Figure 35B:
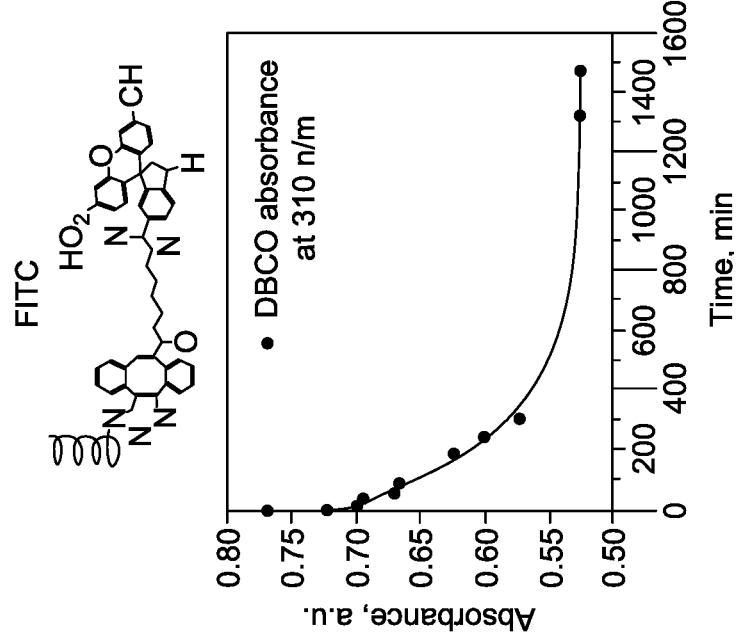
FIG. 35A-35D are UV-Vis analysis of DBCO reaction at 310 nm between coiled peptide and PEG4-Biotin (FIG. 35A), between coiled peptide and FITC fluorophore (FIG. 35B), between coiled peptide and PEG4-TAMRA fluorophore (FIG. 35C) and between coiled peptide and an oligonucleotide (FIG. 35D).
Figure 35A:
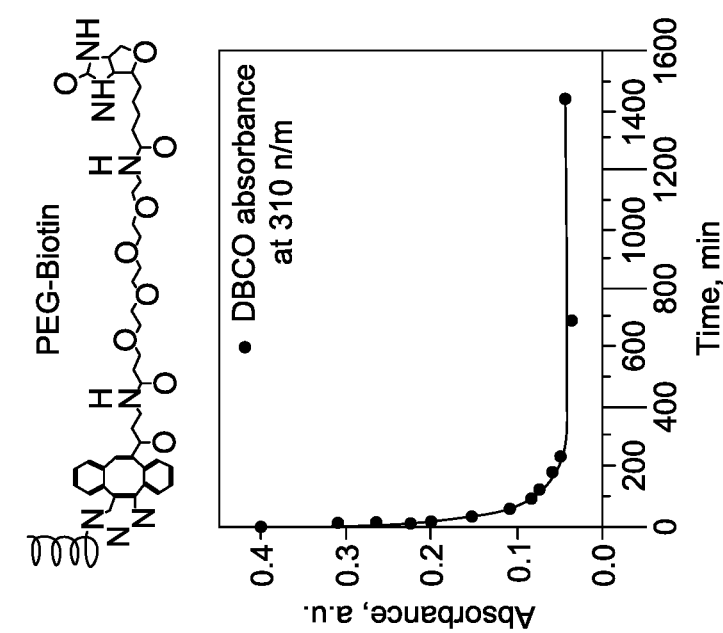
Figure 35D:
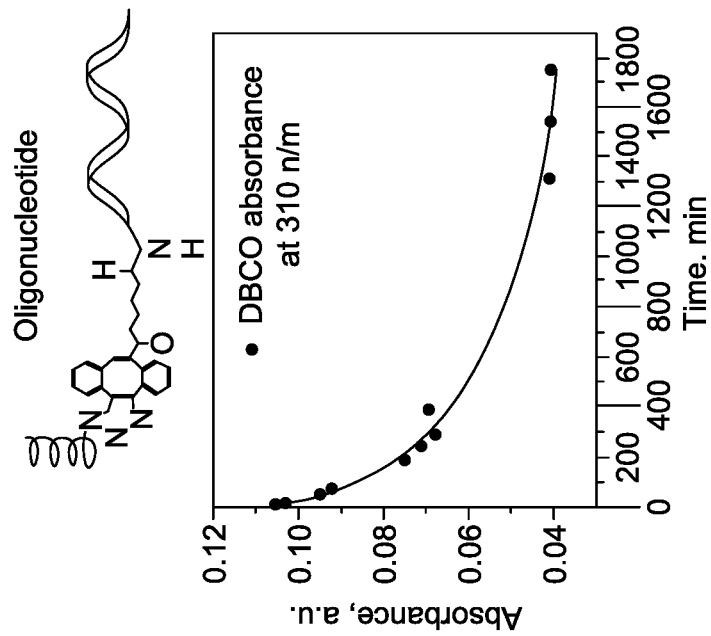
Figure 35C:
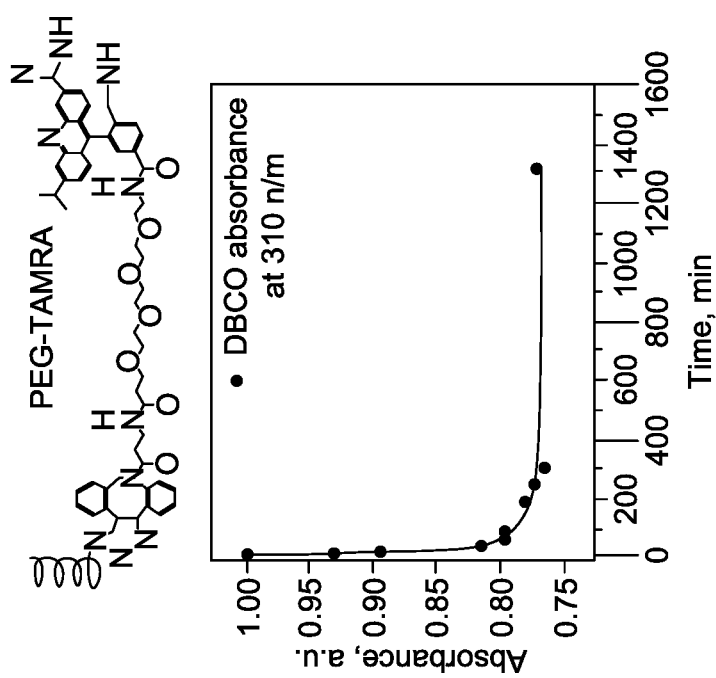

To make sure that the coiled-coil has no significant effect on antibody clearance, we performed a preliminary study of AFC concentration in blood plasma (FIG. 33). 10 mg/kg AFC was injected into two Balb/c mice. Blood samples were collected at 1 hour, 7 and 14 days and examined for AFC concentration by ELISA assay. A small amount of AFC was detected in plasma after 7 days, which is consistent with data reported earlier (Y. Anami et al. 2018, C. M. Yamazaki et al. 2021) suggesting that coiled-coil modification does not significantly changes antibodies pharmacokinetics.

To show that our conjugation platform can be extended to different payloads we studied the reaction between azide-modified docking peptide SPEDEIQALEEENAQLEQE-NAALEEE LAQLEYGK-azidoG (SEQ ID NO: 4) and DBCO-PEG4-biotin, DBCO-FITC, DBCO-PEG4-TAMRA, and DBCO-NTTTTTTTTTTGGTGGCGAGACG (SEQ ID NO: 71) oligonucleotide. By monitoring the change in absorbance at 310 nm (DBCO absorbance peak) we were able to identify the half-life of the reactions. The reactions with PEG modified payloads proceeded quickly with half-life ~10 min. However, reactions with DBCO-FITC and DBCO-oligonucleotide proceeded much slower with half-life ~109 min and half-life ~4 h respectively. We hypothesize this is likely due to low solubility of FITC in aqueous solutions and steric hinderance of the functional parts due to the absence of PEG arm. Nonetheless, all the payloads were successfully attached to the coiled-coil forming peptide suggesting that our platform is applicable for the delivery of the cargos of different nature.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An antibody, wherein a polypeptide chain of the antibody is linked on its C-terminus to a coiled-coil peptide, wherein the coiled-coil peptide is capable of forming a heterodimer with another coiled-coil peptide and comprises the amino acid sequence selected from the group consisting of:

SPEDEIQQLEEEIAQLEQKNAALKEKNQALKYGKG (SEQ ID NO: 10);

SPEDKIAQLKEK NAALKEKNQQLKEKLQALKYG (SEQ ID NO: 11);

SPEDEIQQLEEEIAQLEQKNAALKEKNQALKYG (SEQ ID NO: 12);

SPEDKIAQLKQKIQALKQENQQLEEENAALEYG (SEQ ID NO: 13);

MK LKKIKSV LKKIKSV LKKIKSV LKKIKSV VGER (SEQ ID NO: 1);

LKKIKSV LKKIKSV LKKIKSV LKKIKSV (SEQ ID NO: 5);

LKKIKSV LKKIKSV LKKIKKV LKKIKYV (SEQ ID NO: 6);

LEEIVSE LEEIVSE LEEIVSE LEEIVSE (SEQ ID NO: 7); or

LEEIVSE LEEIVSE LEEIVKE LEEIVYE (SEQ ID NO: 8), and wherein the antibody further comprises a second coiled-coil peptide forming a heterodimer with the coiled-coil peptide linked to the polypeptide chain of the antibody, and wherein the second coiled-coil peptide comprises the amino acid sequence SPEDEIQALEEEN-AQLEQENAALEEELAQLEYGK-azidoG (SEQ ID NO: 4); MK-LEEIVSE-LEEIVSE-LEEIV($X^1$)E-LEE-IVYE-VGER (SEQ ID NO: 51), where $X^1$ is lysine linked at N-ε position with —$X^2$-L, where $X^2$ is a linker and L is a ligand; or SPEDEIQALEEENAQLEQE-NAALEEE LAQLEYG($X^1$)KG (SEQ ID NO: 52), where $X^1$ is lysine linked at N-ε position with —$X^2$-L, where $X^2$ is a linker and L is a ligand.

2. The antibody of claim 1, wherein said polypeptide chain is a heavy chain of the antibody.

3. The antibody of claim 1, wherein the coiled-coil peptide linked to the polypeptide chain of the antibody comprises the amino acid sequence:
SPEDEIQQLEEEIAQLEQKNAALKEKNQALKYGKG (SEQ ID NO: 10);
SPEDKIAQLKEK NAALKEKNQQLKEKLQALKYG (SEQ ID NO: 11);
SPEDEIQQLEEEIAQLEQKNAALKEKNQALKYG (SEQ ID NO: 12); or
SPEDKIAQLKQKIQALKQENQQLEEENAALEYG (SEQ ID NO: 13).

4. The antibody of claim 3, wherein the coiled-coil peptide linked to the polypeptide chain of the antibody comprises the amino acid sequence of SEQ ID NO: 10.

5. The antibody of claim 1, wherein the coiled-coil peptide linked to the polypeptide chain of the antibody is linked to the C-terminus of the heavy chain via a peptide linker.

6. The antibody of claim 5, wherein the linker comprises a recognition amino acid sequence for a peptide ligase.

7. The antibody of claim 6, wherein the linker comprises a Sortase A recognition sequence.

8. The antibody of claim 7, wherein the linker comprises the amino acid sequence LPETG (SEQ ID NO: 48) or LPETGGGGG (SEQ ID NO: 50).

9. The antibody of claim 1, wherein the antibody is an anti-GPR87 antibody or an anti-DEspR antibody.

10. The antibody of claim 1, wherein the antibody is a monoclonal antibody.

11. The antibody of claim 1, wherein the second coiled-coil peptide comprises the amino acid sequence SPEDEIQALEEENAQLEQENAALEEE LAQLEYGK-azidoG (SEQ ID NO: 4).

12. The antibody of claim 1, wherein the second coiled-coil peptide comprises the amino acid sequence SPEDEIQALEEENAQLEQENAALEEE LAQLEYG($X^1$)KG (SEQ ID NO: 52), where $X^1$ is lysine linked at N-ε position with —$X^2$-L, where $X^2$ is a linker and L is a ligand.

13. The antibody of claim 1, wherein the ligand is selected from the group consisting of small organic and inorganic molecules, amino acids, peptides, polypeptides, peptidomimetics, glycoproteins, lectins, nucleosides, nucleotides, monosaccharides, disaccharides, trisaccharides, oligosaccharides, polysaccharides, lipopolysaccharides, vitamins, steroids, hormones, and cofactors.

14. The antibody of claim 1, wherein the ligand is a therapeutic agent, an imaging agent or a detectable label.

15. The antibody of claim 14, wherein the ligand is an anti-cancer agent.

16. The antibody of claim 1, wherein the ligand is linked to the second coiled-coil peptide via a linker comprising a cleavable linking group.

17. The antibody of claim 1, wherein the linker linking the ligand to the second coiled-coil peptide comprises the tripeptide glutamic acid-valine-citrulline (EVC).

18. The antibody of claim 17, wherein the linker comprises triethyleneglycol-glutamic acid-valine-citrulline-p-aminobenzylcarbamate ($PEG_3$-EVC-PABC).

19. The antibody of claim 1, wherein the coiled-coil peptide linked to the polypeptide chain of the antibody comprises the amino acid sequence GGGGG (SEQ ID NO: 55) at its N-terminus.

20. The antibody of claim 1, wherein the second coiled-coil peptide comprises the amino acid sequence MK-LEE-IVSE-LEEIVSE-LEEIV($X^1$)E-LEEIVYE-VGER (SEQ ID NO: 51), where $X^1$ is lysine linked at N-ε position with —$X^2$-L, where $X^2$ is a linker and L is a ligand.

21. An antibody, wherein a heavy chain of the antibody is linked on its C-terminus to a coiled-coil peptide, wherein the coiled-coil peptide is capable of forming a heterodimer with another coiled-coil peptide and comprises the amino acid sequence SEQ ID NO: 10, wherein the coiled-coil peptide is linked to the C-terminus of the heavy chain via a peptide linker comprising the amino acid sequence of SEQ ID NO: 55, wherein the antibody is conjugated with a ligand, and wherein the ligand is covalently linked with a coiled-coil peptide comprising the amino acid sequence of SEQ ID NO: 52.

22. A pharmaceutical composition comprising the antibody of claim 1 and a pharmaceutically acceptable carrier.

23. A method of delivering at least one ligand to a cell, the method comprising providing to the cell the antibody of claim 1.

* * * * *